(12) United States Patent
Davenport

(10) Patent No.: US 10,780,319 B2
(45) Date of Patent: *Sep. 22, 2020

(54) SIGNAL ANALYSIS AND RECHARGING SYSTEM

(71) Applicant: Roger A Davenport, Fort Lauderdale, FL (US)

(72) Inventor: Roger A Davenport, Fort Lauderdale, FL (US)

(*) Notice: Subject to any disclaimer, the term of this patent is extended or adjusted under 35 U.S.C. 154(b) by 47 days.

This patent is subject to a terminal disclaimer.

(21) Appl. No.: 16/260,038

(22) Filed: Jan. 28, 2019

(65) Prior Publication Data
US 2019/0151711 A1  May 23, 2019

Related U.S. Application Data

(63) Continuation of application No. 14/530,851, filed on Nov. 3, 2014, now Pat. No. 10,188,902.

(51) Int. Cl.
*A63B 57/00* (2015.01)
*A63B 53/00* (2015.01)
(Continued)

(52) U.S. Cl.
CPC ............ *A63B 24/0003* (2013.01); *A61B 5/11* (2013.01); *A63B 53/04* (2013.01); *A63B 53/0466* (2013.01); *A63B 57/00* (2013.01); *A63B 60/42* (2015.10); *A63B 69/3632* (2013.01); *G06F 1/263* (2013.01); *G09B 19/0038* (2013.01); *A63B 2053/0437* (2013.01); *A63B 2053/0458* (2013.01); *A63B 2220/20* (2013.01);
(Continued)

(58) Field of Classification Search
CPC .......... H02N 2/18; H02N 2/183; H02N 2/186; H01L 41/00; H01L 41/08; H01L 41/113; H01L 41/1132; A63B 2220/20; A63B 2220/34; A63B 2220/40; A63B 2220/50; A63B 2220/51; A63B 2220/54; A63B 2220/56; A63B 2220/58; A63B 2220/833; A63B 2225/00; A63B 2225/02; A63B 2225/50; A63B 24/003; A63B 60/42; A63B 57/00; A63B 24/0003; A63B 53/04; A63B 53/0466; A63B 69/3632; A63B 2053/0437; A63B 2053/0458; A61B 5/11; G06F 1/263; G09B 19/0038
See application file for complete search history.

(56) References Cited

U.S. PATENT DOCUMENTS 6,196,932 B1 * 3/2001 Marsh ................ A63B 24/0021
  473/223
6,248,021 B1 * 6/2001 Ognjanovic ....... A63B 69/3617
  473/131

(Continued)

*Primary Examiner* — Milap Shah
(74) *Attorney, Agent, or Firm* — Roger A Davenport, PA

(57) ABSTRACT

A measurement device may include one or more piezoelectric elements that output power signals. The device may split each power signal, analyzing a first portion of the signal while supplying a second portion to an energy storage assembly. A processor may dynamically adjust the first and second portions of each power signal to change how much of each power signal is used for signal processing versus energy storage, and may make the adjustments based on detected activities and/or pre-programmed timelines. The device may be used in or on sports equipment, such as a golf club.

20 Claims, 25 Drawing Sheets

(51) Int. Cl.
*H02N 2/18* (2006.01)
*H01L 41/00* (2013.01)
*A63B 24/00* (2006.01)
*A61B 5/11* (2006.01)
*G06F 1/26* (2006.01)
*A63B 53/04* (2015.01)
*G09B 19/00* (2006.01)
*A63B 69/36* (2006.01)
*A63B 60/42* (2015.01)

(52) U.S. Cl.
CPC ....... *A63B 2220/34* (2013.01); *A63B 2220/40* (2013.01); *A63B 2220/56* (2013.01); *A63B 2220/833* (2013.01); *A63B 2225/50* (2013.01)

(56) References Cited

U.S. PATENT DOCUMENTS

| | | | | |
|---|---|---|---|---|
| 7,815,516 B1* | 10/2010 | Mortimer | ........... | A63B 24/0021 473/257 |
| 9,504,895 B2* | 11/2016 | Davenport | ............. | A63B 60/00 |
| 9,968,839 B2* | 5/2018 | Davenport | ............. | A63B 60/00 |
| 10,188,902 B2* | 1/2019 | Davenport | ............. | A63B 60/42 |
| 2002/0171415 A1* | 11/2002 | Lim | ................... | A63B 69/3614 324/176 |
| 2003/0137221 A1* | 7/2003 | Radziemski | ........ | H01L 41/1875 310/339 |
| 2004/0226788 A1* | 11/2004 | Tanner | ................. | F16F 15/022 188/267.1 |
| 2005/0037862 A1* | 2/2005 | Hagood | ............. | A63B 53/0466 473/222 |
| 2006/0226739 A1* | 10/2006 | Sakai | ........................ | F03G 5/06 310/339 |
| 2007/0278902 A1* | 12/2007 | Rastegar | ................ | H02N 2/183 310/339 |
| 2009/0029793 A1* | 1/2009 | Cage | ................... | A63B 71/0009 473/324 |
| 2009/0120197 A1* | 5/2009 | Golden | .............. | A63B 24/0003 73/775 |
| 2009/0212665 A1* | 8/2009 | Koser | ................ | H01L 41/1136 310/339 |
| 2009/0233729 A1* | 9/2009 | Chiang | .................. | A63B 53/10 473/289 |
| 2010/0045241 A1* | 2/2010 | Nousiainen | ........... | H02N 2/186 320/137 |
| 2010/0274447 A1* | 10/2010 | Stumpf | .................. | G01D 18/00 701/36 |
| 2011/0151987 A1* | 6/2011 | Golden | .............. | A63B 24/0003 473/223 |
| 2011/0224007 A1* | 9/2011 | Molinari | ............. | A63B 37/0003 473/199 |
| 2012/0032518 A1* | 2/2012 | Huang | ................... | H02J 50/30 307/81 |
| 2012/0100923 A1* | 4/2012 | Davenport | ......... | A63B 24/0006 473/223 |
| 2016/0105140 A1* | 4/2016 | Taniguchi | ............... | H02J 3/383 700/287 |

* cited by examiner

SIGNAL ANALYSIS AND RECHARGING SYSTEM

CROSS REFERENCE TO RELATED APPLICATIONS

This patent application is a continuation of patent application Ser. No. 14/530,851, filed Nov. 3, 2014. All of the above stated applications are incorporated in their entirety by reference.

FIELD OF THE EMBODIMENTS

The embodiments generally relate to a measurement and analysis system for determining the effectiveness of a golfer's swing based on measurements made at the golf club head for free swing analysis and/or impact analysis. The free swing analysis relates the dynamic characterization of the club head orientation and motional descriptors time line for the entire swing related to a predetermined spatial reference location. The impact analysis related to ball impact on the club face with respect to location and force profiles. The system to measure both requires dynamics motional analysis, a relative spatial analysis without a contact or impact being made and analysis of impact.

BACKGROUND OF THE INVENTION

Systems and concepts for signal analysis have existed for many years. The existing systems typically have sensors attached to a device and sensor outputs are interpreted by a processor. This is also the case in analyzing sports equipment, such as a golf club, to determine improvements a player can make to their swing.

A system shown in U.S. Pat. No. 7,736,242 to Stites, shows an integrated golf club with acceleration sensors on the shaft and in the club head and communicates wirelessly. The system also discloses a club head with an impact module that may include a strain gage. The system in U.S. Pat. No. 7,736,242 does not teach or suggest an integrated electronic system golf club head that integrates impact sensors into the club head face in combination with acceleration measurement sensors located in the club head and further does not teach an antenna system that utilizes the electrical properties and shape of the club head as an integral component element of the antenna system design to increase power efficiency and further operating time duration based on storage capacity of energy device. The system does not provide for a method of free swing analysis with the ability to relate a measurement time line to a predetermined spatial reference location.

Another example of attaching sensors to a golf club is shown in U.S. Pat. No. 4,898,389 to Plutt, who claims a self-contained device for indicating the area of impact on the face of the club and the ball, and a means for an attachable and detachable sensor or sensor array that overlies the face of the club. Plutt's device does not provide for an imbedded impact sensor array in the clubface that functions in conjunction with internal three dimensional g-force sensors to provide a superset of time varying spatial force impact contours of the clubface with club head acceleration force parameters that can be calibrated for highly accurate spatial and force measurement. Plutt's device is susceptible to location inaccuracy due to the removable constraint of the sensors and is susceptible to sensor damage since the sensors come in direct contact with the ball.

U.S. Pat. No. 7,672,781 to Churchill uses receiver signal strength measurements with multiple directional antennas in combination with linear calculation methods based on acceleration measurements to determine the location of a movable bodies that could be a golf club. Churchill fails to contemplate using RSSI measurements without the use of directional sectorized antennas in combination with acceleration measurements analysis applied to a movable object with non-linear travel.

However, these systems fail to teach or suggest a self-contained device or integrated electronic system golf club head comprising the functions and methods of measuring a the entire free swing with the ability to relate the free swing metrics time line to a predetermined spatial location through the use of measuring three orthogonal acceleration axes across time with accelerometer(s) from within the club head and measuring a spatial relationship variable to a predetermined spatial location near or on the swing path by means of receiver signal strength measurements. Further, they do not provide free swing analysis capabilities with impact analysis capabilities facilitated with impact sensors integrated within the club face in a single integrated electronic club head. They also do not provide a convenient recharging mechanism.

BRIEF SUMMARY OF EMBODIMENTS

Embodiments herein include a golf swing analysis system that is capable measuring and providing comprehensive performance feedback for both free swings and impact swings that include the entire swing. In other words, the system is capable of measuring and analyzing an entire free swing with no club/ball contact or a golf swing with club/ball contact. Further, when a free swing analysis is being employed, the system provides comprehensive results in the form of a time line with a vast number of timing and dynamics swing metrics represented. Further the time line is also associated to one or more spatial locations related to the club head travel path. When swing and impact analysis is being employed both dynamics swing metrics are provided and a broad array of impact metrics such ball club face location, impact forces, impact duration and others.

An embodiment disclosed herein may include a club face distributed impact sensor system that measures both positive and negative pressure at different locations at a club face to construct a time-varying impact pressure profile. The system may include a non-conducting monolith within a club face and a plurality of pressure sensors imbedded within the non-conducting monolith, including at least first and second piezoelectric elements in one embodiment. The system may also include pressure measurement circuitry (e.g., A/D converters) that captures positive and negative pressure values of the first and second piezoelectric elements, wherein the positive and negative pressures are measured over a plurality of sample points during impact of a golf ball with the club face and used to build a time-varying impact pressure profile.

Additionally, the system may include a mechanism for placing a static pressure on the monolith, thereby increasing or decreasing pressure sensitivity and adjusting the ability to measure negative impact pressures away from the contact point on the club face.

In another embodiment, an integrated golf club may include an integrated electronic system golf club head that is attachable and detachable to a golf club shaft and the integrated electronic system golf club head has substantially the same physical and performance characteristics as a regulation golf club head of similar type. The integrated electronic system golf club head measure three orthogonal axis of acceleration during the entire swing and measures ball/club face impact force profiles distributed across club face throughout the time duration of the impact. Both types of measurements are synchronized on a single time line for swing and impact metric relationships. Additionally, RSSI (receiver signal strength measurements) are synchronized on the said time line to derive relative spatial relationships to predetermine spatial locations on or near the club head travel path of the swing.

Further the integrated electronic system golf club head communicates wirelessly using radio waves between itself and a user interface device. The transmission and reception of radio wave from the club head is efficiently facilitated by an integrated antenna system that by design defines and utilizes attributes including physical structure and electrical properties of the club head shell in the overall antenna system design. The integrated electronic system golf club head shell also serves as the physical structure for enclosing and mounting assemblies that provide the system functions including: sensing, data capture and processing, memory, communication signal wave generation and data formatting for wireless transmission and reception along with an energy source to operate the electronics.

The user interface face device that receives the sensor and RSSI data wirelessly from the integrated electronic system golf club head performs a series of algorithms to provides comprehensive feedback for swing characterization for detailed swing timing results, dynamic club head orientation and motion metrics and dynamics shaft actions all referenced to the spatial domain.

The benefits of an integrated electronic system golf club head is that it can perform substantially similar to that of a regulation golf club head of same type, while providing essential measurements of free swing and or impact performance characteristics to the golfer reliably over a time period that is of adequate length for a training session or round of golf. These requirements translated into an integrated electronics system golf club head with substantially the same physical properties of a similar type golf club head with regards to weight, center of gravity and structural impact performance. The integrated electronics system golf club head comprises a number of assemblies that include club face assembly including impact sensors, antenna system assembly including club head shell, electronics assembly, three dimensional acceleration sensor(s) assembly and energy source assembly. These assemblies all have a defined mass and weight that when assembled provide substantially the same coefficient of restitution, weight and center-of-gravity as a regulation golf club head of similar type. Therefore, this drives the requirement that the electronic measurement and communication support function assemblies be a light as possible while performing their required functions accurately and reliably over a defined period of time so enough mass of material is available for the club head shell structure to provide mechanical structural performance requirements to function as a high performance golf club head. To achieve the lightest weight electronic and support assemblies possible, the electronic component parts count must be minimized, and the electronic design including all processing and wireless communication must be optimized for power efficiency to reduce the size and weight of the energy source required to operate the electronics system for an adequate period of time. This invention is an integrated electronic system golf club head that preserves the golf club head physical performance properties and further utilizes the golf club head shell physical structure and electrical properties to reduce parts count, materials and improve power efficiency of the electronic processing and communication functions to reduce the physical weight of electronics while providing accurate and reliable measurement and wireless communication performance. Further, when integrated electronic system golf club head is combined with a golf club shaft with grip the combination become a complete golf swing and impact measurement system.

The first category of measured forces includes three dimensional motional acceleration forces at the club head during the entire golf swing including impact. The relationship between force and acceleration is $F(t)=m_{ch}a(t)$ where $F(t)$ is the time varying force vector, $m_{ch}$ is the known mass of the club head and $a(t)$ is the time varying acceleration vector experienced by a given acceleration force sensor. The three dimensional axial domain of the acceleration force vectors has its origin at or near the center of gravity and the axial domain is orientated with one axis referenced normal to the club head face and another axis aligned with a known or less than 6 degree unknown angle offset to anticipated non flexed shaft. The mechanism used to measure this category of motional forces is a three dimensional g-force acceleration sensor or sensors. The three orthogonal acceleration measurements along with RSSI (Receiver Signal Strength Indicator) measurements are used for free swing analysis to derive a result in the form of a swing metrics time line that is related to a one or more spatial reference location(s).

The second category of force measurements includes the impact pressure forces that occur across the golf club head face for the duration of time for clubface and ball impact. This time varying pressure force is a scalar pressure profile normal to the clubface that is a result of the impact force and location of the ball on the clubface. The relationship between pressure and force is $p(t)=F_{normal-to-A}(t) A$ where $p(t)$ is the time varying pressure experienced by a given pressure force sensor, $F_{normal-to-A}(t)$ is the time varying vector component of the force vector that is normal to the surface of the pressure force sensor and also the clubface, and A is the surface area of a given pressure force sensor element. The axial reference domain is the same for the g-force sensors described above with respect to club face. The mechanism to measure this category of pressure forces is an array of one or more pressure force sensors embedded in the club face that are measuring time varying impact pressure forces across the club face during the entire duration of club head face and ball impact.

Both categories of dynamic direct vector measurements and RSSI measurements are related with a single time line and a single shared physical domain allowing a large number highly accurate golf club free swing, swing and club/ball impact and club head to ball orientation metrics to be realized. To achieve this aggregate of direct physical measurements, the golf club head has embedded within it at least one acceleration three dimensional g-force sensor, RSSI circuitry in the receiver and at least one, but preferably a plurality of impact pressure force sensors geometrically distributed in the club head face.

The calculations for free swing analysis metric based on three orthogonal acceleration measurements is provided in detail by Davenport et al, U.S. Pat. No. 7,871,333 and assigned to Golf Impact listed above in the Cross Reference to Related Application section and incorporated by reference in its entirety. Further the derivation of a swing metrics time line with a relationship to one or more spatial locations using RSSI measurements in combination with acceleration measurements is provided in detail by Davenport, applications U.S. Ser. No. 13/225,433 and U.S. Ser. No. 13/229,635 and both assigned to Golf Impact listed above in the Cross Reference to Related Application section and incorporated by reference in its entirety.

The free swing time metrics that are calculated with associated spatial relationship to one or more predetermined locations include:

1. Dynamically changing characteristic of club head velocity for a substantial portion before, through and after a maximum velocity of said club head in correlation to the dynamic spatial relationship of said club head to said predefined location.
2. Dynamically changing characteristic of toe down angle for a substantial portion before, through and after a maximum velocity of said club head in correlation to the dynamic spatial relationship of said club head to said predefined location.
3. Dynamically changing characteristic of club face angle for a substantial portion before, through and after a maximum velocity of said club head in correlation to the dynamic spatial relationship of said club head to said predefined location.
4. Dynamically changing characteristic of swing radius for a substantial portion before, through and after a maximum velocity of said club head in correlation to the dynamic spatial relationship of said club head to said predefined location.
5. Dynamically changing characteristic of club head spatial acceleration for a substantial portion before, through and after a maximum velocity of said club head in correlation to the dynamic spatial relationship of said club head to said predefined location.
6. Dynamically changing characteristic of club head radial acceleration for a substantial portion before, through and after a maximum velocity of said club head in correlation to the dynamic spatial relationship of said club head to said predefined location.
7. Dynamically changing characteristic of shaft flex lag lead angle for a substantial portion before, through and after a maximum velocity of said club head in correlation to the dynamic spatial relationship of said club head to said predefined location.
8. Dynamically changing characteristic of wrist cock angle for a substantial portion before, through and after a maximum velocity of said club head in correlation to the dynamic spatial relationship of said club head to said predefined location.
9. a line that is coincident with the swing plane and swing plane angle to ground.
10. Detailed club head swing tempo profile which includes total time duration of tempo for the backswing, pause and reversal, and power-stroke and provides rhythm described as a percentage break down of each segment duration compared to total tempo segment duration.

The impact metrics that are measured and or calculated include:

1. Time varying pressure or force profile across the golf clubface;
2. Location of impact of clubface and ball on clubface;
3. Duration in time of club head face and ball impact;
4. Maximum pressure or force measured on clubface;
5. Total energy transferred from club to ball;
6. Force vector components that are transferred to ball launch and ball spin;
7. Estimated percent of total energy components transferred to ball trajectory and ball spin;
8. Orientation of ball spin referenced to club head face;
9. Estimation of ball launch velocity;
10. Estimation of ball spin velocity;
11. Impact error offset on clubface which is a distance from actual impact location to optimum impact location
12. Club head orientation percentage error from optimum in relation to club head/ball impact (This could be described as an error for each of three vectors describing forces on club head from ball) and;
13. Measure of torque and angular momentum of the club head as caused by the event of club head/ball impact.

The sensors are connected to electrical analog and digital circuitry and an energy storage/supply device, also embedded within the club head shell cavity. Further the analog and digital circuitry with RSSI measurements circuitry also referred to as electronics is electrically connected to an antenna system that uses the club head shell as an electrical conductive element as part of the antenna system. The analog and digital circuitry electronic assembly conditions the signals from the sensors, samples the signals from each sensor group category, converts to a digital format, attaches a time stamp to each category or group type of simultaneous sensor measurements, and then stores the data in memory. The process of sampling sensors simultaneously for each sensor category or group type is sequentially repeated at a fast rate and may be a different rate between sensor categories or group types, so that all measured points from each sensor category or group type are relatively smooth with respect to time. The minimum sampling rate is the "Nyquist rate" of the highest significant and pertinent frequency domain component for each of the sensors' category or group types time wave representations.

The electronics assembly further temporarily stores the measured data sets and further formats the data into protocol structures for wireless transmission. Each data set is queued and then transmitted in a wireless protocol format from a radio frequency transceiver circuit that is electrically connected to an antenna system assembly electrical port. The antenna system comprises at least two electrically conducting elements. One of the electrically conducting elements of the antenna system assembly is the electrically conductive club head shell. The shapes and sizes of all antenna elements and objects are optimized as an antenna system to provide a desired input electrical port impedance characteristic and a desired radio wave radiation pattern for the antenna system. Further the electrically conductive club head element and club face assembly also provides the physical structure and performance attributes of a functional golf club head.

The combined weight of all assemblies of the integrated electronics system golf club head is substantially equal to that of a regulation play club head of similar type. In addition, the mounting location of all pieces of all assemblies either internal to the club head shell or external to the club head shell are configured so the center of gravity of the integrated electronics system golf club head is substantially similar to that of regulation play golf club head of similar type that is considered to deliver good performance.

This invention also provides a variety of methods including the sequence of steps that may be used to effectively optimize all of the variable that are encountered with the design of integrated electronic system golf club head, taking into account the many tradeoffs between dual function requirements placed on individual components and structures.

The present invention encompasses a variety of options for the golfer to receive and interpret the information of swing, impact and orientation metrics or a subset of total metrics available. The human interface function is separate human interface device that communicates wirelessly with the integrated electronic system golf club head. The human interface function can provide all or any subset of audible and visual outputs. Examples may include wireless smart device such as a PDA or laptop computer or any other device that has processing capabilities and a display and audio capabilities and can be adapted to communicate wirelessly using standard or non-standard wireless protocols. Some of the standard wireless protocols may include but not limited to ZigBee, Blue-Tooth or WiFi. Some of the non-standard protocol may include a completely custom modulation with associated custom protocol data structure or standard high level packet structure based on 802.11 or 802.15 with custom sub-packet data structure within high level packet structure.

The preferred embodiment of the integrated golf club, in addition to the previous described electronics, also has data formatting for wireless transport using Bluetooth™ transceiver protocols. The data, once transferred over the wireless link to the laptop computer, are processed and formatted into visual and or audio content with a proprietary software program specific for this invention. Examples of user selectable information formats and content could be:

1. a dialog window showing a graphical representation of the clubface using a color force representation of the maximum force gradient achieved conveying the area of impact of the ball and along the side the graphic could show text describing key metrics such as maximum force achieved, radial acceleration of club at impact (related to club head velocity) and total energy transferred to the ball;
2. a motion video of the time varying nature of the forces on the clubface;
3. a three dimensional graphic showing force vectors on club head from ball;
4. an audio response which verbally speaks to the golfer telling him/her the desired metrics;
5. a video showing time varying acceleration vectors of the golf club head during the swing and through impact; or
6. numerous other combinations of audio and visual user defined.

BRIEF DESCRIPTION OF DRAWINGS

The above and other features of the present invention will become more apparent upon reading the following detailed description in conjunction with the accompanying drawings, in which:

FIGS. 19A and 19B show and front view and a side view of the club head travel path with possible predetermined locations for the placement of the wireless USB module.

DETAILED DESCRIPTION OF EMBODIMENTS

An embodiment disclosed herein may include a device with one or more piezoelectric elements and a processor, wherein the output signal of each piezoelectric element may be divided such that a first portion is analyzed and/or processed and a second portion is used to recharge a battery. The ratio of the first portion to the second portion may be dynamically adjusted by the processor in one embodiment, based on detections made by the processor. The system may include, for example, a non-conducting monolith with a plurality of pressure sensors imbedded within it, including at least first and second piezoelectric elements in one embodiment. The system may also include pressure measurement circuitry (e.g., A/D converters) that captures positive and negative pressure values of the first and second piezoelectric elements, wherein the positive and negative pressure values are measured over a plurality of sample points. This may be used, for example, with a golf club for measurement of an impact of a golf ball with the club face and used to build a time-varying impact pressure profile.

Figure 1:
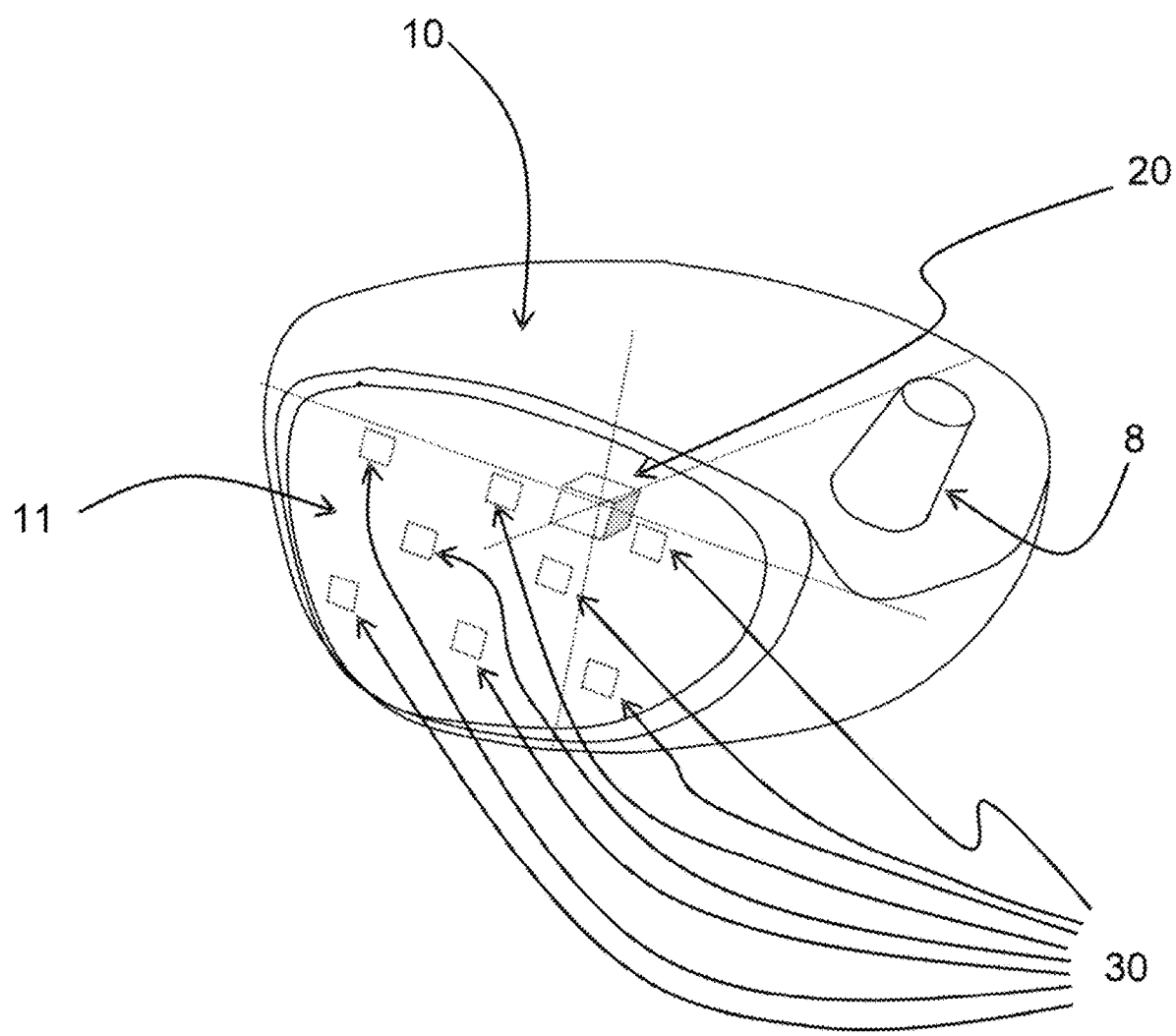
FIG. 1 is a perspective view of the present invention integrated golf club head (golf club shaft not shown) with impact pressure force sensors embedded in the clubface and a three dimensional g-force acceleration sensor inside the club head.

As shown in FIG. 1, the golf club head 10, has a three dimensional g-force acceleration sensor 20 mounted within the electrically conductive club head 10 shell cavity at a predetermined location. In one of many embodiments for this invention, the sensor(s) can be placed at a predetermined location that is the center of gravity of the club head 10 for simplification of metric calculations. However, the sensor(s) does not have to be located at the center of gravity and all metrics defined are still achievable. The club head 10, also has an array of impact pressure force sensors 30 embedded in the golf club head face 11. The hosel 8 may be made of a material that electrically conductive or electrically non-conductive depending on embodiment implementation and is attached to the club head 10. The hosel may be adapted to connect and disconnect from a golf club shaft (not shown) of the club.

Figure 2:
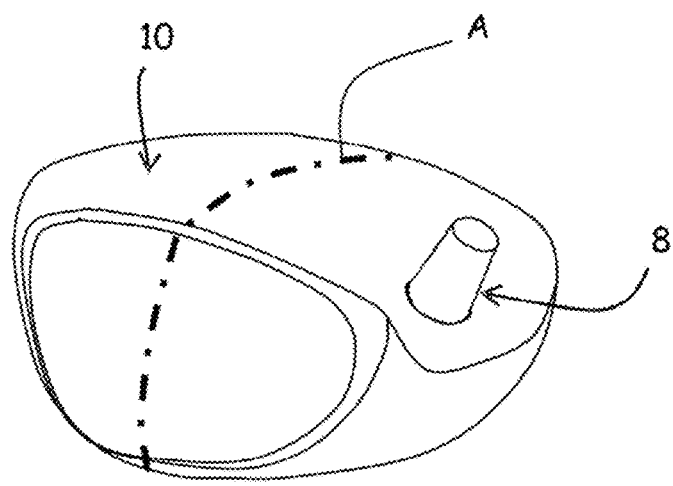
FIG. 2 is a perspective view of the present invention as shown in FIG. 1 except showing dashed line A and without depiction of the sensors.
Figure 2A:
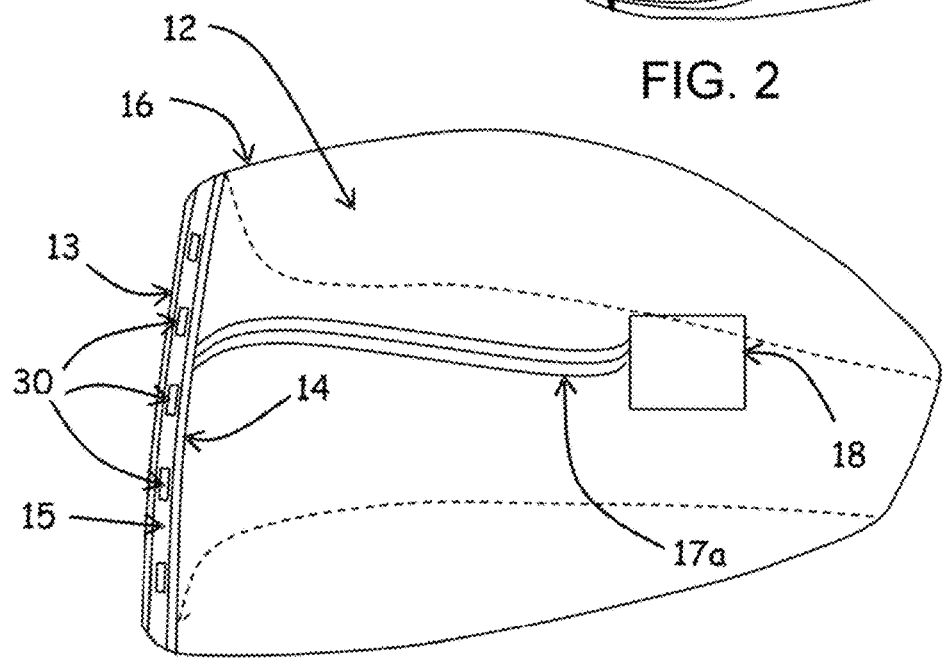
FIG. 2A is a cross sectional view of the club head of the present invention of FIG. 2 taken along line A showing clubface structure with two metal layers and there between the impact pressure force sensor elements within embedding material monolith and further sensor elements electrical connected to electronics module within club head shell
Figure 2B:
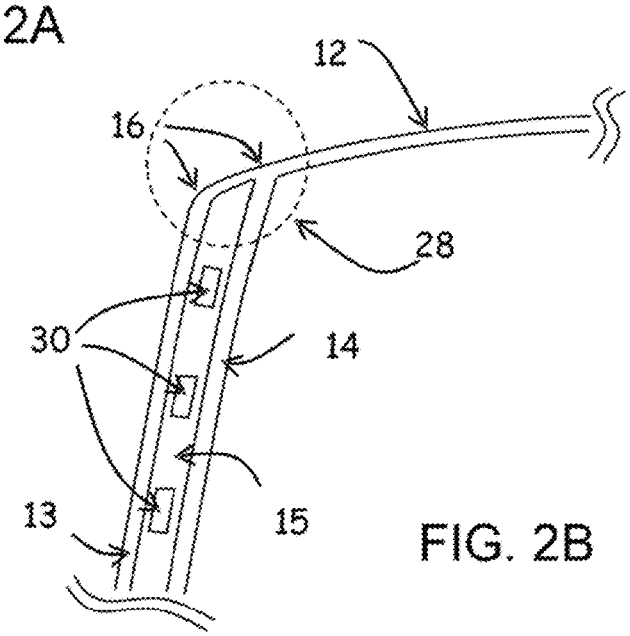
FIG. 2B is a partially exploded cross sectional view of the club head face assembly of the present invention showing two metal layers both rigidly attached the club head shell housing.

As shown in FIGS. 2, 2A and 2B the club head 10 and a club head cross section view FIG. 2A and FIG. 2B show selected assemblies. FIG. 2A show cross sectional view 12 of club head 10 showing the construction of the club face 11 assembly having two metal layers, the outer layer 13 and the inner layer 14. The outer and inner layers 13, 14 are made with predetermined materials that may be the same or different. In the preferred embodiment both layer 13 and layer 14 are both made of a metal type material. The pressure force sensors 30 are imbedded in a non-metallic, non-electrical conducting medium of optimum physical properties 15 between the two layers 13 and 14 as part of the clubface 11. The non-conducting medium 15 is a hard epoxy or similar material monolith structure with the pressure sensors 30 and their electrical connections embedded within it. Some examples of possible materials include UV curable epoxies such as UV Cure 60-71 05™ or medium to hard composition of Vantico™ or one of the compositions of Araldite™ or other suitable materials. The monolith structure can be created with exact pressure sensor placement and orientation with known injection molding technologies. An example of this process would be to make an injection mold that creates half of the monolith structure and has half pockets for a precise fit for each of the sensors and electrical connection ribbon. The sensors 30 with electrical connections are then placed in the preformed pockets of the initial half monolith. The initial half monolith with sensors is then placed in a second injection mold which completes the entire monolith. The sensors 30 are attached to a flex circuit ribbon 17a that will extend out from the monolith structure, through a small pass through opening in the inner layer 14, that connects to the electronics assembly 18 in the club head cavity. The electronics assembly 18 includes the RSSI circuitry that is used to measure receiver signal strength which will be covered in more detail later.

The non-conducting monolith material 15 with embedded pressure sensors 30 can be pressure fit between the outer layer 13 and the inner layer 14. The outer layer 13 and the inner layer 14 can be connected to the club head shell housing 16 with conventional club head construction techniques utilizing weld seams or other attachment processes. Some techniques might include Aluminum MIG (Metal Inert Gas) welding for aluminum to aluminum connection and brazing for aluminum to titanium connections. The clubface layers 13 and 14 can be titanium or comparable metal or alloy and the club head housing components can be an aluminum or alloy.

As shown in FIG. 2B, another cross sectional expanded view which is the preferred embodiment of the present invention, the inner metal layer 14 is a predetermined thickness and shape with a defined rigidness the outer clubface layer 13 is a predefined thickness and shape with a defined rigidness that define a club face system when combined with monolith 15. Both the outer layer 13 and the inner layer 14 are rigidly attached to the club shell housing 16 through the aforementioned welding process. In this configuration, the pressure exerted and resulting deformation on the outer layer 13 of golf clubface 11 resulting from ball and club face impact create a time varying pressure profile on the non-metallic medium monolith 15. The individual pressure sensors 30 each generate an output voltage proportional to the pressure experienced by that sensor. The pressure force sensors each may be any predetermined size and shape individually. However, the pressure sensors elements 30 in the preferred embodiment are piezoelectric elements made of a predetermined material with the same predetermined shape, surface area and thickness, therefore generating identical pressure force versus voltage profiles. In the case where the clubface inner 14 and outer 13 metal layers are both rigidly connected to the club head shell housing 16, the deformation of the monolith 15 will be less near the edge 28 of the clubface. This means that less pressure will be measured for the same impact force by sensors closer to the edge of the club face 11. These variations will be a constant with respect to the fixed geometric shape of club face system in combination with club head 10 shell and can be calibrated out in the digital signal process with fixed calibration coefficients programmed into the processing. Calibration coefficients may be determined through simulation or during production on a per club head type basis.

The predetermined materials used and predetermined shapes and thicknesses of all components of the club face structure assembly are individually optimized to further optimize the physical properties of the overall club face system to be substantially similar to that of a regulation play golf club head face of similar type and to provide adequate sensitivity of sensor embedded 30 in monolith structure 15. The process for design optimization of the club face system assembly defines the material properties used for each individual piece of the club face assembly and also the physical structure including size and shape of each individual piece of the club face assembly. Further the defined materials, shapes and sizes of all pieces further defines the club head face system overall weight and form factor and mass distribution. The process for design optimization of the club face system is a sub process of the overall design optimization process of the integrated electronics system golf club head.

The process for design optimizing the club face system takes into account several considerations and tradeoffs. The primary two objectives are to define a club face system structure that physically performs like a regulation club face of similar type and also provides adequate sensor sensitivity across the club face to measure with reasonable resolution ball/club face impact relative to a reasonable dynamic range of club head speeds at impact. An example dynamic range for a driver type may be 45 MPH to 130 MPH. Secondary goals are to achieve the lowest weight possible for the club face system providing maximum flexibility for the final optimization process that defines final weight and mass distribution of integrated electronics system golf club head design. Therefore a means of defining the optimal predetermined materials, sizes and shapes for all components of the club face assembly are done with the design optimization process for the club face system include the steps of:

1. Choose club head type
2. Choose a typical club head speed dynamic range for that golf club type in association with targeted golfer population skill level.
3. Choose a piezoelectric material that will provide high electromechanical coupling coefficient for sensor element(s) 30 for electronic measurement resolution purposes.
4. Choose metal material for outer club face layer 13
5. Choose material for inner club face layer 14
6. Choose attachment mechanism for club face assembly attachment to club head shell.
7. Choose material for monolith for embedding sensor elements 30 and define an initial size and shape of impact sensor elements based on knowledge monolith material.
8. Start with initial thickness and shape factor of outer club face layer 13 similar to that of a regulation club of that type.
9. Choose an initial thickness shape factor for inner club face layer 14 that is substantially thinner and has similar shape factor of initial outer club face layer 13
10. Choose an initial thickness of monolith that is 1.5-2 times the thickness of the sensor elements based on piezoelectric material selection in step 3.
11. Model with a Finite Element Simulator that has piezoelectric modeling capabilities such as PZ-Flex™ the layered structure comprising, outer layer 13, monolith 15 and inner layer 14, with all edges bound in accordance with step 6.
12. Through simulation, record voltage waveforms for all sensor elements for time varying loads applied to outer surface of outer layer 13 representing a golf ball impact of a predetermined speed and predetermined location on club face.
13. Repeat step 11 for different impact speeds from lowest to highest defined by the step 2 dynamic range for a specific location on the club face.
14. Repeat step 12 for different impact location on club face.
15. Evaluate elastic response characteristics of club face system compared to a regulation club face of similar club type in relation to COR (Coefficient of Restitution).
16. Evaluate electrical response of sensor outputs based on maximum amplitude measure at maximum club head velocity with impact at the center of the club face.
17. Evaluate electrical response of a sensor with maximum output at minimum velocity for a ball impact near a bound edge.
18. Define dynamic range regarding electrical sensor out from step 16 defining high end of dynamic range across club face and from step 17 for low end of dynamic range across club face.
19. Evaluate if electrical dynamic range of sensor outputs for entire club face (from step 18) provides adequate sensitivity for defined data capture constraints of electronics assembly.
20. Evaluate elastic response characteristics of club face system (from step 15) are within a defined tolerance when compared to a regulation golf club face of similar type.
21. If steps 19 and 20 are satisfied, optimization is complete. If one or both criteria are not satisfied adjust control parameters that include thickness of metal layers 13 and 14 and monolith layer 15 in the flowing manner:
    a. If electrical dynamic range is too small to provide adequate sensitivity do any single or combination of the following:
       i. Increase metal layer thickness 14
       ii. Decrease metal layer thickness 13
       iii. Decrease monolith layer 15
    b. If electrical dynamic range is larger than require for adequate sensitivity do any single or combination of the following:

i. Do nothing and move to strait to elastic response adjustments if needed—and reduce sensor signal levels uniformly in electronics assembly before data capture
ii. Increase metal layer thickness 13
iii. Decrease metal layer thickness 14
iv. Increase monolith layer 15
c. If elastic response of club face system is to stiff do any single or combination of the following:
i. Decrease metal layer thickness 13
ii. Increase monolith layer thickness 15
iii. Decrease metal layer thickness 14
d. If electric response is too soft, do any single combination of the following:
i. Increase metal layer thickness 13
ii. Decrease monolith layer thickness 15
iii. Increase metal layer thickness 14
22. Select control parameters to adjust electrical and mechanical responses and feed new control parameters based on step 21 a, b, c, d into step 11 and repeat process until club face system performance criteria are met.

Figure 3:
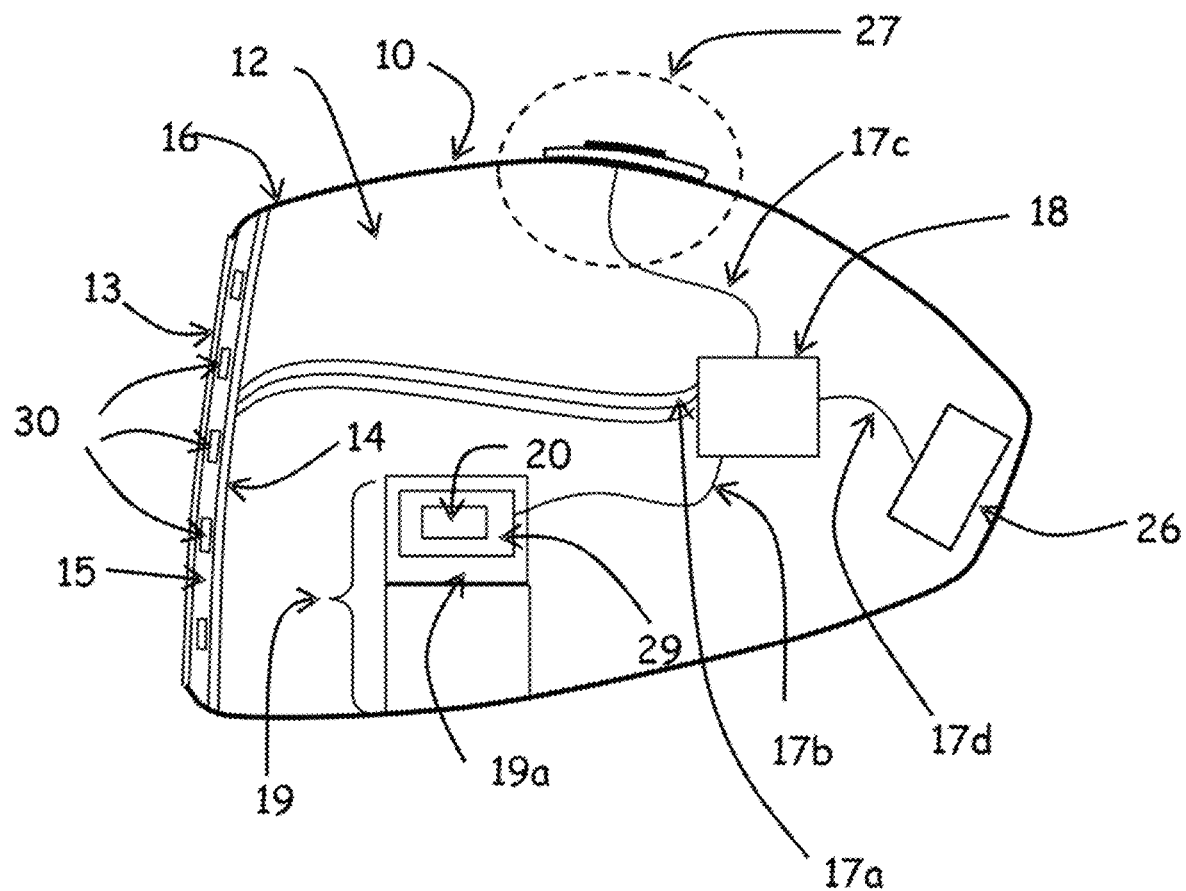
FIG. 3 is a cross sectional view of the club head system showing the clubface assembly, antenna assembly, three dimensional acceleration measurement assembly, electronics assembly and energy storage assembly with electrical connections between said assemblies.

FIG. 3, shows a cross section view of the integrated electronics system golf club head with assemblies related to measurement and wireless communications represented. The three orthogonal axes acceleration measurement assembly comprises a three dimensional acceleration g-force sensor 20 or combination of one and two dimensional g-force sensors to give three dimensional measurement capabilities that are attached to a small printed circuit board 29. The printed circuit board 29 is electrically connected with electronics assembly 18 with a flex ribbon 17b. The acceleration measurement assembly is mounted in a predetermined spatial relationship to the club head shell structure. The preferred embodiment defines the predetermined spatial relationship to the club head shell structure to be the center of gravity of the overall integrated electronics system golf club head. The mounting method and structure of mounting mechanism is defined later in the final design optimization process. An example of a resultant possible mounting from final design optimization process is described for clarity purposes. In one embodiment the small printed circuit board 29 will be attached with a durable adhesive to a metallic or non-metallic rigid protrusion 19 attached to the club head 10 shell inner surface either by adhesive, weld, fastener, or other well-known connection means. The protrusion 19 extending to the spatial location that is predefined location for the sensor circuit board 29 assembly. The surface areas 19a of the protrusion 19 on which the sensor's printed circuit board 29 is mounted has a defined orientation within the club head to align the acceleration measurement axes with the pre-defined reference axes of the club head.

The electronics assembly 18 is located at a predetermined location within club head shell 10 cavity. The predetermined location and mounting method are defined later in the final design and optimization process. The electronics assembly 18 is electrically connected with flexible transmission line or coax cable 17c to antenna elements and object(s) assembly 27 that is located at a predetermined location on club head 10 shell outer surface. Further electronics assembly 18 is electrically connected with wire(s) 17d to energy source assembly 26 that is located at a predetermined location within club head 10 shell. All assemblies located in the club head 10 shell cavity may be mounted in their individual predefined locations with mounting structures attached to club head 10 shell cavity inner surface similar to structure 19 or may be held in their predetermined location within a light weight molded form body that that is spatially fixed in club head 10 shell cavity and provides spatial support for each assembly relative to club head 10 shell structure. The light weight molded form body may be a durable light weight foam material or a light weight plastic molded structure. The electronics assembly 18 provide circuitry for functions of: sensor data capture, wireless communications and RSSI measurements from signals received through antenna assembly 27.

All of the assemblies including: club face assembly, electronics assembly 18, acceleration g-force sensors assembly 20, antenna system assembly 27 and energy source assembly 26 each have a predetermined weight that is defined in the design optimization process of each separate assembly. The assemblies are combined and assembled in the final design optimization process where final individual predetermined location of assemblies and club head shell wall thickness profiles are defined to further define the desired weight and mass distribution of overall club head system. This includes the optimized club head shell structure that is part of the antenna system assembly to have a total weight substantially similar to that of a regulation golf club head of similar type that is recognized to have good performance. In addition, the predetermined locations of the antenna components sub-assembly(ies) and electronics assembly and the acceleration g-force sensor assembly and the energy source assembly in conjunction with club face assembly are optimized so that the center of gravity of the integrated electrons system golf club head is substantially similar to that of a regulation golf club head of similar type.

In general, mobile electronic devices that depend on a battery or other energy storage device(s) and that utilize radio wave wireless communications are challenged with size, weight and operational time duration. The power consumption efficiency of an electronics wireless system is heavily depend the ability to efficiently convert electronic signals generated from within the physical electronics to propagating radio waves with an intended radiation pattern. The power efficiency of the conversion process is typically dominated by the characteristics of the physical antenna elements structures that further control the electrical port impedance of the antenna system operating at a predetermined frequency or frequency band.

The integrated electronics system golf club head antenna system utilizes the electrical properties and defines physical surface shape properties of the club head shell itself as part of the antenna system. The components of the antenna system include at least two or more electrically conducting elements and may include at least one or more electrically non-conducting objects. The preferred embodiment antenna system of this invention utilizes and defines the club head shell and surface structure as one of the electrically conducting elements. The design optimization process for the antenna system defines the shape(s) size(s) and material properties of all components of the antenna system. All components of the antenna system are also in a predetermined fixed spatial relationship with one another. The design optimization process of the antenna system defines all components of the antenna system and specifically defines a club head shell outer surface structure that in combination with other antenna components provides desired radiation patterns and desired electrical input port impedance to optimize the power efficiency of the system that further enables a smaller and lighter energy storage device. In addition, the wall thickness of the club head 10 shell are further optimized in later described processes to provide structural support for the overall assembled club head to perform as a golf club head with substantially similar physical performance criteria as a regulation golf club head of similar type.

The integrated club head antenna system may be implemented with one or a combination of techniques that launch radio wave and influence radiation patterns. The first technique employs the club head as a quasi-ground plane or ground object reflector that is in a fixed spatial relationship with other electrically conducting element or elements. The radiating element such as a wire operating in the presence of a ground object produces two rays at each observation angle, a direct ray from the radiating element and a second ray due to the refection from the ground object affecting radiation pattern. The second technique employs patch antenna theory that requires a ground plane or quasi ground plane that in combination with a conductive patch or sheet type electrically conductive element creates a trapped wave resonant cavity. The resonant structure facilitates electric field fringe effects to generate electromagnetic radiating apertures. The required quasi ground plane or quasi-ground object is implemented with the conductive club head shell surface. In both techniques, the club head shell is used as an electrically conductive element of the antenna system and the structure of the electrically conductive club head shell outer surface is an integral part of the overall antenna system design and affects performance with regards to electrical port impedance and the radiation pattern and reception gain performance of the antenna system structure as a whole.

The preferred embodiment of the antenna system comprise at least, a first electrically conducting element that is a golf club head shell made of electrically conducting material and at least one additional electrically conducting element and may have at least one electrically non-conducting object.

Figure 4:
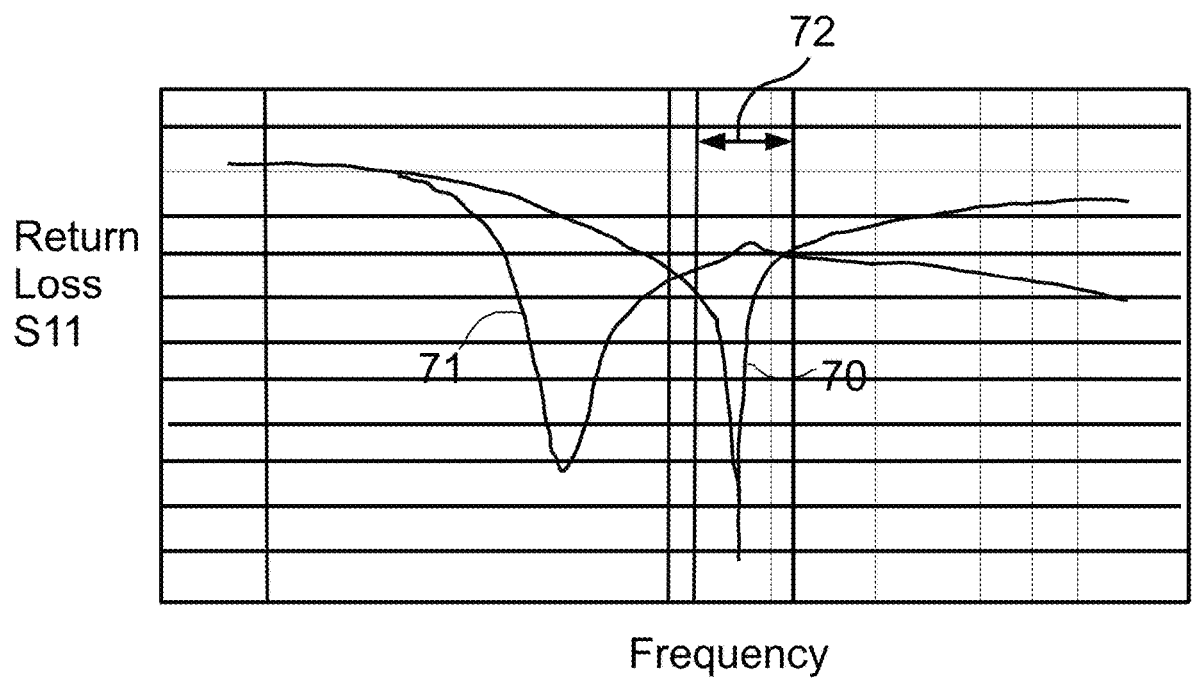
FIG. 4 is a graph showing two return loss measurements (S11) of a single antenna, demonstrating the detuning effect on electrical port impedance when antenna is placed near an electrical conducting object

The benefits of the integrated club head antenna system are multifaceted, namely fewer parts, lighter weight and better performance as compared to using an off the shelf antenna(s) that is/are not designed to function in the constant presence of a metal object namely the club head. For an off the shelf generic antenna designed for a free space environment, both port impedance and radiation pattern are also strongly influenced by all electrically conducting objects in their near environment. The result of using an off the shelf antenna in the near presence to a golf club head has the effect of detuning the electrical port impedance creating an impedance mismatch between the circuitry electrical output port that is driving the electrical input port of the antenna system. As shown in FIG. 4, an electrical port impedance change of an antenna system is demonstrated with two different return loss (S11) measurements on a network analyzer. The first S11 curve 70 shows an antenna return loss with the intended impedance match between the 50 ohm network analyzer port and the intended 50 ohm impedance of the electrical port of the antenna for the intended frequency band 72 in a relatively free space environment. The second S11 curve 71 is measured with the antenna system in the presence of a large metal object in near proximity of the same antenna. The S11 curve 71 shows the significant impedance mismatch described with return loss that is now taking place in the intended frequency band 72 between the 50 ohm port of the network analyzer and the antenna system port. In summary, the presence of a metal object near an antenna system significantly alters the input impedance of the electrical port of the antenna and alters the overall radiation pattern of the combination of antenna and reflecting object.

All of the variations of the invention assembly antenna system comprise at least, a first electrically conducting element that is a golf club head shell made of electrically conducting material and at least one additional electrically conducting element and may have at least one electrically non-conducting object.

Figure 5:
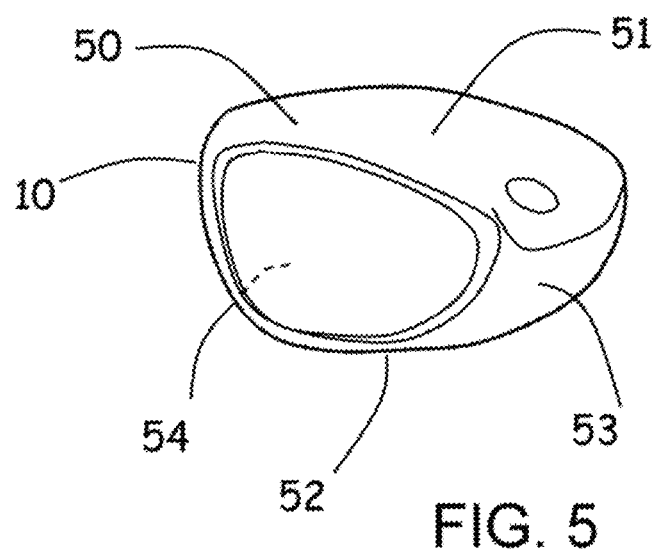
FIGS. 5, 5A and 5B show components of the antenna assembly that include FIG. 5 the club head shell with electrically conductive outer surface, FIG. 5A example types of some possible additional conductive elements and FIG. 5B example types of some possible electrically non-conductive objects

As shown in FIG. 5 the first conducting element of the antenna system is the electrically conductive club head 10 shell that has an outer surface 50 with club face assembly included. The outer conductive surface 50 comprises regional surfaces that include the top surface 51 and bottom surface 52 and side surfaces that include a toe side surface 54 and heal side surface 53. The shape and contour of one or more of the outer surface components may be modified to optimize the antenna system performance.

Figure 5A:
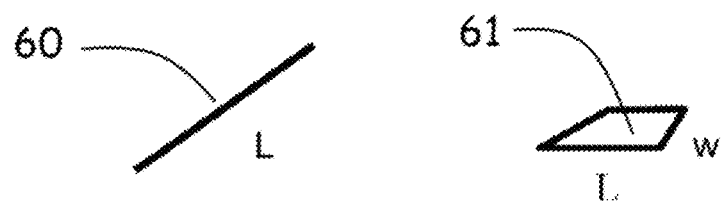

As shown in FIG. 5A the second or other or additional electrical conducting element(s) of the antenna system can be any predefined shape(s). Some examples of additional electrical conducting elements are a wire 60 of a predefined length L and predefined form factor or a metal sheet in a plane 61 form factor or domed shape (not shown) form factor or any other surface form factor of predefined descriptive dimension such as length and width and other dimensions describing shape or a combination thereof.

Figure 5B:
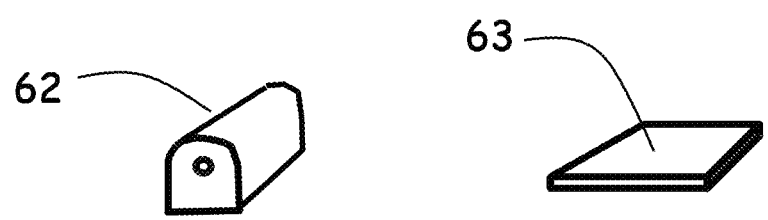

As shown in FIG. 5B a least one or more electrically non-conducting object(s) may each be any predefined shape and size with a predefined dielectric property. The predefined shape(s) and the predefined dielectric properties are defined in the design optimization process for the antenna system. The function of the electrical non-conducting object is to physically hold the additional electrical conducting elements in a predetermined orientation to a predefined surface structure of the electrically conductive club head shell outer surface and affect the electric field in a predetermined way of the additional electrically conducting element. An exemplary electrically non-conducting object 62 may be a shape that is adapted to attach to a predetermined location on the club head shell outer surface 50 and further supports an additional electrically conducting element such as wire 60 at a predetermined spatial relationship to the club head shell and electrically non-conducting object 62 has the material dielectric property similar to air. Another exemplary electrically non-conducting object 63 is a sheet of material that may be a plane type shape with a predetermined length, width and thickness and further a predetermined dielectric constant that is substantially higher than that of air and that attaches to the club head shell 10 outer surface 50 at a predetermined location and is further attached to the metal plane 61 with metal plane 61 located at a predefined location on the surface of electrically non-conducting object 63.

Figure 6:
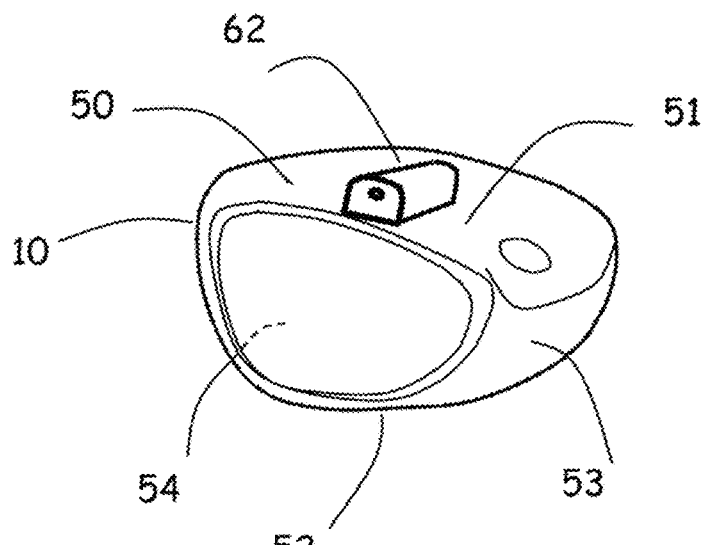
FIG. 6 shows an embodiment of an antenna system with a first electrically conducting element that is the club head shell outer surface attached to an electrically non-conducting object that is further attach to and enclosing to a second electrically conducting element of a wire type.
Figure 6A:
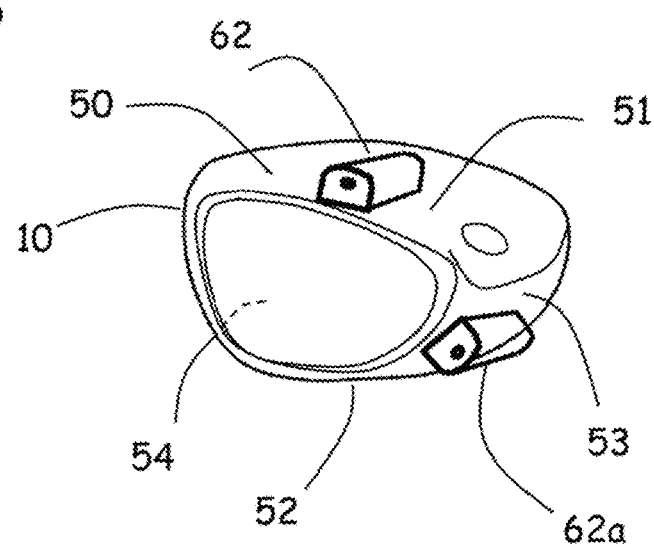
FIG. 6A shows another embodiment of an antenna system with a first electrically conducting element that is the club head shell outer surface attached to two separate electrically non-conducting objects that each further attach individually and enclosing to two separate electrically conducting elements, both of a wire type.

FIG. 6 and FIG. 6A show antenna systems that utilize the conducting club head 10 shell as ground reflector for an antenna system. FIG. 6 shows an exemplary antenna system configurations comprises a club head 10 shell outer surface 50 that is connected to an electrically non-conducting object 62 in a predefined location on club head 10 shell outer surface 50, that further attaches to and supports a second electrically conductive element (not shown, but within non conducting object 62) that is held in a predetermined spatial relationship to club head 10 shell outer surface 50. The electrical port of antenna system is defined by two electrical connections points (not shown), the first electrical connection point is on the interior surface of the electrically conductive club head 10 shell and the second connection point is a location on the second or additional electrically conducting element (not shown, but within non conducting object 62) that is fed through an insulating pass through (not shown) of the club head 10 shell. The club head shell surface structure and all predetermine or predefined dimension and locations and spatial relationships of all electrically conducting elements and electrically non conducting object are defined to optimize the antenna system electrical port impedance characteristics for a predefined frequency band and the antenna system radiation pattern for desired characteristics.

As shown in FIG. 6A another exemplary antenna system configuration comprises the club head 10 shell with two separate electrically non-conducting object 62 and 62a, each with an individual predetermined size and shape factors and each attached at a separate predetermine location on club head 10 shell outer surface 50. Further each electrically non-conducting object further supports separate additional electrically conducting elements (element not show but each within respective electrically non-conducting objects) each with an individual predetermined fixed spatial relationship to club head 10 shell outer surface 50. The electrical port of the antenna system is defined by two electrical connection points. The first connection point is on the interior surface of the electrically conductive club head 10 shell and the second electrical connection point is a single point that is electrically connected both second and third electrically conducting additional elements (not shown, but within respective electrically non-conducting objects 61 and 62a). Further each individual electrically conducting additional element is fed through an individual insulating pass through in the club head 10 shell and the electrical connections between the two additional electrically conducting elements is made in the interior cavity of the club head shell (not shown) defining the second electrical connection point of the antenna system electrical port. The club head shell surface structure and all predetermine dimension and locations of all electrically conducting elements and electrically non conducting objects are defined to optimize the antenna system electrical port impedance characteristics for a predefined frequency band and the antenna system radiation pattern for desired characteristics.

Figure 7B:
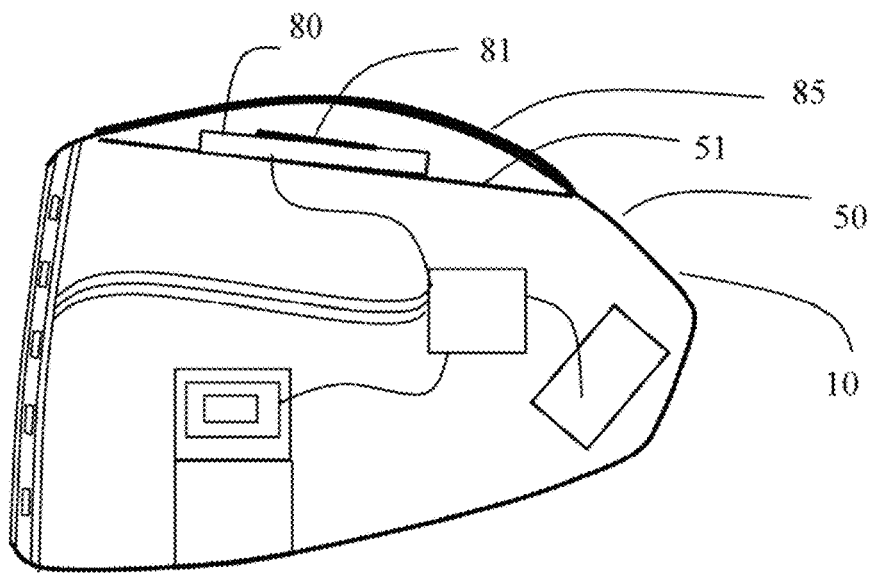
FIG. 7B is a cross-sectional view of club head utilizing the antenna system of FIG. 7 showing another electrically non-conducting RF transparent structure attached to club head shell outer surface and covering antennas system components for improved aerodynamic performance.
Figure 7A:
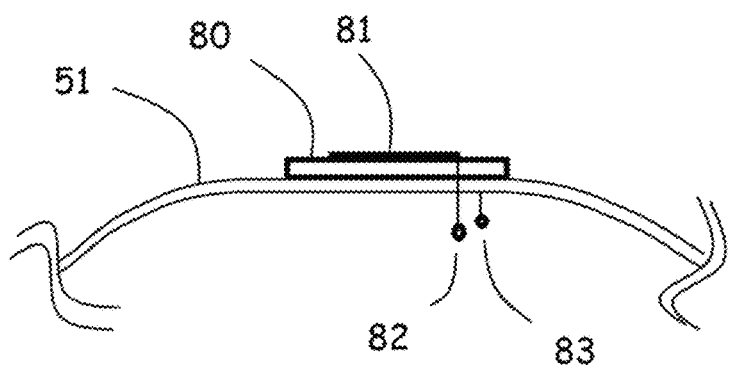
FIG. 7A is a partially exploded cross sectional view of the antenna system of FIG. 7 showing the two electrical contact points that define the antenna system electrical port.
Figure 7:
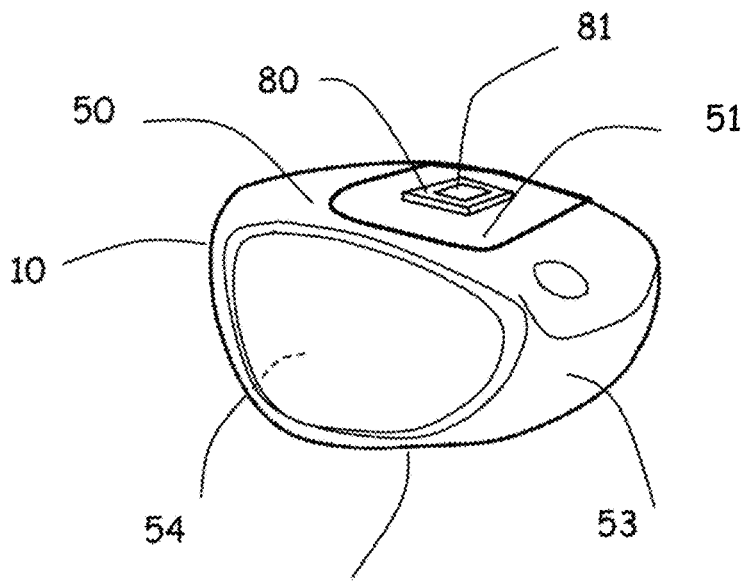
FIG. 7 shows an exemplary embodiment of an antenna system configured to utilize fringe e-field effects to create radiating apertures similar to patch type antennas. The antenna system comprises a first electrically conducting element that is the club head shell outer surface that attached to a first electrically non-conducting object that is a dielectric sheet that is further attached to a second electrically conducting element that is a metal sheet.

As shown in FIG. 7 and FIG. 7A another embodiment of the antenna system is based on a patch antenna structure. As shown in FIG. 7 an exemplary antenna system comprises a first electrically conducting element that is the club head 10 shell that has a top surface 51 that is adapted to be flat in a given surface area. An electrically non conducting object 80 is attached to the top surface 51 at a predetermined location and orientation to top surface 51. Further electrically non-conducting object 80 has a predetermined size and shape and material properties and in this example the object 80 is a material with a predetermined dielectric property value. Further electrically non-conducting object 80 has attached to it at a predetermined location, an additional electrically conducting element 81 with a predetermined size and shape. As shown in FIG. 7A a cross sectional expanded view of this example antenna system shows the club head 10 shell top surface 51 attached to electrically non conducting object 80 further attached to the additional electrically conducting element 81. Further FIG. 7A shows the antenna system electrical port connection points 82 and 83. The electrical port connection point 82 is electrically connected with wire or transmission line that passes through an electrically insulated pass-through in club head 10 shell wall and another pass-through in non-conducting object 80 to additional electrically conducting element 81 where wire or transmission line is electrically connected to additional electrically conducting element 81. The electrical port connection point 83 is electrically connected to electrically conductive club head 10 shell directly or with short wire.

The club head 10 shell outer surface 50 structure and all predetermine dimension, shapes and locations of all electrically conducting elements and electrically non-conducting objects are defined to optimize the antenna system electrical port impedance for desired characteristics for a predefined frequency band and the antenna system radiation pattern for desired characteristics.

Another antenna system example comprises a first conducting element that is the electrically conducting club head 10 shell, and at least two more additional electrically conducting elements comprising at least one that is adapted for patched type structure(s) and at least one adapted for a wire type structure(s) of individual predetermined size and shape. Further the antenna system may have electrically non-conducting objects of predetermined size and shape associated with each of the additional conducting elements. The club head shell 10 outer surface 50 structure and all predetermine dimension, shapes and locations of all additional electrically conducting elements and electrically non-conducting objects are defined to optimize the antenna system electrical port impedance for desired characteristics for a predefined frequency band and the antenna system radiation pattern for desired characteristics.

Another embodiment antenna system has more than one electrical port where each port has two electrical contact points. This antenna system comprises at least three electrically conducting elements and first electrically conducting element is the golf club head 10 shell and at least two addition electrically conducting elements. The first electrical port comprises two electrical contact points and first electrical contact point is electrically connected the first electrically conducting element club head and second electrical contact point is connected to one or more additional conducting element(s) but not all additional conducting elements. The second or additional electrical ports(s) each have two electrical contact points and the first electrical contact point is electrically connected to the first electrically conducting element the club head and the second electrical contact point is electrical connected to at least one additional electrically conducting element that is not electrically connected to the electrical contact point of first port or other additional port(s). The benefit of an integrated electronics system golf club head with multiple antenna ports is the system can then support full duplex operation with constant receive and transmit taking place simultaneously on two different frequencies or two different frequency bands. In addition an antenna system with multiple ports could support MIMO (Multiple Input Multiple Output) wireless communication structures supporting much higher communication data rates.

All attachments required between electrically conducting elements and electrically non-conductive objects may be accomplished with an electrical conductive or non-conductive adhesive or fasteners.

All of the antenna system embodiments may have additional electrical non-conducting structures that attached to the club head 10 shell external surface that further cover antenna system components to provide a smooth surface of overall club head structure to provide a similar aerodynamic structure to that of a similar golf club head type. The material properties of the aerodynamic enhancement structures include radio frequency transparency with regards to radio wave signals. In other words do not affect radio waves as radio waves pass through the aerodynamic enhancement structures.

FIG. 7B shows a cross sectional view example of club head 10 with a patch configuration antenna system assembly embodiment with an aerodynamic enhancement structure 85. Aerodynamic enhancement structure 85 attaches to club head 10 shell outer surface 50 covering modified top surface area 51 and electrically conducting element 81 and electrically non-conducting object 80. Aerodynamic enhancement structure 85 may be attached to club head 10 outer surface 50 with a non-conducting adhesive or fastener. The benefit of the aerodynamic enhancement structure is that it allows greater manipulation of the club head 10 shell outer surface 50 structure for more flexibility in antenna system design, while providing the aerodynamic properties of club head overall outer surface structure to be substantially similar to that of a high performance club head of similar type.

As previously recited, the antenna system has numerous control variables that affect the electrical performance of the total electronics system and the structural physical performance of the club head. To define the predetermined values for all of the control variables in the antenna system to meet electrical and physical requirements, a design optimization process is used. A means of antenna system design optimization comprises a process with the steps of:

1. Define the club head type for the system.
2. Define the frequency band of operation for the antenna system
3. Define the desired radiation pattern of the antenna system
4. Define the antenna system desired electrical port impedance characteristic based the predefined electronics drive port electrical impedance characteristic in regards to the predefined frequency band of operation.
5. Define an estimated number of additional electrically conducting elements and what club head surface areas will be utilized for desired radiation pattern coverage around club head.
6. If any of the additional electrically conductive elements are intended for patch structures define an estimate of the property of dielectric constant for the electrically non-conducting object based on frequency band and general surface area available for selected club head surface area.
7. Calculate through know estimation equations an initial estimates of size, shape and dimensions of addition electrically conducting elements of the wire type, and assume free space environment based on predefined frequency of operation that defines related wavelengths of operation. Standard or non-standard conducting element structures may be used. Typical and standard structures include but are not limited to wire type structures such as short dipole, ¼wave dipole, half wave dipole, helix, L, F etc. Non-standard structures can also be used, however, estimate calculation equations will need to be derived independently based on Maxwell equations.
8. Calculate through know estimation equations based on defined frequency band the initial estimates of size, shape and dimensions of addition electrically conducting element(s) of the patch type and size, shape and dimensions of electrically non-conducting object(s), in conjunction with a predefined dielectric property of the associated electrically non-conducting object(s). Assume an ideal planer ground connected to the electrically non-conducting object and assume free space environment based on predefined frequency of operation that defines related wavelengths of operation. Standard or non-standard conducting element structures may be used. Typical and standard structures include but are not limited to patch or leaky transmission line type structures on an ideal ground planer surface such as layered and multilayered structures with a variety of coupling feed types. These estimates will be a starting point for further considering non-planer structures and a non-ideal ground planes such as the club head shell.
9. Using estimated size and shape and location for club head structure and all additional electrically conducting elements and all electrically non-conducting objects build a model in ANSYS HFSS 3d full wave electromagnetic field solver.
10. For an antenna system that use wire type additional electrically conducting elements only:
    a. Adjust spatial location and orientation of addition electrical conducting elements in relation to club head shell to achieve desired radiation pattern.
    b. Adjust club head shell outer surface area region contours related to each additional electrically conducting elements to further tune radiation pattern.
    c. Adjust size, shape and dimensions of previous estimates (Step 6) of additional electrically conducting elements to achieve a desired input port impedance characteristic in the define frequency band.
    d. Repeat steps 9a through 9b and further adjust end results of step 9c to retune radiation pattern and input port impedance characteristics.
    e. Define electrically non-conducting object structures including size and shape for attachment to defined predetermined club head shell outer surface area structure to further attach additional electrically conductive elements of defined predetermined size and shape in defined predetermined spatial reference to club head shell outer surface area region.
11. For an antenna system that use patch type additional electrically conducting elements only:
    a. Adjust spatial location and orientation addition electrical conducting elements with associated fixed relation electrically non-conducting objects in relation to club head shell to achieve desired radiation pattern.
    b. Adjust club head shell outer surface area region contours related to each additional electrically conducting elements to further tune radiation pattern.
    c. Adjust size, shape and dimensions of previous estimates (Step 7) of additional electrically conducting elements to achieve a desired input port impedance characteristic in the define frequency band.
    d. Repeat steps 10a through 10b and further adjust end results of step 10c to retune radiation pattern and input port impedance characteristics.
12. For Antenna system that utilize both wire type and patch type additional conducting elements:
    a. Conduct steps 9a and 10a
    b. Conduct steps 9b and 10b
    c. Conduct steps 9c and 10c
    d. Conduct steps 9d and 10d
    e. Conduct step 9e
13. Evaluate assembled antenna system including all electrically conducting elements and electrically non-conducting based on electrical performance as an antenna with port impedance and radiation pattern performance criteria and physical properties as a golf club head with aerodynamics as a criteria. If aerodynamics of club head outer surface structure not satisfactory implement aerodynamic enhancement structures.
14. Define weight of antenna assembly with all components including aerodynamic enhancement structure (if used). At this point the electrically conducting club head shell has zero wall thickness and therefore zero weight. The distribution of club head shell wall thickness will be defined later in the overall design optimization process of when all assemblies are put together.

Figure 8A:
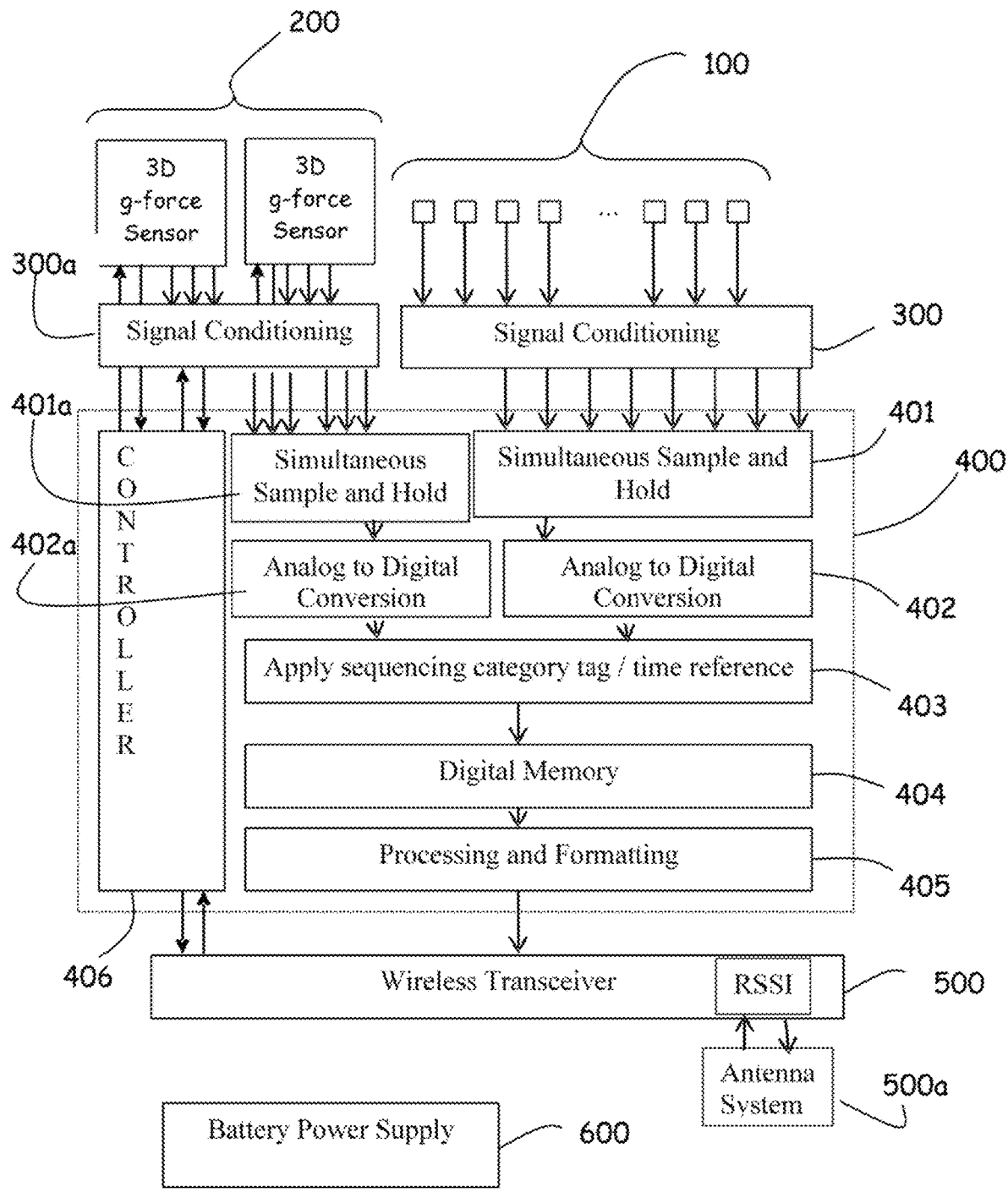
FIG. 8A is a block diagram of sensors and electronic processing functions and electronic support functions of integrated golf club head of the present invention.

As shown in FIG. 8A, the electronics assembly is the central processing and electrical connection hub for all other assemblies with electronic components. The sensor categories, three dimensional g-force sensor(s) 200 and the pressure force sensors 100 are electrically connected to electronics that capture the time varying electrical signals of all of the sensors. Additionally RSSI measurements are made by RSSI circuitry in the wireless transceiver 500 and synchronized with three dimensional g-force sensor 200 measurements. The electrical signals may or may not use signal conditioning 300 and or 300a before they are input to sample and hold functions 401 and 401a. The sample and hold functions 401 or 401a samples all sensor(s) individually in a sensor category simultaneously at a rate defined for each sensor category. The sampling rate of each sensor category may be the same between sensor categories or may be different between sensor categories. Further the sampling rate of an individual sensor category may be constant or may be dynamically change during the golf swing based on logic triggers in the controller 406 associated with monitoring sensor levels of either one or both sensor categories. During the time duration that individual sample and hold stores sensor amplitude value in each of the sensor categories then analog to digital conversion function(s) 402 and or 402a takes each sample value and converts it to a digital representation. All of the digital samples for each sensor category are associated with that single sample time on a measurement time line of acquisition in "the apply sequencing sensor category tag and time reference" function 403 and then are moved into digital memory 404. The sampling rate for each sensor category of the simultaneous sample and hold function 401 and 401a are at, or faster than, the "Nyquist rate" determined by the highest pertinent frequency component associated with each sensor category. After all data has been loaded into memory storage 404 from a given golfer's swing, additional swing data can be captured and stored or the data is further processed and formatted 405 for transfer to a user interface function. All of the functions listed are coordinated by a controller function 406, which may be integrated together with other functions 400 such as a sophisticated PIC (Periphery Interface Control) module with DSP (Digital Signal Processing) functionality. In a preferred embodiment, the signal is processed and formatted 405 to be applied to a wireless transceiver 500 function. The wireless transceiver function includes electronic circuitry that provides electronic signals to an electrical drive port that is further connected to the antenna system 500a electrical input port(s). The antenna system emits and receives radio frequency waves for transfer of information between a remote user interface such as a laptop computer with wireless transceiver capabilities. Further when receiving radio wave signals the transceiver is measuring the receiver signal strength of those signals. All of the functions in FIG. 8A that require electrical power to function are supplied by an energy source such as battery power supply 600 that is detachable from the integrated golf club or rechargeable if it is implemented as a permanent component of the golf club head.

The electronics controller 406 dynamically organizes and controls the electrical sequencing and processing of the signals based on a fixed startup sequence and then triggers. When the integrated electronic system golf club head is initially turned on, the controller starts capturing and monitoring the g-force sensor(s) 20 measurement axes values form sensors 200 and measuring receiver signal strength at the antenna system 501a. After startup the controller 406 comprises logic implemented with firmware residing and executing in controller 406 that defines a trigger events that may indicate for example weather the club head is moving or still or what portion of the swing is taking place based g-force sensor data. Further more complex triggers may be defined for triggers based on a combination of g-force sensor data and impact sensor data. Based on a predefined trigger events occurring the controller instructs electronic circuitry to individually or in any combination start or stop or adjust any operational function or combination of functions for example: memory storage of a given sensors category, wireless transmission, sample rate for individual sensor categories or any other electronic function affecting system operation and or mode of operation. The benefits of the of a system based on predefined logic triggers based on sensor inputs is the ability to optimize the state of operation of electronic function when needed to acquire the minimal amount of data to fully describe the desired swing characteristics and further reducing electronic function operations when not needed to minimize overall energy consumption. The lower overall energy consumption of the electronics allows for smaller lighter energy source or energy storage supply which contributes to the overall design flexibility of achieving an integrated electronics system golf club head with weight, center of gravity and physical structural performance similar to that of a regulation golf club head of similar type.

Figure 8B:
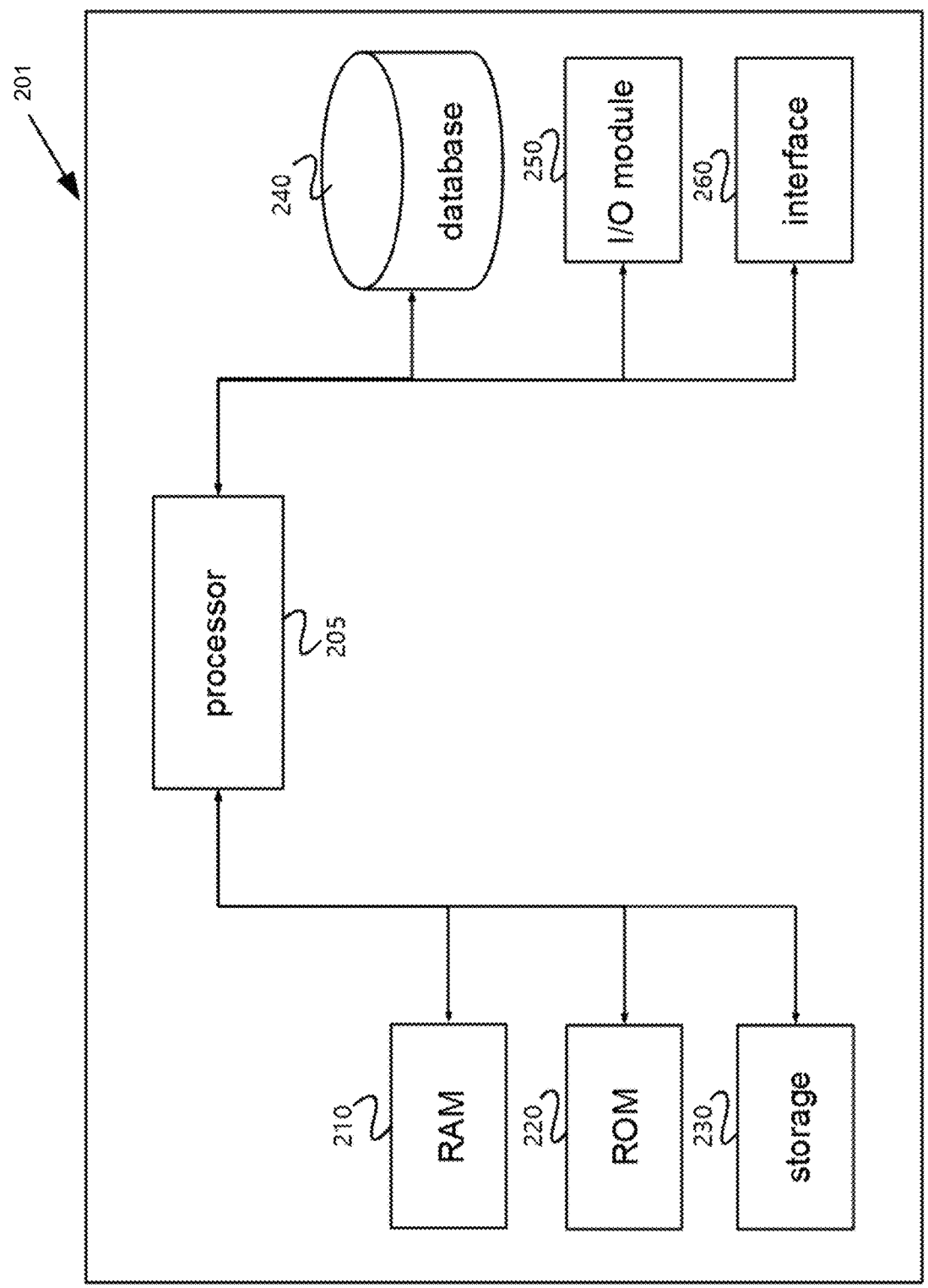
FIG. 8B is an exemplary diagram of a computer system for use in an integrated golf club head, in accordance with an embodiment.

FIG. 8B depicts an exemplary processor-based computing system 201 representative of the type of computing system that may be present in or used within the golf club head or at a receiver that receives swing and/or impact data from the golf club or attached module. The computing system 201 is exemplary only and does not exclude the possibility of another processor- or controller-based system being used in or with one of the aforementioned components.

In one aspect, system 201 may include one or more hardware and/or software components configured to execute software programs, such as software for storing, processing, and analyzing data. For example, system 201 may include one or more hardware components such as, for example, processor 205, a random access memory (RAM) module 210, a read-only memory (ROM) module 220, a storage system 230, a database 240, one or more input/output (I/O) modules 250, and an interface module 260. Alternatively and/or additionally, system 201 may include one or more software components such as, for example, a non-transitory computer-readable medium including computer-executable instructions for performing methods consistent with certain disclosed embodiments. It is contemplated that one or more of the hardware components listed above may be implemented using software. For example, storage 230 may act as digital memory that includes a software partition associated with one or more other hardware components of system 201. System 201 may include additional, fewer, and/or different components than those listed above. It is understood that the components listed above are exemplary only and not intended to be limiting.

Processor 205 may include one or more processors, each configured to execute instructions and process data to perform one or more functions associated with system 201. The term "processor," as generally used herein, refers to any logic processing unit, such as one or more central processing units (CPUs), digital signal processors (DSPs), application specific integrated circuits (ASICs), field programmable gate arrays (FPGAs), and similar devices, such as a controller. As illustrated in FIG. 2A, processor 205 may be communicatively coupled to RAM 210, ROM 220, storage 230, database 240, I/O module 250, and interface module 260. Processor 205 may be configured to execute sequences of computer program instructions to perform various processes, which will be described in detail below. The computer program instructions may be loaded into RAM for execution by processor 205.

RAM 210 and ROM 220 may each include one or more devices for storing information associated with an operation of system 201 and/or processor 205. For example, ROM 220 may include a memory device configured to access and store information associated with system 201, including information for identifying, initializing, and monitoring the operation of one or more components and subsystems of system 201. RAM 210 may include a memory device for storing data associated with one or more operations of processor 205. For example, ROM 220 may load instructions into RAM 210 for execution by processor 205.

Storage 230 may include any type of storage device configured to store information that processor 205 may need to perform processes consistent with the disclosed embodiments.

Database 240 may include one or more software and/or hardware components that cooperate to store, organize, sort, filter, and/or arrange data used by system 201 and/or processor 205. For example, database 240 may include information to that tracks swing and/or impact data based on embodiments herein. Alternatively, database 240 may store additional and/or different information. Database 240 may also contain a plurality of databases that are communicatively coupled to one another and/or processor 205, of may connect to further database over the network.

I/O module 250 may include one or more components configured to communicate information with a user associated with system 201. For example, I/O module 250 may include a console with an integrated keyboard and mouse to allow a user to input parameters associated with system 201, such as the identification of the golfer to independently track different users of the same smart golf club. I/O module 250 may also include a display including a graphical user interface (GUI) for outputting information on a monitor. I/O module 250 may also include peripheral devices such as, for example, a printer for printing information associated with system 201, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 260 may include one or more components configured to transmit and receive data via a communication network, such as the Internet, a local area network, a workstation peer-to-peer network, a direct link network, a wireless network, or any other suitable communication platform, such as Bluetooth. For example, interface 260 may include one or more modulators, demodulators, multiplexers, demultiplexers, network communication devices, wireless devices, antennas, modems, and any other type of device configured to enable data communication via a communication network.

Figure 9:
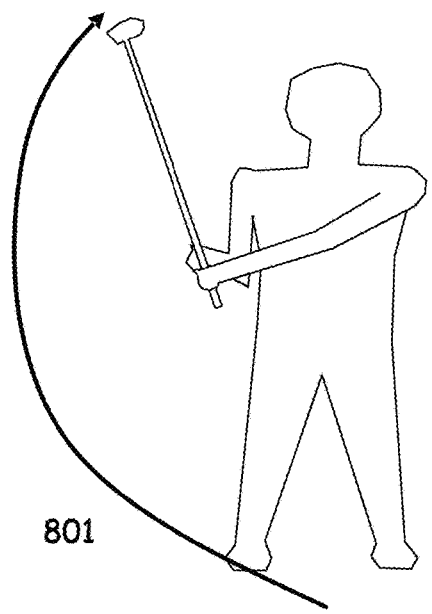
FIGS. 9, 9A, 9B and 9C details a golfer swing time lapse showing associated trigger points that control and alter data capture processing parameters within the electronics of the present invention.
Figure 9A:
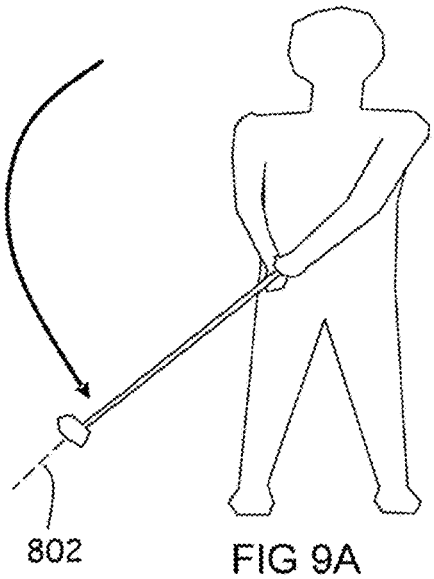
Figure 9B:
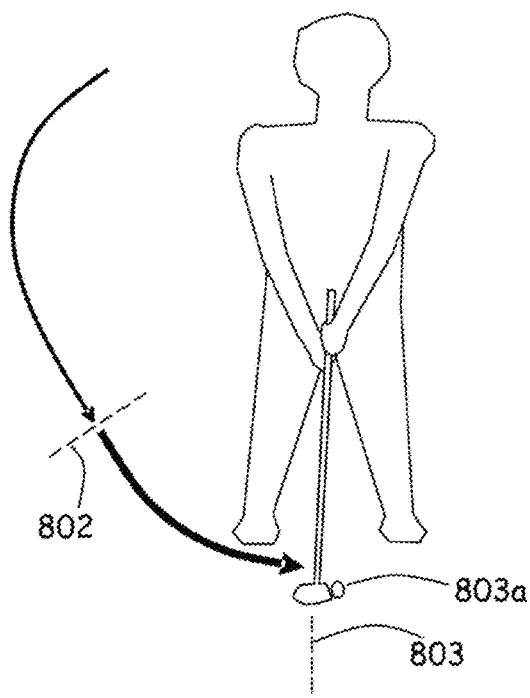
Figure 9C:
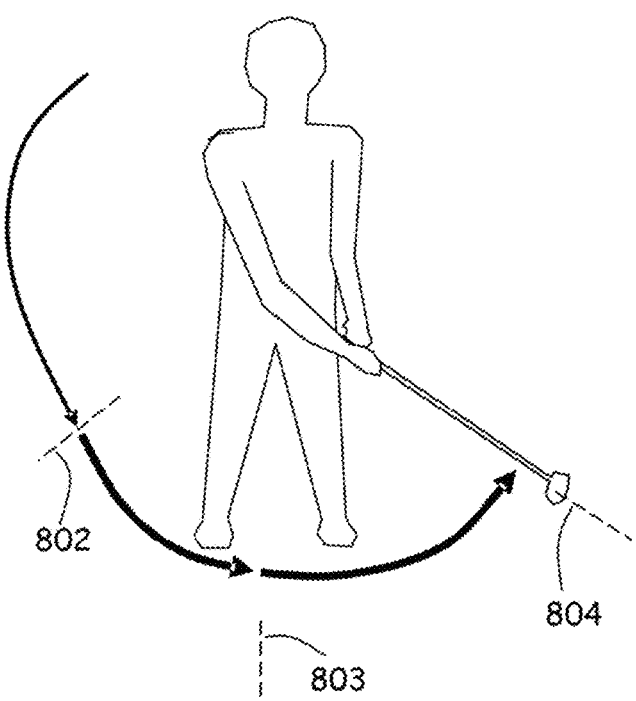

As shown in FIGS. 9, 9A, 9B, and 9C, the progression of a golf swing is shown to provide an example of how triggers may work by modifying electronic functions during the golf swing to provide all required information while reducing overall average energy consumption rate from battery source. This is only an example and numerous other trigger configurations are anticipated and would be obvious to a person of ordinary skill in the art after reviewing this example. FIG. 9 shows the golfer during the backswing 801 and only acceleration g-force sensor measurement are be captured at a predefined sampling rate and stored and transmitted. FIG. 9A shows the progression of the swing and at point 802 a predetermined trigger is invoked. The trigger's logic criteria is based on a combination of acceleration g-force measurements that determines the swing is substantially into the power-stroke and the invoked trigger causes the controller to increase the sampling rate of the g-force acceleration sensors and RSSI and to start or initiate measuring and sampling and storing the impact force sensors at the predetermined rate and further transmitting synchronized time stamped measurements from memory storage of all sensors out of club head wirelessly. FIG. 9B shows further progression of the golf swing and another trigger is invoked at point 803 indicating the club head is making contact with the ball 803*a* based on impact sensor inputs. The invoked trigger that occurs at point 803 causes the controller to start a timer which after a predetermined time duration relating to location at position 804 shown in FIG. 9C shuts off the sampling and capture and storage of impact sensor measurements and further reduces the sampling rate of the acceleration g-force sensors. Further, wireless transmitter continues to transmit both g-force and impact sensor measurements from memory until all impact measurements in memory have been wirelessly transmitted out. Further wireless transceiver continues to transmit only acceleration g-force sensors data. Further and not shown in the figures, if golf club is set down and is not moving another trigger is invoked based on g-force sensor, and the wireless transmitter is shut off until time when movement is detected again invoking another trigger causing the wireless transmitter is turned back on. In this example the acceleration g-force sensor sample rate and the RSSI sample rate are the same, however, in another embodiment the sample rate of the acceleration g-force sensor measurement and the RSSI can be different and controlled independently, as long as the signals are on synchronized single time line.

The electronics assembly comprises input and output electrical connections to all other assemblies. As previously shown in FIG. 3 the other assemblies that have electrical connections to the electronics assembly 18 are: club face assembly impact sensors 30, g-force sensor assembly 29 for orthogonal acceleration measurements, antenna system assembly 27 and energy supply assembly 26. The electronics assembly comprises electronic components, integrated circuits and various electronic connectors assembled on a printed circuit board. The electronics assembly is optimized for minimal weight and volume while providing reliable predefined electronic functionality within an impact and shock environment. The size and weight of the electronics assembly is defined by the total aggregate weight of all pieces included in assembly with attachment vehicles such as solder. The design optimization process for electronic assembly include the steps of:

1. Define swing speed dynamics range for golf population targeted.
2. Define estimates of maximum impact forces that will be experienced by club head when ball club head impact take place.
3. Select electronic components and IC and connectors that provide required electronic functions and that are robust to function under shock estimates defined in step 2.

4. Layout printed circuit board for all electronics components
5. Assemble circuit board with all components, ICs and connectors to define electronics assembly
6. Record the default out port impedance inherent to an off the shelf RF circuitry such as an RF integrated circuit for use in antenna system design.
7. Measure electronics assemble to define size and weight
8. Define firmware code for electronic process and logic triggers to provide required data to describe swing characteristics and minimize overall current power consumption.
9. Define by measurement the average power consumption for a golf swing including all electronic processing functions of assembly including wireless transceiver functions with matched impedance load for intended frequency band.

The energy source assembly comprises components that facilitate the storage and release of energy to operate electronics. The energy source components may comprise various electrical components for enabling and disabling energy or power to electronics, connectors for electrically connecting to all electronics, and physical structure for assembly of all components and physical structure for supporting assembly either internal or external to club head shell cavity. The energy storage cells may be batteries or capacitors or supper capacitors or other component devices or combination of, that can store and release electrical energy. Further, batteries may be of rechargeable or disposable types.

The design optimization process for the energy source assembly focuses defining a design that has minimal weight and volume while providing operation of electronics for predetermined time duration. The energy source assembly design optimization process includes the steps of:
1. Define require time duration of operations such as training session or a round of golf
2. Define total power requirements to operate all electrical power consuming assemblies associated with integrated electronics system golf club head.
3. Define the total energy required to supply power for time duration defined in step 1.
4. Define energy storage cell type and size and or number of energy storage cells required to provide total energy defined in step 3.
5. Define all electrical and physical support components required for energy cell(s) integrations
6. Define assembled energy assembly weight, volume and shape, and mass distribution.

Energy Harvesting Embodiments

Another assembly for purposes of energy harvesting may be included in the integrated electronics system golf club head or another device, and harvest energy from the impact sensor elements generated power signal. The impact sensor elements may be made of piezoelectric materials that do not require a power supply to function. The piezoelectric elements, however, generate and provide an output voltage and current waveform when a force is applied to the elements such as the impact of a golf ball on the club face assembly. A portion of the generated electrical power signal comprising voltage and current from the impact sensor elements may be used to apply charge to an energy storage cell device in a recharging fashion. The portion of power signal extracted from the impact sensor element(s) is done in a ratio format, so the shape of the signal waveform from impact sensor elements applied to the processing electronics is not changed. Further with the ratio of signal amplitude extracted for recharging purposes known, no information carried by signal portion applied to electronics processing is lost.

Although a golf club head is discussed herein as an example, the system may be part of different sports equipment, such as a tennis racquet, in a device unrelated to sports equipment, or in a device that may be attached to sports equipment. The embodiments discussed herein are not limited to golf embodiments, and the golf embodiments are illustrative and exemplary only.

Additionally, although this application may refer to an "impact sensor" or "pressure sensor" for convenience, both may also be used to detect vibrations and/or other force-related parameters in an embodiment. These sensors may include a piezoelectric element, and in one embodiment, the piezoelectric element may include a cantilever structure that can detect vibration. Unless otherwise stated, any structure for sensing pressure or vibrations may be used as a pressure sensor in an embodiment. The vibrations may be detected in addition to one or more force-related parameters that include pressure, linear acceleration, angular acceleration, and torque. These parameters may be detected singularly by a sensor or in combination by the sensor. The power signal output by the piezoelectric element may be an analog signal that is based on the surface charge changes of the piezoelectric element, which in turn result from deformation of the piezoelectric element due to the force-related parameter. The power signal may be utilized by signal processing circuitry to measure the respective force-related parameter. Although "pressure" may be referred to for simplicity and illustration, any one or more of the force-related parameters may be measured by the piezoelectric elements unless stated otherwise. Over time, these force-related parameters may characterize impact or vibration.

In one embodiment, the system may dynamically adjust the ratio of power that is used for processing and the portion that is used to charge the energy storage cell device (and/or any other portions that may be utilized in an embodiment). For example, a processor may dynamically adjust the ratio in controlling how much of the power signal the signal divider sends to the signal processing circuitry versus the energy storage assembly. As used herein "dynamically adjusting the ratio" may include automatically setting one or more variables that control the signal divider functionality, and also may include any other method of automatically adjusting a first amount of the power signal that is sent to energy storage and adjusting a second amount of the power signal that is sent elsewhere. The processor may make a dynamic adjustment based on a pre-programed timeline, which may be invoked by at least one trigger event, such as detecting that acceleration or velocity meet a threshold. In another embodiment, the dynamic adjustment is part of an on-going analysis or decision algorithms based on sensor outputs. The on-going decision analysis (e.g., algorithms) may take into account multiple sequential thresholds being met by a given sensor output within a defined time frame. In an embodiment, the on-going analysis may further include multi-input time-sensitive logic-based triggers based on many sensors inputs simultaneously that provide intelligent feedback and control to the entire electronics functionality. Thus, the processor may change the ratio to split the power signal differently while adapting to user activities, allowing more of the signal to be sent to energy harvesting when impact signal analysis is less important.

In one embodiment, the processor may shift towards more signal processing based on an acceleration and/or velocity threshold being met. For example, if the processor detects that sports equipment, such as a golf club, is being swung then more or all of the power signal may be directed to signal processing. Conversely, after the impact is over, the processor may send more or all of the power signal to the energy storage assembly. In addition, in one embodiment, the splitter may have more than two outputs which all may be automatically adjusted by the processor. For example, the splitter may have a first output coupled to energy storage, a second output coupled to backup capacitor storage, a third output coupled to signal processing, and a fourth output coupled to a light emitting diode. Adjusting the ratio may include changing the amount of power signal sent to any of these outputs.

In one embodiment, signal analysis may cause the processor to adjust the ratio differently for two different periods: (1) impact analysis and (2) vibration analysis. For example, in one embodiment, the duration of club face impact with a ball is approximately 400 micro seconds, but the club may continue to vibrate after impact for an additional period of time, such as several milliseconds (depending on the club head). During the post-impact vibration period, the processor may adjust the ratio such that an increased portion or all of the power signal is harvested for energy storage. This is because, in one embodiment, the vibration characteristics, shapes, and patterns do not need to be analyzed as precisely, and therefore a smaller range of power signal amplitudes may be adequate for the vibration analysis. In another embodiment, the processor may continue to send most or all of the power signal to energy storage until detecting that a swing is taking place, at which point the processor may shift back into an impact detection state, directing more or all of the power signal back to signal analysis circuitry.

Similarly, because less precision may be needed for vibration analysis than impact analysis, the processor may also dynamically slow the sampling rate after 400 micro seconds pass from initial impact. In one embodiment, the Nyquist frequency may be determined based on the frequency band containing the highest pertinent resonant frequencies for the object being monitored, and the sampling rate may adjust downward to the Nyquist rate.

In another embodiment, when the processor reduces the portion of the power signal that is measured by the signal processing circuitry, this may shrink the voltage amplitude of the measured portion of the power signal. Thus, the processor may also apply and/or send an offset variable indicative of the current ratio to the processing circuitry so that amplitude samples taken of the various power signals are normalized in the digital domain. For example, when the processor controls the ratio such that 80% of the power signal is sent to processing circuitry, the processor may also apply a multiplier of 1.25 to normalize the amplitude samples relative to if the full power signal had been sent to the processing circuitry. As another example, if the ratio is dynamically changed so that only 10% of the power signal is sent to the processing circuitry, a multiplier of 10 may be applied to the samples to normalize the values relative to the full power signal. The processor may additionally or alternatively track the ratio or relative amounts of power signal sent down each splitter output in one embodiment. Thus, when the processor dynamically changes the ratio, it may also associate each change with time-aligned data derived from the relative amounts of the power signal.

A device (for example, a club head) may also include multiple pressure sensors in one embodiment, and each of them may be coupled to different signal dividers. The processor may control each signal divider with substantially the same ratio, such that each signal divider will divide the power signals the same way at a given point in time. In another embodiment with multiple pressure sensors, first and second normalizing multipliers may be used on the power signals of first and second pressure sensors, respectively. The first and second normalizing multipliers may be different to compensate for one of the pressure sensors being located closer to the edge of the golf club face than the other. This is because the golf club face may flex more towards the center of the face than toward the edges, which may cause identical pressure sensors to perform differently at the different locations.

Figure 22:
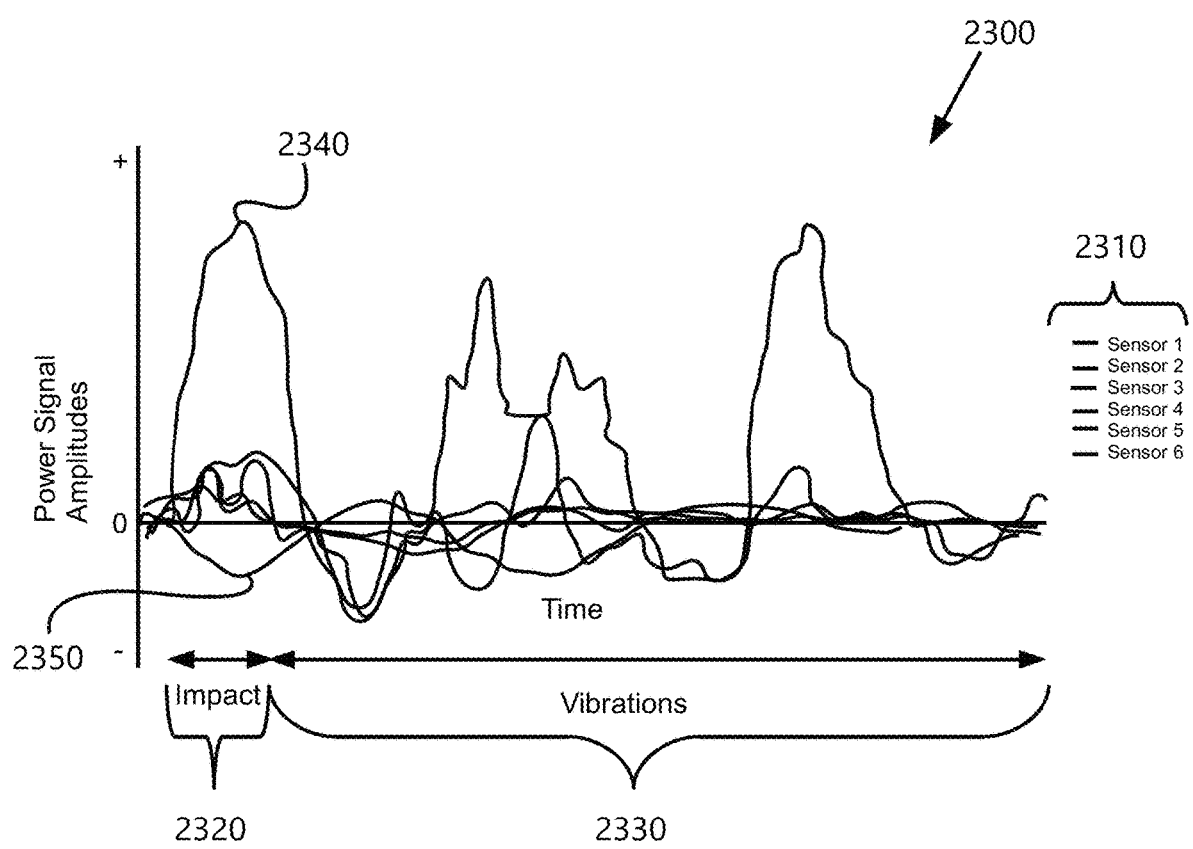
FIG. 22 is an exemplary graph of power signals from piezoelectric elements, in accordance with an embodiment.

Turning to FIG. 22, an example chart 2300 of multiple sensor outputs 2310 are shown, spanning both an impact period 2320 and a vibration period 2330. The x axis in this example represents time. Samples may be taken, for example, simultaneously every 4 microseconds in one embodiment. The y axis in this example represents the amplitudes of the power signals output from each of the six sensors 2310. These amplitudes indicate the amount of pressure on each respective piezoelectric sensor. The amplitude values may be multiplied by a predetermined amount to convert the amplitude samples into standard pressure measurement units, such as pascals (Pa). This calculation may also take into account calibration, which may involve a second multiplier in one embodiment or a sensor specific multiplier that takes into account the ratio in a second embodiment. The pressure measured by each pressure sensor element, in combination with known club face flexibility clamping profile of the club face/club head structure can be used to characterize a time-varying club face surface deformation profile resulting from impact that further can translated into the pressure time location profile exerted by the ball on the club face.

As shown in the example chart 2300 of FIG. 22, a first piezoelectric element may output a first power signal 2340 that has the highest peak amplitude during impact period 2320. This indicates that the ball hit nearest to this first sensor. The other sensors (e.g., piezoelectric elements) also output power signals, which can be analyzed to determine a precise location of impact. A second sensor may output a negative amplitude signal 2350, indicating a negative pressure experienced by the second sensor element, for example, as described with regard to FIGS. 21A and B.

Once the peak at impact is detected and the power amplitude signal begins to fall, the processor may switch into vibration analysis mode for the vibration period 2330. Although, FIG. 22 shows the amplitudes of the full power signals, at this point the processor may change the ratio of power signals such that smaller amplitude power signals are sent to signal processing. However, the larger portion may be sent to energy storage, still leaving the signal processing may be precise enough to analyze various vibration resonances to make further determinations regarding the original impact. In another embodiment, the processor may adjust the ratio to send all of the post-impact power signal to energy storage.

In one embodiment, during the vibration analysis period 2330, resonance patterns are evaluated based on the power signals output from each of the pressure sensors. Different structures may support different vibration resonances, with different dominant resonances. For example, a driver may resonate differently than a putter, both of which resonates differently than a tennis racquet, which in turn resonates differently than a baseball bat. The way the sports equipment resonates may inform about the way ball was struck. For example, if the processor looks at the amplitudes at a predetermined dominant resonance frequency and determines that the amplitudes are above a threshold over a prolonged resonance period, this may indicate that the ball was hit too close to the edge of a club face.

In one embodiment, the impact sensors are at other locations in addition to or instead of at the club face. For example, in one embodiment the impact sensors may be at the shaft or grip of a golf club. In another embodiment, the impact sensors may be built into the hosel and/or side walls of the club head. The vibration resonance patterns and even impact characteristics may be determined from these other locations in an embodiment.

Figure 23:
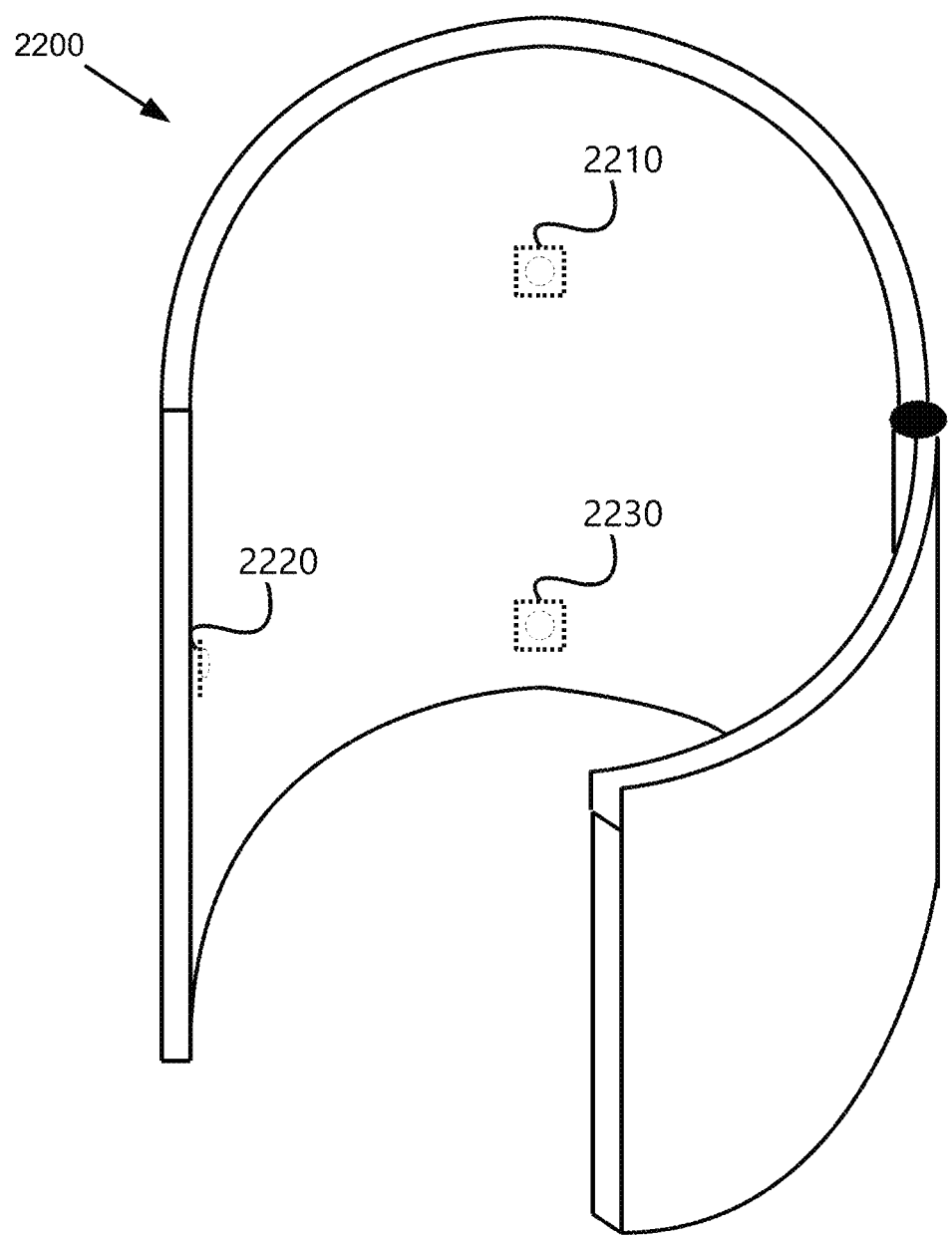
FIG. 23 is an exemplary device for signal processing and recharging, in accordance with an embodiment.

Turning to FIG. 23, a device 2200 having piezoelectric elements 2210 and 2220 is shown. The device 2200 may attach to different sports equipment in an embodiment, or to a different moveable object in another embodiment. For example, the device 2200 may attach to the club head, shaft, or grip of the club in one embodiment. In another embodiment, the device 2200 may attach to, for example, a tennis racket shaft, a baseball bat, a hockey stick, or other sporting equipment. The device 2200 may attach to the sporting equipment by being clamped, tightened, and/or wrapped around the shaft of the sports equipment (e.g., a golf club) just beyond the grip in one embodiment. The various elements described herein with regard to a golf club head may also apply to device 2200.

In one embodiment, the device 2200 may have one or more piezoelectric sensor elements 2210 and 2220 oriented to detect vibrations on the shaft caused by striking the ball. In one embodiment, a first piezoelectric sensor 2210 may detect vibrations at substantially a 90 degree angle from a second piezoelectric sensor 2220, thereby allowing for vibration detection along multiple axes.

Like with the piezoelectric sensors integrated into a club head, sensors 2210 and 2220 may provide first and second power signals, respectively, which each may be split according to a predetermined ratio such that a first portion of each power signal is used to charge a battery in device 2200, whereas a second portion of each power signal is processed to analyze characteristics specific to the sporting equipment.

For example, the vibrations may indicate an impact with a ball, and may further form patterns that provide information about the impact, similar to those described with respect to the integrated club head. For example, when attached to a baseball bat a vibration profile may indicate whether the ball was hit on the sweet spot of the bat, or whether the ball was hit too close to the end of the bat or too close to the batter's hands. Similarly, the vibration profile may indicate whether a tennis ball is hit in the middle of the racquet strings, close to a beam or grommet, or on the beam or grommet. The vibration differences along the different axes may also yield information regarding the angle of impact, which, in a sport such as tennis, may also inform regarding spin placed on the ball on a particular shot.

In one embodiment, the processor may determine the ball was hit at the sweet spot based on the vibrations falling into a known frequency band for the expected resonance of the sports instrument. In response, the processor may change the ratio to output a third portion of the power signal to a green LED, the LED giving a visual indicator that the ball was struck well. Alternatively or in addition, the processor may increase the portion of the power signal that is sent to energy storage, since analysis of the sweet spot vibrations may not be necessary. If the processor determines the ball was not hit at the sweet spot, it may change the ratio to send some of the power signal to a red LED, the red LED indicating that the ball was not hit optimally.

In another embodiment, a third piezoelectric sensor 2230 may be placed substantially in-line with the first piezoelectric sensor 2230. These sensors 2210 and 2230 may be part of a single monolith in one embodiment. The processor may compare power signals output by in-line sensors 2210 and 2230 to better calculate an impact location along a particular axis, based on amplitude differences and time offset for similar waveforms between the two sensors 2210 and 2230.

Optimization

The process of optimizing the overall assembly of the integrated electronics golf club head is focused on defining a system golf club head that has all measurements and electronic processing and communication capabilities desired and that functions substantially similar to regulation golf club head of similar type based on physical properties. Further, the specific physical properties being substantially similar include: coefficient of restitution of club face, overall weight of club head and center of gravity of club head. The system club head variables that are defined in this final optimization process include: placement of all assemblies, components and elements in relation to club head shell outer surface and in conjunction defining the club head shell wall thickness profile. The optimization process for the aggregation of all assemblies and structures for the integrated electronics system golf club head include the steps of:

1. Define what functions are to be included in system club head that defines what assemblies will be utilized in or on club head.
2. Define the shape, weight and mass distribution of utilized assemblies from previous optimization processes results for each individual assembly except antenna system.
3. In a CAD (Computer Aided Design) mechanical design tool such as Solidworks™, model each assembly as representative shape, volume and mass density for each assembly from step 2 except antenna system.
4. In CAD tool, model antenna system with club head shell structure with zero mass (zero wall thickness) and without club face assembly and having an outer surface shape or contour and all other elements and objects with mass defined in antenna optimization process.
5. In CAD tool attach club face assembly with antenna system assembly where club face assembly is attached to club head shell outer surface to form entire outer surface of club head system.
6. In CAD tool define an estimated spatial relation all assemblies from step 2 with in assembly antenna system shell shape and club face assembly forming cavity in step 5 that further results in a center of gravity of aggregate of all assemblies near intended center of gravity for overall club head system
7. Add wall thickness in a uniform manner consistent with earlier define material that has a defined mass density to define a club head system with desire overall weight consistent with a regulation golf club head of similar type.
8. Adjust in combination:
    a. wall thickness profile maintaining mass volume of material and outer surface structure of club head shell and
    b. spatial relationships of assemblies to club head shell outer surface to define the desired center of gravity of the overall club head system.
9. Defines an addition weight and mass distribution entity for mounting method and materials used for supporting internal assemblies in defined spatial relationship from step 8 that defines an addition weight and mass distribution entity.
10. Reduce or increase mass of material used for club head shell wall thickness and iterate through steps 8 and 9 until overall club head system desire weight and desired center of gravity are achieved.
11. Validate through CAD structural analysis that club head shell physical structure wall thickness and mounting methods support the physical stresses required for swinging and impact consistent with a golf club head in use as a golfing instrument.
12. If validation is successful optimization is complete. If validation fails alter both club head shell wall thickness profile structure to provide more structural support where needed using define mass allocation and iterate through steps 8-11.

As seen in the overall optimization process of the integrated electronics system golf club head design, the process requires providing structural integrity of club head shell structure with a predetermine weight that is less than a typical club head shell of similar type without additional assemblies. The club head wall thickness profile variable and the materials profile selected are the central control factors defining structural integrity within the confines of a predetermined weight limit and predetermined center of gravity.

Figure 10A:
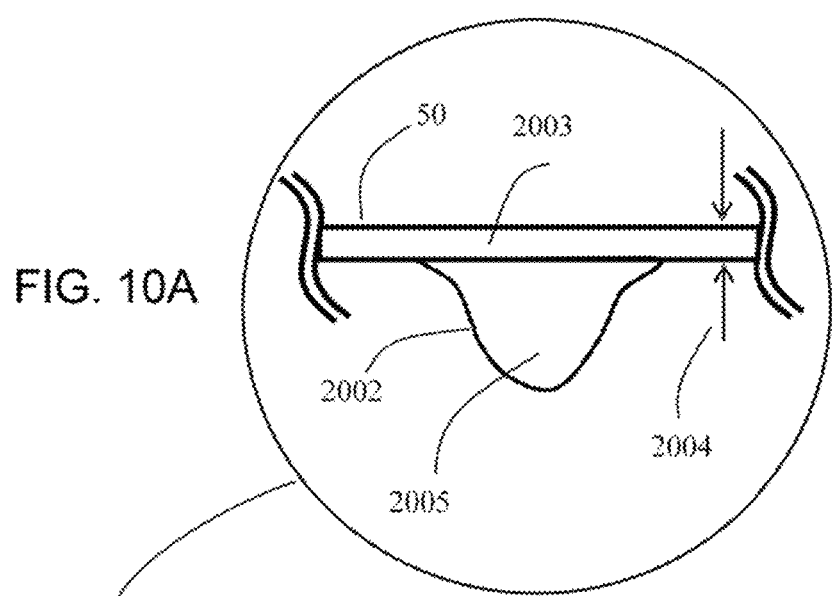
FIG. 10A is a cross-sectional view of club head shell wall of FIG. 10 showing a wall thickness profile structure embodiment comprising two separate materials.
Figure 10:
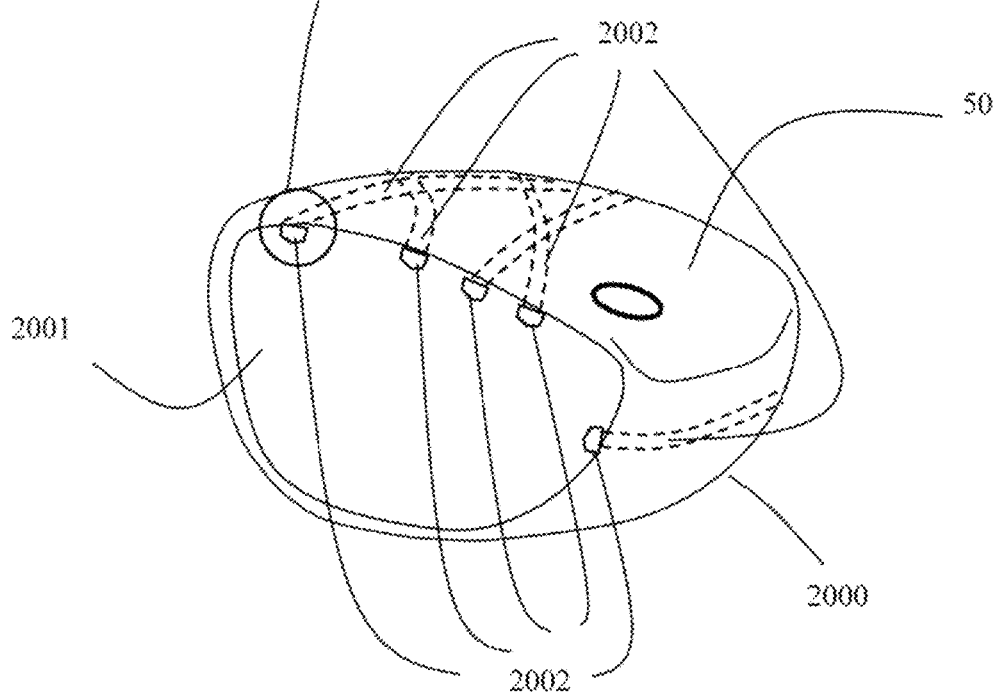
FIG. 10 is the club head shell showing club head wall with a varying wall thickness structure embodiment for optimizing weight, balance and structural integrity of overall club head shell.

FIG. 10 shows a club head shell 2000 with exemplary varying wall thickness profile type for the benefit of minimal weight and robust structural integrity. The club head shell 2000 (without the club face) has an outer surface 50 and an inner cavity 2001 and inner cavity 2001 has an inner surface (not labeled). This first embodiment of the club head shell structure defines a wall thickness profile that comprises areas of increased thickness 2002 and allows the predetermined and predefined outer surface 50 shape or contour to remain constant and unchanged. Exemplary areas of increased thickness 2002 are shown protruding into the inner cavity 2001 as interconnected ribs and are only shown for a small portion of the total shell for clarity of illustrative drawing purposes, however, would be implemented throughout the club head shell structure in predetermined area locations of the shell 2000 based on known applied stress and acceptable strain requirements. The areas of increased thickness 2002 in this example can be described as rib like structures that are similar to truss systems that provide large structure force support with a conservative use of materials. The areas of increased thickness 2002 or interconnected ribs adapted to be a truss like system provides structural resilience to stresses experienced by the club head shell, especially a ball impact on the club face and stress areas around the hosel connection. The areas of increased thickness 2002 or ribbed structural system allows forces acting on the club head shell to be distributed along interconnected ribs allowing the shell wall thickness between the ribs to be very thin for the benefit of weight and mass distribution control. The areas of increased thickness 2002 and the protrusion thickness differences as compared to areas of minimal wall thickness define a volume of material that may be made of any predetermined material that is the same as, or similar to, or non-similar to, the material of the outer surface 50 with electrically conductive properties. In this embodiment the material properties of the said volume of material for areas of increased wall thickness are the same as the material properties of the outer surface 50. Further the minimal wall thickness of the club head shell with regards to antenna function purposes requires only a few microns to a few mils of thickness as defined by skin effects related to the material property of electrical conductivity of metal(s) or alloy(s) used for the outer surface. Therefore, the minimum thickness of the club head shell wall thickness covering and between the areas of increased thickness 2002 or ribs is dominated only by the requirement of structural enhancement through support of the ribs. The areas of increased thickness 2002 or ribbed structures and minimal thickness areas are described entirely with the wall thickness profile of the club head shell 2000. Further the areas of increased thickness 2002 or ribs system on inner portion of club head shell may be any predetermined three dimensional pattern(s) or non-symmetric design that meets the desired structural physical properties and weight and mass distribution goals of club head shell system.

As shown in FIG. 10A another embodiment of the club head shell structure utilizes multiple materials. FIG. 10 A shows a close up of a cross section view showing a multi material wall thickness profile structure. The first material 2003 is used for the club shell outer surface area 50 and the portion of the wall thickness profile from the surface area 50 to a depth into the wall defined by minimum wall thickness 2004. The first material 2003 is a material such as a metal or alloy that has electrically conductive properties required by the antenna system. The second material 2005 is used for areas of increased wall thickness 2002 and may be a light weight composite or other type material with high structural strength and low mass density for light weight structural support. Example of such materials may be but not limited to a resin based carbon fiber composite. The first material and second material may be attached with a high strength adhesive or other attachment bonding process.

The club head shell structure with predetermined varying wall thickness profile is modeled and designed as a single entity, however for manufacturing purposes the design is segmented into two or more pieces that are attached through welding or other affixing process. An example of the segmented two pieces may be a crown and a base that allow attachment of other electronics based assemblies before attachment of crown and based and club face.

The preferred embodiment of the measurements and analysis system functions in the following manner. As the golfer swings the club, the club head is in bidirectional wireless communication with a second module and in this embodiment a wireless USB module that is placed at a predetermined location near the swing path of the integrated electronics golf club head. The wireless USB Module is also in wired communication with a user interface device that in this embodiment is a laptop computer. As the golf swing is in progress weather it is a free swing or a swing with impact the club head is capturing sensor data and receiver signal strength data from the wireless USB. The integrated electronics club head is also transmitting the all sensor measurements synchronized with the receiver signal strength measurements to the wireless USB module that then further transmits the data through a wired connection to the user interface device that in the case is a laptop. Residing on the laptop is application software that runs algorithms to interpret all data that has been measured at the club head. The following sections describe how these algorithms to interpret and calculate the swing metrics from the measurement made at the club head.

The following section of this patent application describe the algorithms used in the processing software to interpret all sensors and receiver signal strength measurements made at the club head during free swing and during impact to provide a rich set golf metrics describing the quality of a golf free swing or a golf swing with impact.

Figure 11:
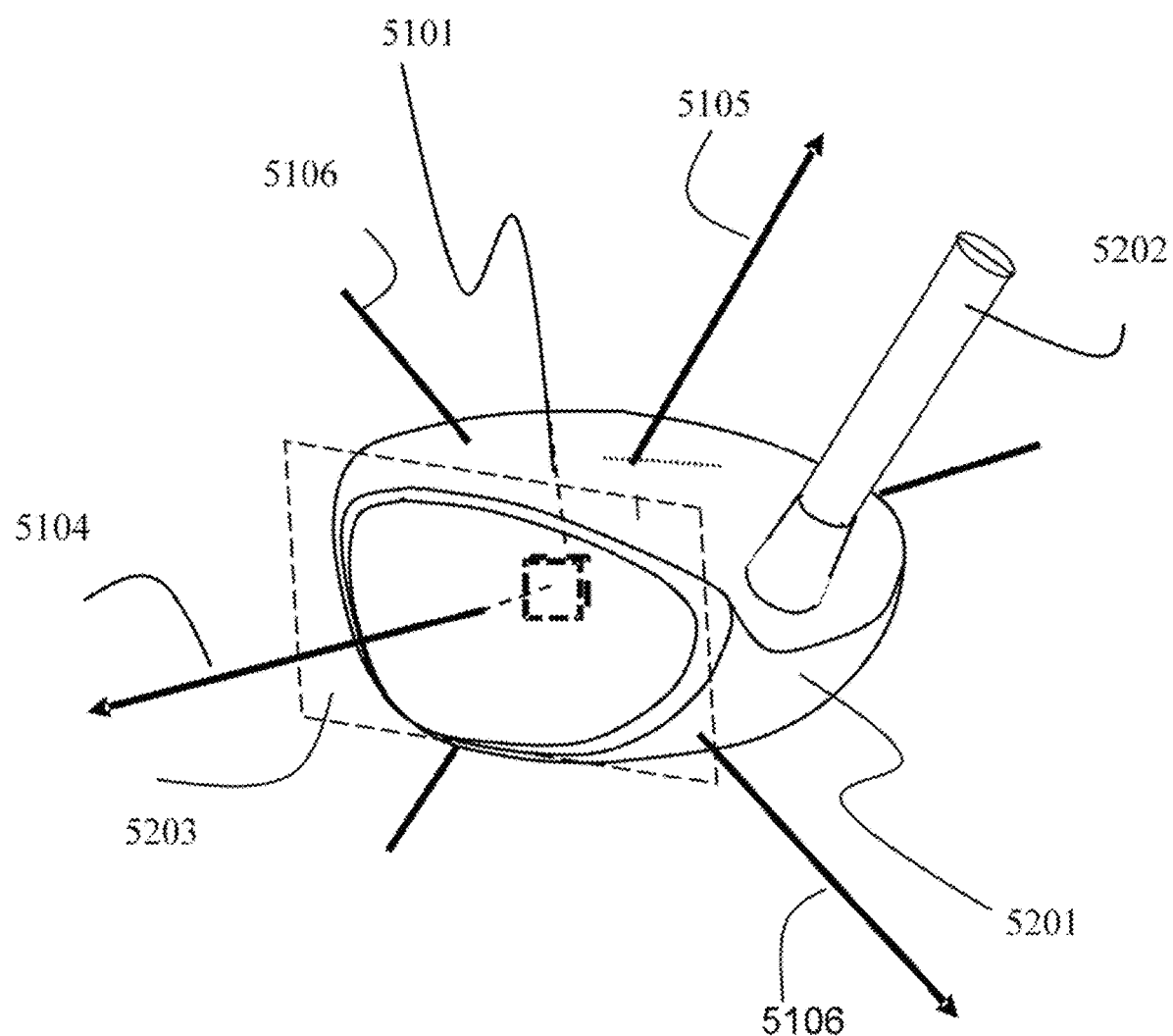
FIG. 11 is a perspective view of the club head acceleration measurement assembly in the club head and the alignment of the three orthogonal measurement axes $x_f$, $y_f$ and $z_f$ to the golf club structure.

FIG. 11 shows the preferred embodiment of the invention, which is the acceleration measurement assembly 5101 with three orthogonal measurement axes $x_f$-axis 5104, $z_f$-axis 5105 and $y_f$-axis 5106 that is attached inside the club head 5201 as earlier described in the system optimization process.

For the club head acceleration measurement assembly 5101 mounted perfectly in the club head 5201 the following relations are achieved: The $z_f$-axis 5105 is aligned so that it is parallel to the club shaft 5202. The $x_f$-axis 5104 is aligned so that is orthogonal to the $z_f$-axis 5105 and perpendicular to the plane 5203 that would exist if the club face has a zero loft angle. The $y_f$-axis 5106 is aligned orthogonally to both the $x_f$-axis 5104 and $z_f$-axis 5105.

With these criteria met, the plane created by the $x_f$-axis 5104 and the $y_f$-axis 5106 is perpendicular to the non-flexed shaft 5202. In addition the plane created by the $y_f$-axis 5106 and the $z_f$-axis 5105 is parallel to the plane 5203 that would exist if the club face has a zero loft angle. However, in the manufacturing process of the integrated electronics club head there may be variations in alignment of the orientation of the acceleration measurement assembly 5101 that are detected and corrected with a correction algorithm that is covered later.

The mathematical label $a_{sx}$ represents the acceleration force measured by a sensor along the club head acceleration measurement assembly 5101 $x_f$-axis 5104. The mathematical label $a_{sy}$ represents the acceleration force measured by a sensor along the club head acceleration measurement assembly 5101 $y_f$-axis 5106. The mathematical label $a_{sz}$ represents the acceleration force measured by a sensor along the club head acceleration measurement assembly 5101 $z_f$-axis 5105.

If the club head acceleration measurement assembly of the preferred embodiment is not aligned exactly with the references of the golf club there is an algorithm that is used to detect and calculated the angle offset from the intended references of the club system and a method to calibrate and correct the measured data. This algorithm is covered in detail after the analysis is shown for proper club head acceleration measurement assembly attachment with no mounting angle variations.

Figure 12:
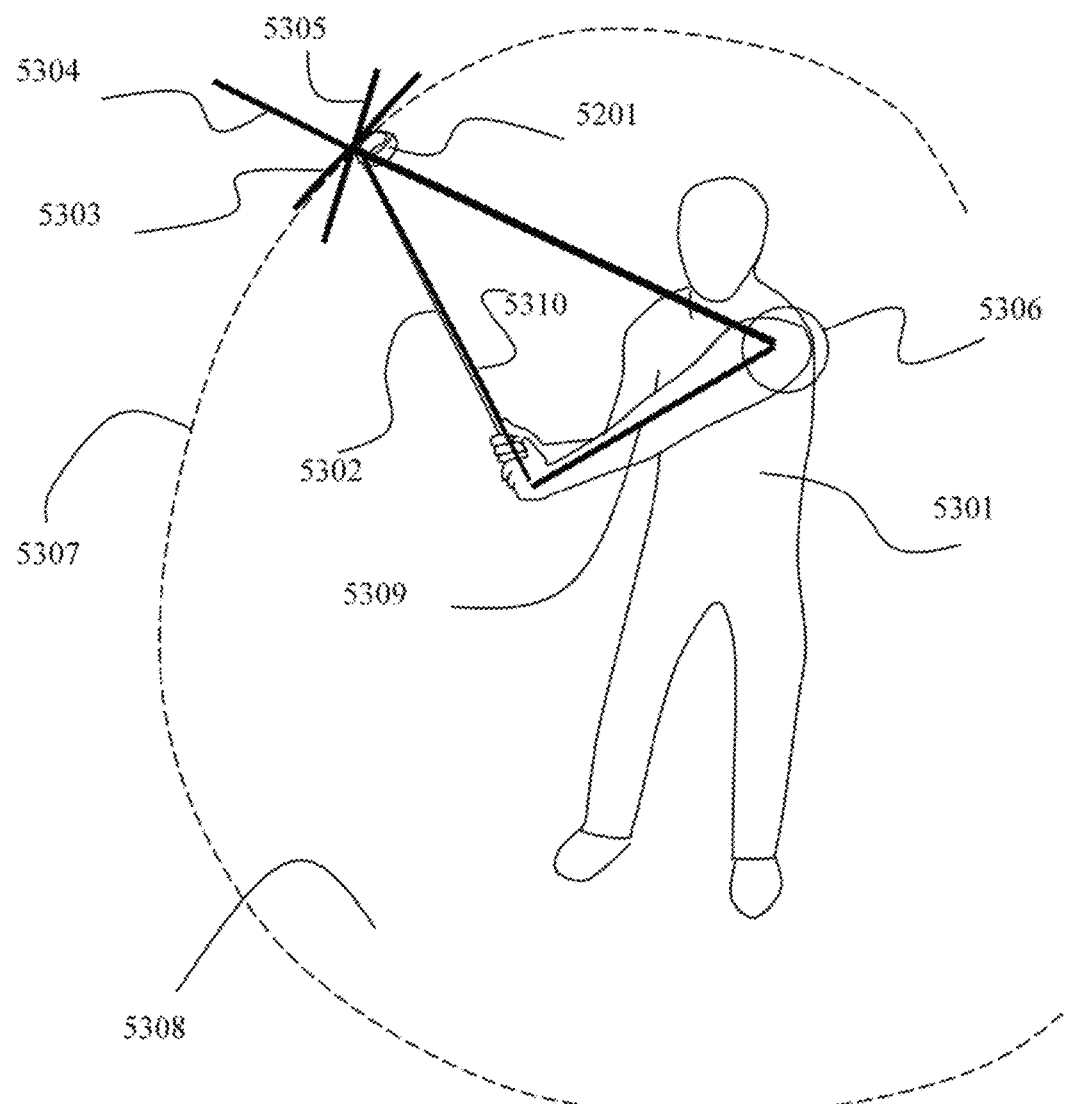
FIG. 12 is a perspective view of the "inertial" motion axes of the club head motion $x_{cm}$, $y_{cm}$ and $z_{cm}$ as the golfer swings the club and how these axes relate to the multi-lever model components of the golfer's swing.

Club head motion is much more complicated than just pure linear accelerations during the swing. It experiences angular rotations of the fixed sensor orthogonal measurement axes, $x_f$-axis 5104, $y_f$-axis 5106 and $z_f$-axis 5105 of acceleration measurement assembly 5101 around all the center of mass inertial acceleration force axes during the swing, as shown in FIG. 12. As the golfer 5301 swings the golf club 5302 and the club head 5201 travels on an arc there are inertial center of mass axes along which inertia forces act on the center of mass of the club head 5201. These are the $x_{cm}$-axis 5303, $y_{cm}$-axis 5305 and $z_{cm}$-axis 5304.

The three orthogonal measurement axes $x_f$-axis 5104, $y_f$-axis 5106 and $z_f$-axis 5105 of acceleration measurement assembly 5101, along with a physics-based model of the multi-lever action of the swing of the golfer 5301, are sufficient to determine the motion relative to the club head three-dimensional center of mass axes with the $x_{cm}$-axis 5303, $y_{cm}$-axis 5305 and $z_{cm}$-axis 5304.

The mathematical label $a_z$ is defined as the acceleration along the $z_{cm}$-axis 5304, the radial direction of the swing, and is the axis of the centrifugal force acting on the club head 5201 during the swing from the shoulder 5306 of the golfer 5301. It is defined as positive in the direction away from the golfer 5301. The mathematical label $a_x$ is the defined club head acceleration along the $x_{cm}$-axis 5303 that is perpendicular to the $a_z$-axis and points in the direction of instantaneous club head inertia on the swing arc travel path 5307. The club head acceleration is defined as positive when the club head is accelerating in the direction of club head motion and negative when the club head is decelerating in the direction of club head motion. The mathematical label $a_y$ is defined as the club head acceleration along the $y_{cm}$-axis 5305 and is perpendicular to the swing plane 5308.

During the golfer's 5301 entire swing path 5308, the dynamically changing relationship between the two coordinate systems, defined by the acceleration measurement assembly 5101 measurements coordinate system axes $x_f$-axis 5104, $y_f$-axis 5106 and $z_f$-axis 5105 and the inertial motion acceleration force coordinate system axes $x_{cm}$-axis 5303, $y_{cm}$-axis 5305 and $z_{cm}$-axis 5304, must be defined. This is done through the constraints of the multi-lever model partially consisting of the arm lever 5309 and the club shaft lever 5310.

Figure 13:
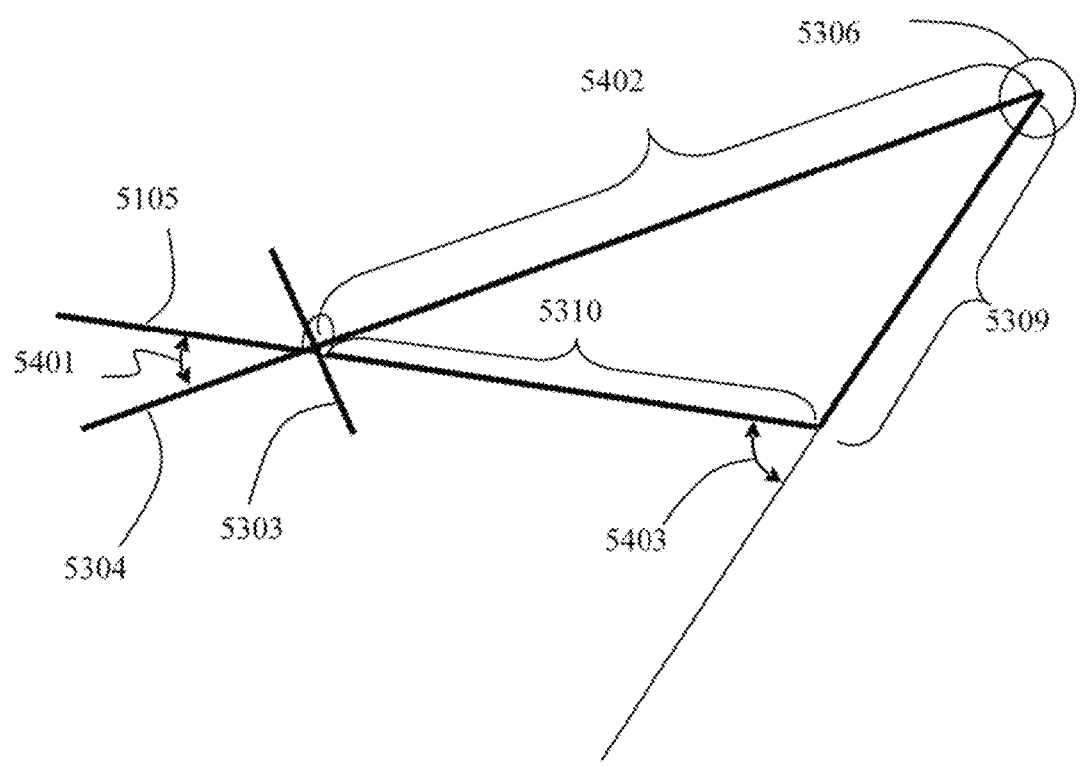
FIG. 13 shows the multi-lever variable radius model system and two key interdependent angles and a and their relationship between the two coordinate systems; the measured axes of club head acceleration measurement assembly $x_f$, $y_f$ and $z_f$, and a second coordinate system comprising the inertial motion axes of club head travel $x_{cm}$, $y_{cm}$ and $z_{cm}$.

The multi lever system as shown in FIG. 13 shows two interdependent angles defined as angle 5401 which is the angle between the club head acceleration measurement assembly 5101 $z_f$-axis 5105 and the inertial $z_{cm}$-axis 5304 and the angle α 5403 which is the sum of wrist cock angle and shaft flex lag/lead angle (shown later in FIGS. 16 and 16A). The angle 5401 is also the club head rotation around the $y_{cm}$-axis 5106 (not shown in FIG. 13 but is perpendicular to the page at the club head center of mass) and is caused largely by the angle of wrist cock, and to a lesser extent club shaft flexing during the swing. The length of the variable swing radius R 5402 is a function of the fixed length arm lever 5309, the fixed length club shaft lever 5310 and the angle η 5401. The angle η 5401 can vary greatly, starting at about 40 degrees or larger at the start of the downswing and approaches zero at club head maximum velocity. The inertial $x_{cm}$-axis 5303 is as previously stated perpendicular to the inertial $z_{cm}$-axis 5304 and variable radius R 5402.

Figure 14:
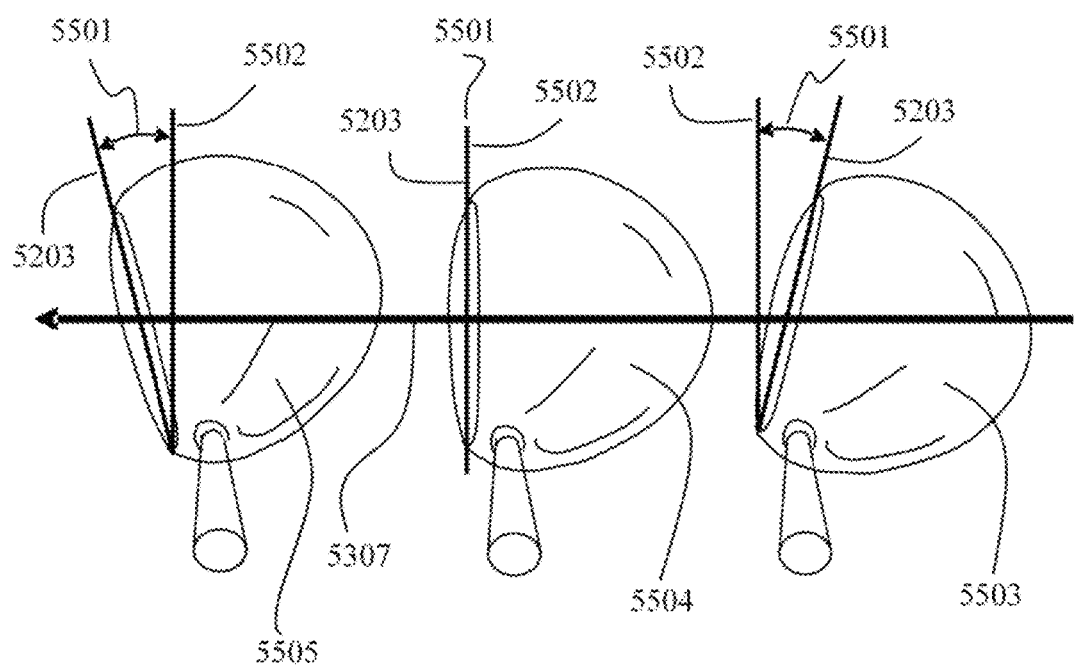
FIG. 14 shows the club face angle $\Phi$ for different club orientations referenced to the club head travel path.

FIG. 14 shows the angle Φ 5501 which is the club face angle and is defined as the angle between the plane 5502 that is perpendicular to the club head travel path 5307 and the plane that is defined for zero club face loft 5203. The angle Φ 5501 also represents the club head rotation around the $z_f$-axis 5105. The angle Φ 5501 varies greatly throughout the swing starting at about 90 degrees or larger at the beginning of the downswing and becomes less positive and perhaps even negative by the end of the down stroke. When the angle Φ 5501 is positive the club face angle is said to be "OPEN" as shown in club head orientation 5503. During an ideal swing the angle Φ 5501 will be zero or said to be "SQUARE" at the point of maximum club head velocity as shown in club head orientation 5504. If the angle Φ 5501 is negative the club face angle is said to be "CLOSED" as shown in club head orientation 5505.

Figure 15:
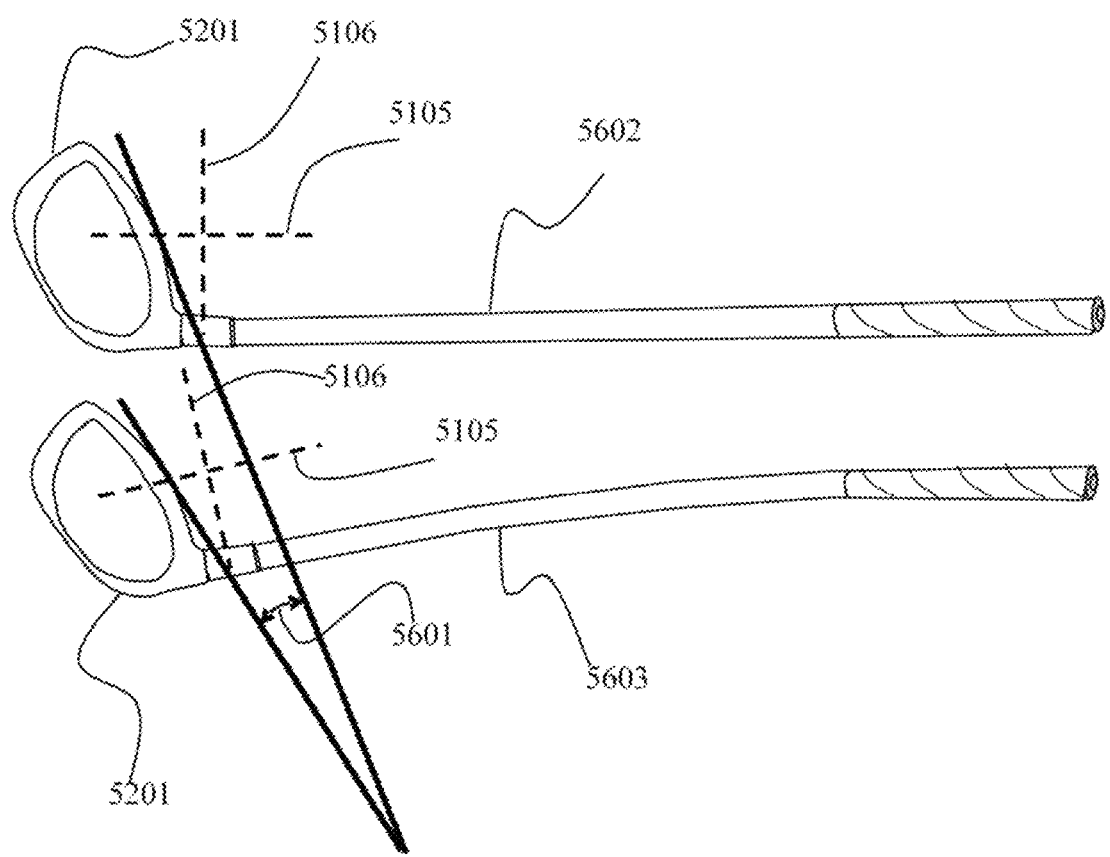
FIG. 15 shows the toe down angle, $\Omega$, and it's reference to the shaft bow state and measurement axis dynamics.

FIG. 15 shows angle Ω 5601 which is referred to as the toe down angle and is defined as the angle between the top of a club head 5201 of a golf club with a non-bowed shaft state 5602 and a golf club head 5201 of a golf club with bowed shaft state 5603 due to the centrifugal force pulling the club head toe downward during the swing. The angle Ω is a characteristic of the multi-lever model representing the non-rigid club lever. The angle Ω 5601 also represents the club head 5201 rotation around the $x_f$-axis 5104 (not shown in FIG. 15, but which is perpendicular to the $y_f$-axis 5106 and $z_f$-axis 5105 intersection). The angle Ω 5601 starts off at zero at the beginning of the swing, and approaches a maximum value of a few degrees at the maximum club head velocity.

Figures 16, 16A:
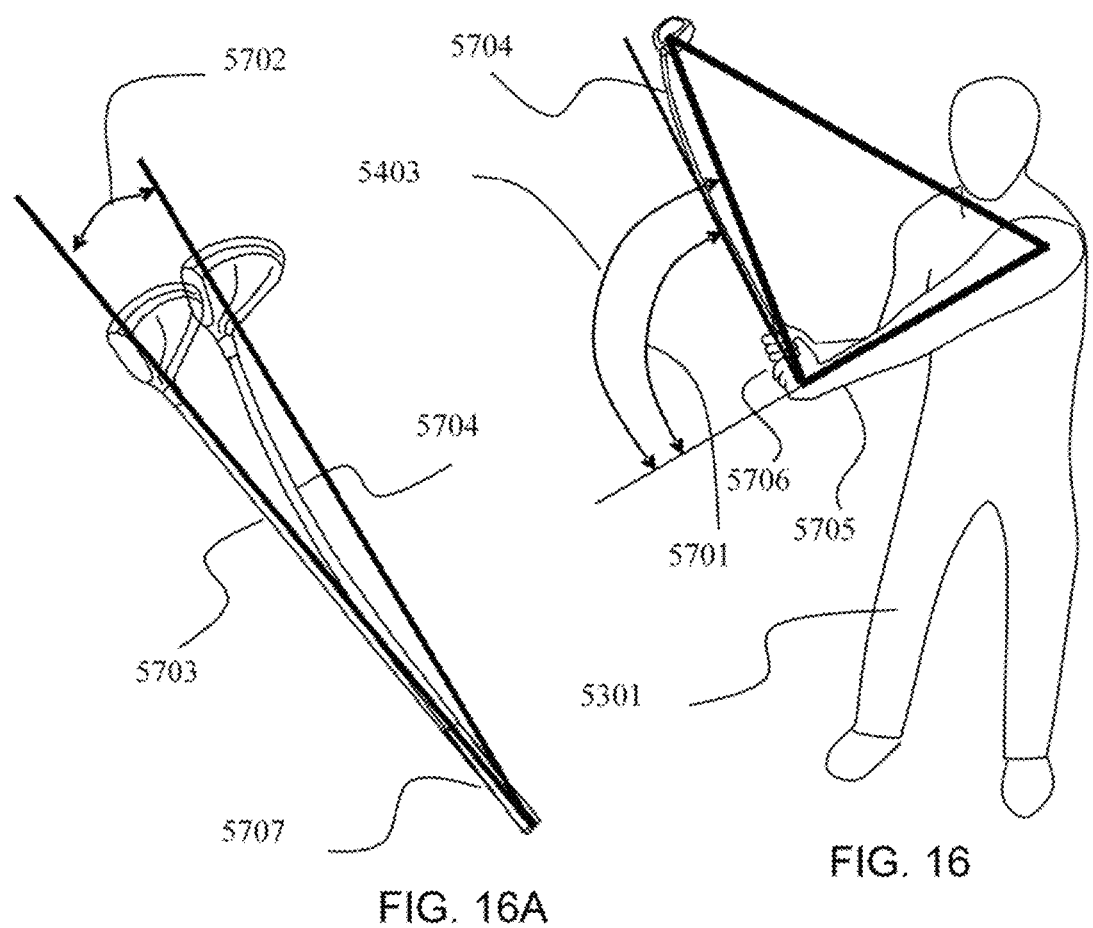
FIGS. 16 and 16A shows wrist cock angle $\alpha_{wc}$, and the shaft flex lag/lead angle $\alpha_{sf}$ which together sum to the angle $\alpha$.

FIGS. 16 and 16A show the angle α 5403 which is the sum of angles $α_{wc}$ 5701, defined as the wrist cock angle, and $α_{sf}$ 5702, defined as the shaft flex lag/lead angle. The angle $α_{sf}$ 5702 is the angle between a non-flexed shaft 5703 and the flexed shaft state 5704, both in the swing plane 5308 defined in FIG. 12, and is one characteristic of the non-rigid lever in the multi-lever model. The shaft leg/lead flex angle $α_{sf}$ 5702 is caused by a combination of the inertial forces acting on the club and the wrist torque provided by the golfer's 5301 wrists 5705 and hands 5706 on the shaft grip 5707.

Figure 17:
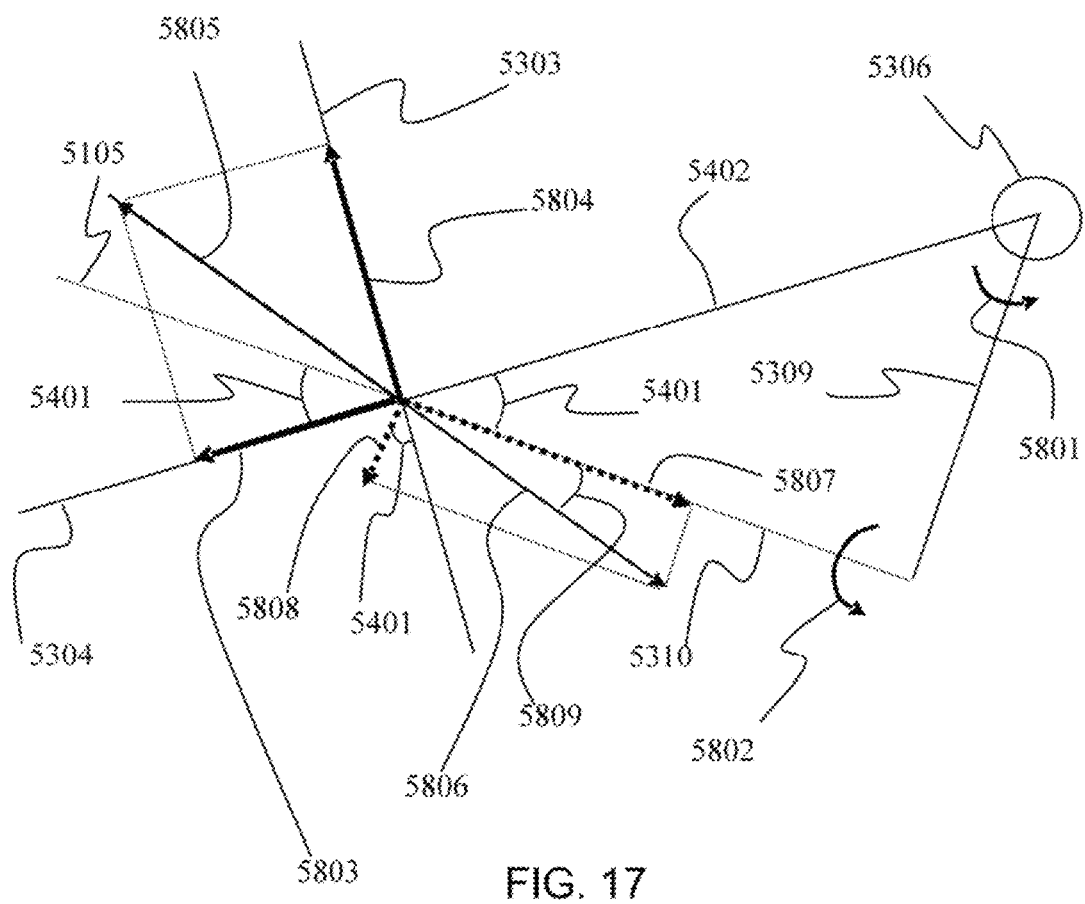
FIG. 17 shows the force balance for the multi-lever variable radius swing model system and the inter-relationship to both axes systems.

FIG. 17 shows the force balance for the multi-lever swing system. The term $a_v$ 5805 is the vector sum of $a_x$ 5804 and $a_z$ 5803. The resulting force is given by $F_v=m_s a_v$ where $m_s$ is the mass of the club head system. The term $F_v$ 5806 is also, from the force balance, the vector sum of the tensile force, $F_t$ 5807, in the shaft due to the shoulder torque 5801, and $F_{wt}$ 5808, due to wrist torque 5802. The angle between force vector $F_v$ 5806 and the swing radius, R 5402, is the sum of the angles η 5401 and $η_{wt}$ 5809.

There are several ways to treat the rotation of one axes frame relative to another, such as the use of rotation matrices. The approach described below is chosen because it is intuitive and easily understandable, but other approaches with those familiar with the art would fall under the scope of this invention.

Using the multi-lever model using levers, rigid and non-rigid, the rotation angles describing the orientation relationship between the acceleration measurement assembly measured axis coordinate system and the inertial acceleration force axes coordinate system can be determined from the sensors in the club head acceleration measurement assembly 5101 through the following relationships:

$$a_{sx}=a_x \cos(\Phi)\cos(\eta)-a_y \sin(\Phi)-a_z \cos(\Phi)\sin(\eta) \quad 1.$$

$$a_{sy}=a_x \sin(\Phi)\cos(\eta)+a_y \cos(\Phi)+a_z(\sin(\Omega)-\sin(\Phi)\sin(\eta)), \quad 2.$$

$$a_{sz}=a_x \sin(\eta)-a_y \sin(\Omega)\cos(\Phi)+a_z \cos(\eta) \quad 3.$$

The following is a reiteration of the mathematical labels for the above equations.

$a_x$ is the club head acceleration in the $x_{cm}$-axis 303 direction.

$a_y$ is the club head acceleration in the $y_{cm}$-axis 305 direction.

$a_z$ is the club head acceleration in the $z_{cm}$-axis 304 direction.

$a_{sx}$ is the acceleration value returned by the club head acceleration measurement assembly 5101 sensor along the $x_f$-axis 5104.

$a_{sy}$ is the acceleration value returned by the club head acceleration measurement assembly 5101 sensor along the $y_f$-axis 5106.

$a_{sz}$ is the acceleration value returned by the club head acceleration measurement assembly 5101 sensor along the $z_f$-axis 5105.

During a normal golf swing with a flat swing plane 5308, $a_y$ will be zero, allowing the equations to be simplified:

$$a_{sx}=a_x \cos(\Phi)\cos(\eta)-a_z \cos(\Phi)\sin(\eta) \quad 4.$$

$$a_{sy}=a_x \sin(\Phi)\cos(\eta)+a_z(\sin(\Omega)-\sin(\Phi)\sin(\eta)) \quad 5.$$

$$a_{sz}=a_x \sin(\eta)+a_z \cos(\eta) \quad 6.$$

These equations are valid for a "free swing" where there is no contact with the golf ball.

The only known values in the above are $a_{sx}$, $a_{sy}$, and $a_{sz}$ from the three sensors. The three angles are all unknown. It will be shown below that $a_x$ and $a_z$ are related, leaving only one unknown acceleration. However, that still leaves four unknowns to solve for with only three equations. The only way to achieve a solution is through an understanding the physics of the multi-lever variable radius swing system dynamics and choosing precise points in the swing where physics governed relationships between specific variables can be used.

The angle Φ 5501, also known as the club face approach angle, varies at least by 180 degrees throughout the backswing, downswing, and follow through. Ideally it is zero at maximum velocity, but a positive value will result in an "open" clubface and negative values will result in a "closed" face. The angle Φ 5501 is at the control of the golfer and the resulting swing mechanics, and is not dependent on either $a_x$ or $a_z$. However, it can not be known a-priori, as it depends entirely on the initial angle of rotation around the shaft when the golfer grips the shaft handle and the angular rotational velocity of angle Φ 5501 during the golfer's swing.

The angle Ω 5601, on the other hand, is dependent on $a_z$, where the radial acceleration causes a centrifugal force acting on the center of mass of the club head, rotating the club head down around the $x_f$-axis into a "toe" down position of several degrees. Therefore, angle Ω 5601 is a function of $a_z$. This function can be derived from a physics analysis to eliminate another unknown from the equations.

The angle 5401 results from both club shaft angle 5702 lag/lead during the downswing and wrist cock angle 5701. Wrist cock angle is due both to the mechanics and geometry relationships of the multi lever swing model as shown in FIG. 12 and the amount of torque exerted by the wrists and hands on the shaft.

Before examining the specifics of these angles, it is worth looking at the general behavior of equations (4) through (6). If both angle Ω 5601 and angle 5401 were always zero, which is equivalent to the model used by Hammond in U.S. Pat. No. 3,945,646, the swing mechanics reduces to a single lever constant radius model. For this case:

$$a_{sx}=a_x \cos(\Phi) \quad 7.$$

$$a_{sy}=a_x \sin(\Phi) \quad 8.$$

$$a_{sz}=a_z \quad 9.$$

This has the simple solution for club face angle Φ of:

$$\tan(\Phi) = \frac{a_{sy}}{a_{sx}} \quad 10.$$

In Hammond's patent U.S. Pat. No. 3,945,646 he states in column 4 starting in line 10 "By computing the vector angle from the acceleration measured by accelerometers 12 and 13, the position of the club face 11 at any instant in time during the swing can be determined." As a result of Hammond using a single lever constant radius model which results in equation 10 above, it is obvious he failed to contemplate effects of the centrifugal force components on sensor 12 and sensor 13 of his patent. The large error effects of this can be understood by the fact that the $a_z$ centrifugal acceleration force is typically 50 times or more greater than the measured acceleration forces of $a_{sx}$ and $a_{sy}$ for the last third of the down swing and first third of the follow through. Therefore, even a small angle Ω 5601 causing an $a_z$ component to be rotated onto the measured $a_{sy}$ creates enormous errors in the single lever golf swing model.

In addition, the effect of the angle η 5401 in the multi lever variable radius swing model is to introduce $a_z$ components into $a_{sx}$ and $a_{sy}$, and an $a_x$ component into $a_{sz}$. The angle η 5401 can vary from a large value at the start and midpoint of the down stroke when $a_z$ is growing from zero. In later portion of the down stroke $a_z$ becomes very large as angle η 5401 tends towards zero at maximum velocity. Also, as mentioned above, the angle η 5401 introduces an $a_x$ component into $a_{sz}$. This component will be negligible at the point of maximum club head velocity where angle η 5401 approaches zero, but will be significant in the earlier part of the swing where angle η 5401 is large and the value of $a_x$ is larger than that for $a_z$.

The cos(η) term in equations (4) and (5) is the projection of $a_x$ onto the $x_f$-$y_f$ plane, which is then projected onto the $x_f$-axis 5104 and the $y_f$-axis 5106. These projections result in the $a_x \cos(\Phi)\cos(\eta)$ and $a_x \sin(\Phi)\cos(\eta)$ terms respectively in equations (4) and (5). The projection of $a_x$ onto the $z_f$-axis 5105 is given by the $a_x \sin(\eta)$ term in equation (6).

The sin(η) terms in equations (4) and (5) are the projection of $a_z$ onto the plane defined by $x_f$ axis 5104 and the $y_f$ axis 5106, which is then projected onto the $x_f$-axis 5104 and $y_f$-axis 5106 through the $a_z \cos(\Phi)\sin(\eta)$ and $a_z \sin(\Phi)\sin(\eta)$ terms respectively in equations (4) and (5). The projection of $a_z$ onto the $z_f$-axis 5105 is given by the $a_z \cos(\eta)$ term in equation (6).

The angle Ω 5601 introduces yet another component of $a_z$ into $a_{sy}$. The angle Ω 5601 reaches a maximum value of only a few degrees at the point of maximum club head velocity, so its main contribution will be at this point in the swing. Since angle Ω 5601 is around the $x_f$-axis 5104, it makes no contribution to $a_{sx}$, so its main effect is the $a_z \sin(\Omega)$ projection onto the $y_f$-axis 5106 of equation (5). Equations (4) and (5) can be simplified by re-writing as:

$$a_{sx} = (a_x\cos(\eta) - a_z\sin(\eta))\cos(\Phi) = f(\eta)\cos(\Phi) \text{ and} \quad 11.$$

$$a_{sy} = \qquad\qquad\qquad\qquad\qquad\qquad\qquad\qquad\qquad 12.$$
$$(a_x\cos(\eta) - a_z\sin(\eta))\sin(\Phi) + a_z\sin(\Omega) = f(\eta)\sin(\Phi) + a_z\sin(\Omega) \text{ where}$$

$$f(\eta) = a_x\cos(\eta) - a_z\sin(\eta). \text{ From (11):} \quad 13.$$

$$f(\eta) = \frac{a_{sx}}{\cos(\Phi)} \text{ which when inserted into (12) obtains:} \quad 14.$$

$$a_{sy} = a_{sx}\tan(\Phi) + a_z\sin(\Omega) \quad 15.$$

From equation (15) it is seen that the simple relationship between $a_{sx}$ and $a_{sy}$ of equation (10) is modified by the addition of the $a_z$ term above. Equations (4) and (6) are re-written as:

$$a_x = \frac{a_{sx}}{\cos(\eta)\cos(\Phi)} + \frac{a_z\sin(\eta)}{\cos(\eta)} \quad 16.$$

$$a_z = \frac{a_{sz}}{\cos(\eta)} - \frac{a_x\sin(\eta)}{\cos(\eta)}. \quad 17.$$

These equations are simply solved by substitution to yield:

$$a_z = a_{sz}\cos(\eta) - a_{sx}\frac{\sin(\eta)}{\cos(\Phi)}. \quad 18.$$

$$a_x = a_{sz}\sin(\eta) + a_{sx}\frac{\cos(\eta)}{\cos(\Phi)}. \quad 19.$$

Equation (19) can be used to find an equation for sin(η) by re-arranging, squaring both sides, and using the identity, $\cos^2(\eta)=1-\sin^2(\eta)$, to yield a quadratic equation for sin(η), with the solution:

$$\sin(\eta) = \frac{a_x a_{sz} + \frac{a_{sx}^2}{\cos^2(\Phi)}\sqrt{1-\cos^2(\Phi)\left(\frac{a_{sz}^2 - a_x^2}{a_{sx}^2}\right)}}{a_{sz}^2 + \frac{a_{sx}^2}{\cos^2(\Phi)}}. \quad 20.$$

To get any further for a solution of the three angles, it is necessary to examine the physical cause of each. As discussed above the angle η 5401 can be found from an analysis of the angle α 5403, which is the sum of the angles $\alpha_{wC}$ 5701, due to wrist cock and $\alpha_{sf}$ 5702 due to shaft flex lag or lead.

Angle α 5403, and angle η 5401 are shown in FIG. 4 in relationship to variable swing radius R 5402, fixed length arm lever A 5309, and fixed length club shaft lever C 5310. The mathematical equations relating these geometric components are:

$$R^2 = A^2 + C^2 + 2AC\cos(\alpha) \quad 21.$$

$$A^2 = R^2 + C^2 - 2RC\cos(\eta) \quad 22.$$

Using $R^2$ from equation (21) in (22) yields a simple relationship between α and η:

$$\alpha = \cos^{-1}((R\cos(\eta)-C)/A) \quad 23.$$

The swing radius, R 5402, can be expressed either in terms of cos(α) or cos(η). Equation (21) provides R directly to be:

$$R = \sqrt{C^2 + A^2 + 2AC\cos(\alpha)}. \quad 24.$$

Equation (22) is a quadratic for R which is solved to be:

$$R = C\cos(\eta) + \sqrt{C^2(\cos(\eta)-1) + A^2}. \quad 25.$$

Both α 5403 and η 5401 tend to zero at maximum velocity, for which $R_m = A+C$. The solutions for the accelerations experienced by the club head as it travels with increasing velocity on this swing arc defined by equation (25) are:

$$a_z = \frac{V_\Gamma^2}{R} - \frac{dV_R}{dt} \quad 26.$$

$$a_x = \frac{2}{R}V_R V_\Gamma + R\frac{d}{dt}\left(\frac{V_\Gamma}{R}\right) \quad 27.$$

The acceleration $a_z$ is parallel with the direction of R 5402, and $a_x$ is perpendicular to it in the swing plane 5308. The term $V_\Gamma$ is the velocity perpendicular to R 5402 in the swing plane 5308, where Γ is the swing angle measured with respect to the value zero at maximum velocity. The term $V_R$ is the velocity along the direction of R 5402 and is given by dR/dt. The swing geometry makes it reasonably straightforward to solve for both $V_R$ and its time derivative, and it will be shown that $a_z$ can also be solved for which then allows a solution for $V_\Gamma$:

$$V_\Gamma = \sqrt{Ra_z + R\frac{dV_r}{dt}} \qquad 28.$$

Now define:

$$a_{z-radial} = \frac{V_\Gamma^2}{R} \qquad 29.$$

so that:

$$V_\Gamma = \sqrt{Ra_{z-radial}}, \qquad 30.$$

Next define:

$$a_{ch} = \frac{dV_\Gamma(t)}{dt} = \frac{\Delta V_\Gamma(t)}{\Delta t}, \qquad 31.$$

Because (31) has the variable R 5402 included as part of the time derivative equation (27) can be written:

$$a_x = a_{ch} + \frac{2}{R}V_R V_\Gamma \qquad 32.$$

Also equation (26) can be written:

$$a_z = a_{z-radial} - \frac{dV_R}{dt} \qquad 33.$$

The acceleration a, 805 is the vector sum of $a_x$ 5804 and $a_z$ 5803 with magnitude:

$$a_v = \sqrt{a_x^2 + a_z^2} = \frac{a_x}{\sin(\beta)} = \frac{a_z}{\cos(\beta)} \qquad 34.$$

where $$\beta = \tan^{-1}\left(\frac{a_x}{a_z}\right) \qquad 35.$$

The resulting magnitude of the force acting on the club head is then:

$$F_v = m_s a_v \qquad 36.$$

FIG. 17 shows this force balance for $F_v$ 5806. If there is no force $F_{wt}$ 5808 acting on the golf club head due to torque 5802 provided by the wrists, then $F_v$ 5806 is just $F_t$ 5807 along the direction of the shaft, and is due entirely by the arms pulling on the shaft due to shoulder torque 5801. For this case it is seen that:

$$\beta = \eta \text{ for no wrist torque.} \qquad 37.$$

On the other hand, when force $F_{wt}$ 5808 is applied due to wrist torque 5802:

$$\beta = \eta + \eta_{wt} \text{ where:} \qquad 38.$$

$$F_{wt} = F_v \sin(\eta_{wt}). \qquad 39.$$

The angle $\eta_{wt}$ 5809 is due to wrist torque 5802. From (38):

$$\eta = \left(1 - \frac{\eta_{wt}}{\beta}\right)\beta = C_\eta \beta \qquad 40.$$

where $C_\eta < 1$ is a curve fitting parameter to match the data, and is nominally around the range of 0.75 to 0.85. From the fitted value:

$$\eta_{wt} = (1 - C_\eta)\beta \qquad 41.$$

Using (41) in (39) determines the force $F_{wt}$ 5808 due to wrist torque 5802.

Figure 18:
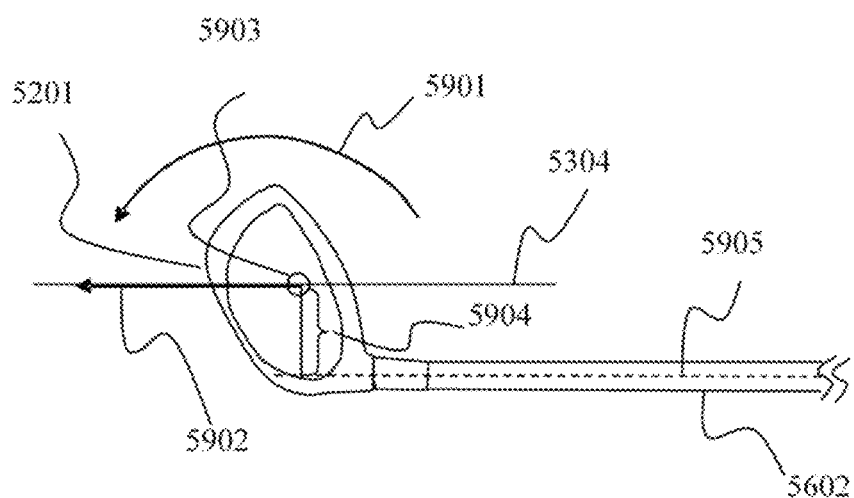
FIG. 18 shows the force balance for the flexible lever portion of the multi-lever model for the toe down angle $\Omega$.

To solve for angle Ω 5601 as previously defined in FIG. 15 the force balance shown in FIG. 18 is applied to accurately determine the toe down angle Ω 5601. A torque 5901 acting on club head 5201 with mass M is generated by the acceleration vector 5902 on the $z_{cm}$-axis 5304 with magnitude $a_z$ acting through the club head 5201 center of mass 5903. The center of mass 5903 is a distance 5904 from the center axis 5905 of club shaft 5202 with length C 5310 and stiffness constant K. The mathematical label for distance 5904 is d. Solving the force balance with the constraints of a flexible shaft K gives an expression for Ω 5601:

$$\Omega = \frac{dC_\Omega}{C}\left(\frac{\frac{Ma_z}{KC}}{1 + \frac{Ma_z}{KC}}\right) \qquad 42.$$

It is worth noting that from equation (42) for increasing values of $a_z$ there is a maximum angle Ω 5601 that can be achieved of d $C_\Omega/C$ which for a typical large head driver is around 4 degrees. The term $C_\Omega$ is a curve fit parameter to account for variable shaft stiffness profiles for a given K. In other words different shafts can have an overall stiffness constant that is equal, however, the segmented stiffness profile of the shaft can vary along the taper of the shaft.

An equation for angle Φ 5501 in terms of angle Ω 5601 can now be found. This is done by first using equation (17) for $a_z$ in equation (15):

$$a_{sy} = a_{sx}\frac{\sin(\Phi)}{\cos(\Phi)} + a_{sz}\cos(\eta)\sin(\Omega) - a_{sx}\frac{\sin(\eta)\sin(\Omega)}{\cos(\Phi)} \qquad 43.$$

Re-arranging terms:

$$(a_{sy} - a_{sz}\cos(\eta)\sin(\Omega))\cos(\Phi) = a_{sx}\sin(\Phi) - a_{sx}\sin(\eta)\sin(\Omega) \qquad 44.$$

Squaring both sides, and using the identity $\cos^2(\Phi) = 1 - \sin^2(\Phi)$ yields a quadratic equation for $\sin(\Phi)$:

$$\sin^2(\Phi)[a_{sx}^2 + (a_{sy} - a_{sz}\cos(\eta)\sin(\Omega))^2] - 2a_{sx}^2\sin(\Phi)\sin(\eta)\sin(\Omega) + a_{sx}^2(\sin(\eta)\sin(\Omega))^2 - (a_{sy} - a_{sz}\cos(\eta)\sin(\Omega))^2 = 0 \qquad 45.$$

Equation (45) has the solution:

$$\sin(\Phi) = \frac{1}{2b_1}\left[-b_2 + \sqrt{b_2^2 - 4b_1 b_3}\right] \qquad 46.$$

where the terms in (46) are:

$$b_1 = a_{sx}^2 + (a_{sy} - a_{sz}\cos(\eta)\sin(\Omega))^2$$

$$b_2 = -2a_{sx}^2\sin(\eta)\sin(\Omega)$$

$$b_3 = a_{sx}^2(\sin(\eta)\sin(\Omega))^2 - (a_{sy} - a_{sz}\cos(\eta)\sin(\Omega))^2$$

Equations (42) for Ω 5601, (46) for Φ 5501, and (20) for η 5401 need to be solved either numerically or iteratively using equations (32) for $a_x$, (33) for $a_z$, and (25) for R 5402.

This task is extremely complex. However, some innovative approximations can yield excellent results with much reduced complexity. One such approach is to look at the end of the power-stroke segment of the swing where $V_R$ and its time derivative go to zero, for which from equations (32), (33), (35) and (40):

$$\eta = C_\eta \tan^{-1}\left(\frac{a_{ch}}{a_{z\text{-}radial}}\right) \qquad 47.$$

In this part of the swing the $a_{sx}$ term will be much smaller than the $a_{sz}$ term and equation (18) can be approximated by:

$$a_z = a_{z\text{-}radial} = a_{sz} \cos(\eta). \qquad 48.$$

During the earlier part of the swing, the curve fit coefficient $C_\eta$ would accommodate non-zero values of $V_R$ and its time derivative as well as the force due to wrist torque 5802.

The maximum value of η 5401 is nominally around 40 degrees for which from (48) $a_{ch}/a_{z\text{-}radial}=1.34$ with $C_\eta=0.75$. So equation (47) is valid for the range from $a_{ch}=0$ to $a_{ch}=1.34\ a_z$-radial, which is about a third of the way into the down-stroke portion of the swing. At the maximum value of η 5401 the vector $a_v$ 5805 is 13 degrees, or 0.23 radians, off alignment with the $z_f$ axis and its projection onto the $z_f$ axis 5105 is $a_{sz}=a_v \cos(0.23)=0.97a_v$. Therefore, this results in a maximum error for the expression (48) for $a_z=a_{z\text{-}radial}$ of only 3%. This amount of error is the result of ignoring the $a_{sx}$ term in equation (18). This physically means that for $a_z$ in this part of the swing the $a_{z\text{-}radial}$ component value dominates that of the $a_{sx}$ component value. Equation (47) can not be blindly applied without first considering the implications for the function $f(\eta)$ defined by equations (13) and (14), which has a functional dependence on $\cos(\Phi)$ through the $a_{sx}$ term, which will not be present when (47) is used in (13). Therefore, this $\cos(\Phi)$ dependence must be explicitly included when using (47) to calculate (13) in equation (12) for $a_{sy}$, resulting in:

$$a_{sy} = (a_x \cos(\eta) - a_z \sin(\eta))\tan(\Phi) + a_z \sin(\Omega). \qquad 49.$$

Equation (49) is applicable only when equation (47) is used for the angle η 5401.

A preferred embodiment is next described that uses the simplifying equations of (47) through (49) to extract results for Φ 5501 and η 5401 using (42) as a model for Ω 5601. It also demonstrates how the wrist cock angle $\alpha_{wc}$ 5701 and shaft flex angle $\alpha_{sf}$ 5702 can be extracted, as well as the mounting angle errors of the accelerometer acceleration measurement assembly. Although this is the preferred approach, other approaches fall under the scope of this invention.

The starting point is re-writing the equations in the following form using the approximations $a_{z\_}=a_{z\text{-}radial}$ and $a_x=a_{ch}$. As discussed above these are excellent approximations in the later part of the swing. Re-writing the equations (4) and (49) with these terms yields:

$$a_{sx} = a_{ch} \cos(\Phi)\cos(\eta) - a_{z\text{-}radial}\cos(\Phi)\sin(\eta) \qquad 50.$$

$$a_{sy} = a_{ch} \tan(\Phi)\cos(\eta) + a_{z\text{-}radial}\sin(\Omega) - a_{z\text{-}radial}\tan(\Phi)\sin(\eta) \qquad 51.$$

$$a_{z\text{-}radial} = a_{sz}\cos(\eta) \qquad 52.$$

Simplifying equation (31):

$$a_{ch} = \frac{dV}{dt} \qquad 53.$$

In this approximation $V=V_\Gamma$ is the club head velocity and dt is the time increment between sensor data points. The instantaneous velocity of the club head traveling on an arc with radius R is from equation (29):

$$V = \sqrt{a_{z\text{-}radial} R} = a_{z\text{-}radial}^{1/2} R^{1/2} \text{ for which:} \qquad 54.$$

$$a_{ch} = \frac{dV}{dt} = \frac{1}{2}\left(\frac{1}{R}\frac{dR}{dt} + \frac{1}{a_{z\text{-}radial}}\frac{da_{z\text{-}radial}}{dt}\right)\sqrt{R a_{z\text{-}radial}} \qquad 55.$$

Using equation (52) for $a_{z\text{-}radial}$ in (55):

$$a_{ch} = \frac{1}{2}\left(\frac{1}{R}\frac{dR}{dt} + \frac{1}{a_{sz}}\frac{da_{sz}}{dt} - \tan(\eta)\frac{d\eta}{dt}\right)\sqrt{R a_{sz} \cos(\eta)} \qquad 56.$$

During the early part of the downswing, all the derivative terms will contribute to $a_{ch}$, but in the later part of the downswing when R is reaching its maximum value, $R_{max}$, and η is approaching zero, the dominant term by far is the $da_{sz}/dt$ term, which allows the simplification for this part of the swing:

$$a_{ch} = \frac{1}{2}\left(\frac{1}{a_{sz}}\frac{da_{sz}}{dt}\right)\sqrt{R a_{sz} \cos(\eta)} \qquad 57.$$

With discreet sensor data taken at time intervals Δt, the equivalent of the above is:

$$a_{ch} = \frac{\sqrt{R \cos(\eta)}}{\Delta t}\left(\sqrt{a_{sz}(t_n)} - \sqrt{a_{sz}(t_{n-1})}\right) \qquad 58.$$

It is convenient to define the behavior for $a_{ch}$ for the case where $R=R_{max}$ and η=0, so that from equation (52) $a_{z\text{-}radial}=a_{sz}$, which defines:

$$a_{chsz} = \frac{\sqrt{R_{max}}}{\Delta t}\left(\sqrt{a_{sz}(t_n)} - \sqrt{a_{sz}(t_{n-1})}\right) \qquad 59.$$

Then the inertial spatial translation acceleration component of the club head is:

$$a_{ch} = a_{chsz}\frac{\sqrt{R \cos(\eta)}}{\sqrt{R_{max}}} \qquad 60.$$

Substituting equation (52) and (60) back into equations (50) and (51) we have the equations containing all golf swing metric angles assuming no acceleration measurement assembly mounting angle errors in terms of direct measured sensor outputs:

$$a_{sx} = a_{chsz}(\sqrt{R\cos(\eta)}/\sqrt{R_{Max}})\cos(\Phi)\cos(\eta) - a_{sz}\cos(\eta)\cos(\Phi)\sin(\eta) \quad 61.$$

$$a_{sy} = a_{chsz}(\sqrt{R\cos(\eta)}/\sqrt{R_{Max}})\tan(\Phi)\cos(\eta) + a_{sz}\cos(\eta)\sin(\Omega) - a_{sz}\cos(\eta)\tan(\Phi)\sin(\eta) \quad 62.$$

Using equation (62) to solve for $\Phi$, since this is the only equation that contains both $\eta$ and $\Omega$, yields:

$$\tan(\Phi) = \frac{a_{sy} - a_{sz}\cos(\eta)\sin(\Omega)}{a_{chsz}(\sqrt{R\cos(\eta)}/\sqrt{R_{Max}})\cos(\eta) - a_{sz}\cos(\eta)\sin(\eta)} \quad 63.$$

Now there are two equations with three unknowns. However, one of the unknowns, $\eta$, has the curve fit parameter $C_\eta$ that can be iteratively determined to give best results for continuity of the resulting time varying curves for each of the system variables. Also, there are boundary conditions from the multi-lever model of the swing that are applied, to specifics points and areas of the golf swing, such as the point of maximum club head velocity at the end of the downstroke, where:
1. For a golf swing approaching max velocity the value of $\eta$ approaches zero,
2. $\Omega$ is at a maximum value when centrifugal force is highest, which occurs at maximum velocity.
3. The club face angle, $\Phi$, can vary greatly at maximum club head velocity. However, regardless of the angle at maximum velocity the angle is changing at a virtual constant rate just before and after the point of maximum club head velocity.

This knowledge allows for all equations to be solved, through an interactive process using starting points for the curve fit parameters.

The angle $\Omega$ 601 is a function of $a_{sz}$ through equations (42), (48) and (52). The curve fit constant, $C_\Omega$, is required since different shafts can have an overall stiffness constant that is equal, however, the segmented stiffness profile of the shaft can vary along the taper of the shaft. The value of $C_\Omega$ will be very close to one, typically less than 1/10 of a percent variation for the condition of no acceleration measurement assembly mounting angle error from the intended alignment. Values of $C_\Omega$ greater or less than 1/10 of a percent indicates a acceleration measurement assembly mounting error angle along the $y_{cm}$-axis which will be discussed later. Re-writing equation (42) using (52):

$$\Omega = \frac{C_\Omega d m_s a_{sz} \cos(\eta)}{C(KC + m_s a_{sz} \cos(\eta))} \quad 64.$$

The constants in equation (64) are:
$C_\Omega$ Multiplying curve fit factor applied for iterative solution
d Distance from housel to center of gravity (COG) of club head
$m_s$ mass of club head system, including club head and Club Head Module
$a_{sz}$ The measured $z_f$-axis 5105 acceleration force value
K Stiffness coefficient of shaft supplied by the golfer or which can be determined in the calibration process associated with the user profile entry section of the analysis program
C Club length The angle $\eta$ 5401 is found from equation (47):

$$\eta = C_\eta \tan^{-1}\left(\frac{a_{ch}}{a_{z\text{-}radial}}\right) \quad 65.$$

The curve fit parameter, $C_\eta$, has an initial value of 0.75.

An iterative solution process is used to solve equations (61), (63), and (64), using (65) for $\eta$ 401, which has the following defined steps for the discreet data tables obtained by the sensors:
1. Determine from sample points of $a_sz$ the zero crossing position of $a_{chsz}$. This is the point where the club head acceleration is zero and therefore the maximum velocity is achieved. Because the samples are digitized quantities at discrete time increments there will be two sample points, where $a_{chsz}$ has a positive value and an adjacent sample point where $a_{chsz}$ has a negative value.
2. Course tune of $\Omega$ 5601: Use initial approximation values to solve for the numerator of $\tan(\Phi)$ of equation (63) with respect to the sample point where $a_{ch}$ passes through zero:
   a. Numerator of $\tan(\Phi) = \{a_{sy} - a_{sz}\cos(\eta)\sin(\Omega)\}$
   b. The numerator of $\tan(\Phi)$ in equation 63 represents the measured value of $a_{sy}$ minus $a_{z\text{-}radial}$ components resulting from angle $\Omega$ with the following conditions at maximum velocity:
      i. Toe down angle $\Omega$, which is at its maximum value at maximum club head velocity, where maximum $a_{sz}$ is achieved at $\eta=0$, for which $a_{sz}=a_{z\text{-}radial}$ From equation (52).
      ii. Angle $\eta$ 5401, which is a function of wrist cock and shaft flex lag/lead, is zero when maximum velocity is reached and $a_{ch}$ is zero.
   c. Use the multiplying constant $C_\Omega$ to adjust the $\Omega$ 5601 equation so that the $\tan(\Phi)$ numerator function sample point value, equivalent to the first negative sample point value of $a_{ch}$, is set to the value zero.
3. Use new course tune value for the $\Omega$ 5601 function to calculate $\Phi$ 5501 from equation (63) for all sample points.
4. Next, fine tune the multiplying constant $C_\Omega$ of the $\Omega$ 5601 function by evaluating the slope of $\Phi$ 5501, for the point pairs before, through, and after maximum velocity.
   a. Examine sample point pairs of the total $\tan(\Phi)$ function given by equation (63) before maximum velocity, through maximum velocity, and after maximum velocity, evaluating slope variation across sample pairs.
   b. Evaluate sequential slope point pairs comparing slopes to determine a variation metric.
   c. Tune multiplying constant $C_\Omega$ of $\Omega$ 5601 function in very small increments until the slope of $\Phi$ 5501 of all sample point pairs are equivalent.
   d. Now the value of the $\Omega$ function is defined but the value of $\eta$ is still given with the initial value of $C_\eta=0.75$. Therefore, even though the value of $\Phi$ 5501 is exact for values very near max velocity where $\eta$ 5401 approaches zero, values of $\Phi$ 5501 are only approximations away from maximum velocity since $\Phi$ 5501 is a function of $\eta$ 5401, which at this point is limited by the initial approximation.

5. Calculate all sample points for the for the following functions:
   a. The fine tuned function $\Omega$ 5601
   b. Approximate function $\eta$ 5401 with $C_\eta$=0.75.
   c. Function $\Phi$ 5501 from equation (63)
      i. Which will be exact for sample points close to maximum velocity
      ii. Which will be an approximation for the sample points away from max velocity because the function $\eta$ 5401 is still an approximate function.
6. Tune the multiplying curve fit constant $C_\eta$ of the $\eta$ 5401 function using equation (61). This is done by rewriting equation (61) into a form which allows the comparison of $a_{sx}$ minus the $a_{sz}$ components which must be equal to $a_{chsz}$. The evaluation equation is from (61):
   a ...

$$\{a_{sx}+a_{sz}\cos(\eta)\cos(\phi)\sin(\eta)\}/\{\cos(\phi)\cos(\eta)\}=a_{chsz}(\sqrt{R}\cos(\eta)/\sqrt{R_{Max}})$$

b. If everything were exact, the two sides of this equation would be equal. If not, they will differ by the variance:

$$\text{Variance}=\{a_{sx}+a_{sz}\cos(\eta)\cos(\phi)\sin(\eta)\}/\{\cos(\phi)\cos(\eta)\}-a_{chsz}(\sqrt{R}\cos(\eta)/\sqrt{R_{Max}})$$

c. This variance metric is summed across a significant number of sample points before and after maximum velocity for each small increment that $C_\eta$ is adjusted.
   d. The minimum summed variance metric set defines the value of the constant $C_\eta$ for the $\eta$ 5401 function.
7. Compare the value of $C_\eta$ obtained at the conclusion of the above sequence with the starting value of $C_\eta$, and if the difference is greater than 0.1 repeat steps 3 through 7 where the initial value for $C_\eta$ in step 3 is the last iterated value from step 6.d. When the difference is less than 0.1, the final value of $C_\eta$ has been obtained.
8. Angle $\alpha$ 5403 is now solved from equation (23) with $\eta$ 5401 across all sample points: $\alpha=\cos^{-1}((R\cos(\eta)-C)/A)$
   a. $\alpha$ 5403 represents the sum of wrist cock angle and shaft flex lag/lead angle as defined by $\alpha=\alpha_{wc}+\alpha_{sf}$.
   b. In a standard golf swing the wrist cock angle is a decreasing angle at a constant rate during the down stroke to maximum club head velocity. Therefore, the angle can be approximated as a straight line from the point where wrist cock unwind is initiated.
   c. The slope of the angle $\alpha_{wc}$ 5701 is:
      i. $[\alpha_{wc}$ (at wrist cock unwind initiation)$-\alpha_{we}$ (club head max Velocity)$]/\Delta T$, where $\Delta T$ is the time duration for this occurrence.
   d. Since $\alpha_{wc}$ 5701 goes to zero at the point of maximum velocity and the time duration $\Delta T$ is known, the function of angle $\alpha_{wc}$ 5701 is now defined.
9. The shaft flex angle $\alpha_{sf}$ 5702 is now defined as $\alpha_{sf}=\alpha-\alpha_{wc}$ for all sample points during down stroke. Any deviation from the straight line function of $\alpha_{wc}$ 5701 is due to shaft flex.

The iterative analysis solution described above is based on the club head acceleration measurement assembly being mounted so that the $x_f$-axis 5104, $y_f$-axis 5106, and $z_f$-axis 5105 associated with the club head acceleration measurement assembly 5101 are aligned correctly with the golf club structural alignment elements as previously described in FIG. 11.

Since the acceleration measurement assembly 5101 is installed in the club head during the manufacturing process, the cost of manufacturing the integrated electronics golf club head is higher when more stringent requirements are placed on the orientation accuracy of the acceleration measurement assembly 5101. To reduce this cost the manufacturing accuracy requirements are reduced by using an algorithm that can detect orientation offsets of the acceleration measurement assembly 5101 and correct the measured data in accordance with the detected offset.

During the manufacturing an angle rotation error around the rotation around the $y_f$-axis 5106 causing the $x_f$-axis 5104 and $z_f$-axis 5105 to be misaligned with their intended club structure references. The mathematical label that describes this error angle of rotation is $\lambda$. In addition, there can be an error angle rotation around the $x_f$-axis 5104 causing the $y_f$-axis 5106 and the $z_f$-axis 5105 to be misaligned with the intended club structure references. The mathematical label that describes this angle of rotation is $\kappa$. This mounting error can be experimentally determined using a standard golf swing.

For a linear acceleration path the relationship between true acceleration and that of the misaligned measured value of $a_{sx}$ is given by the following equations where $a_{sx-true}$ is defined as what the measured data would be along the $x_f$-axis 5104 with $\lambda=0$ degrees. A similar definition holds for $a_{sz-time}$ along the $z_f$ axis 5105. Then:

$$a_{sx-true}=a_{sx}/\cos(\lambda) \qquad 66.$$

$$a_{sz-true}=a_{sz}/\cos(\lambda) \qquad 67.$$

However, the travel path 5307 is not linear for a golf swing which creates a radial component due to the fixed orientation error between the offset acceleration measurement assembly measurement coordinate system and the properly aligned acceleration measurement assembly measurement coordinate system. As a result, any misalignment of the club head acceleration measurement assembly axis by angle $\lambda$ creates an $a_{z-radial}$ component as measured by the misaligned $x_f$-axis 5104. The $a_{z-radial}$ component contributes to the $a_{sx}$ measurement in the following manner:

$$a_{sx}=a_{sx-true}+a_{sz}\sin(\lambda) \qquad 68.$$

The angle $\lambda$ is constant in relation to the club structure, making the relationship above constant, or always true, for the entire swing. The detection and calibrating correction process of the mounting variation angle $\lambda$ is determined by examining equations (50) and (53) at the point of maximum velocity where by definition:

$\eta$ goes to zero $a_{ch}$ goes to zero

Therefore, at maximum velocity $a_{sx-time}$ must also go to zero. At maximum velocity:

$$a_{sx-true}=a_{sx}-a_{sz}\sin(\lambda)=0 \qquad 69.$$

$$\lambda=\sin^{-1}\left(\frac{a_{sx}}{a_{sz}}\right) \qquad 70.$$

Now the measured data arrays for both the affected measurement axis $x_f$-axis 5104 and $z_f$-axis 5105 must be updated with calibrated data arrays.

$$a_{sx-cal}=a_{sx}-a_{sz}\sin\lambda \qquad 71.$$

$$a_{sz-cal}=a_{sz}/\cos\lambda \qquad 72.$$

The new calibrated data arrays $a_{sx-cal}$ and $a_{sz-cal}$ are now used and replaces all $a_{sx}$ and $a_{sz}$ values in previous equations which completes the detection and calibration of club head acceleration measurement assembly mounting errors due to a error rotation around the $y_f$-axis 5106.

The detection of mounting error angle κ is achieved by evaluating $C_\Omega$ resulting from the iterative solution steps 2 though 4 described earlier. If $C_\Omega$ is not very close or equal to one, then there is an additional $a_z$-radial contribution to $a_{sy}$ from mounting error angle κ. The magnitude of mounting error angle κ is determined by evaluating Ω 601 at maximum velocity from equation (64) where for no mounting error $C_\Omega = 1$. Then the mounting angle κ is determined by:

$$\kappa = (C_\Omega - 1)(dm_s a_{sz} \cos(\eta))/(C(KC + m_s a_{sz} \cos(\eta))) \quad 73.$$

As previously described for mounting angle error λ, the mounting error angle κ affects the two measurement sensors along the $y_f$-axis 5106 and the $z_f$-axis 5105. Consistent with the radial component errors resulting from the λ 1201 mounting angle error, the κ mounting angle error is under the same constraints. Therefore:

$$a_{sy\text{-}cal} = a_{sy} - a_{sz} \sin(\kappa) \quad 74.$$

$$a_{sz\text{-}cal} = a_{sz}/\cos \lambda \quad 75.$$

The new calibrated data arrays $a_{sy\text{-}cal}$ and $a_{sz\text{-}cal}$ are now used and replaces all $a_{sy}$ and $a_{sz}$ values in previous equations which complete the detection and calibration of club head acceleration measurement assembly mounting errors due to a mounting error rotation around the $x_f$-axis 5104.

Thereby, the preferred embodiment described above, is able to define the dynamic relationship between the acceleration measurement assembly 5101 measured axes coordinate system and the inertial acceleration force axes coordinate system using the multi-lever model and to define all related angle behaviors, including acceleration measurement assembly 5101 mounting errors.

All of the dynamically changing golf metrics described as angle and or amplitude values change with respect to time. To visually convey these metrics to the golfer, they are graphed in the form of value versus time. The graphing function can be a separate computer program that retrieves output data from the computational algorithm or the graphing function can be integrated in to a single program that includes the computational algorithm.

The standard golf swing can be broken into four basic interrelated swing segments that include the backswing, pause and reversal, down stroke, also called the power-stroke, and follow-through. With all angles between coordinate systems defined and the ability to separate centrifugal inertial component from inertial spatial translation components for each club head acceleration measurement assembly measured axis, the relationships of the data component dynamics can now be evaluated to define trigger points that can indicate start points, end points, or transition points from one swing segment to another. These trigger points are related to specific samples with specific time relationships defined with all other points, allowing precise time durations for each swing segment to be defined. The logic function that is employed to define a trigger point can vary since there are many different conditional relationships that can be employed to conclude the same trigger point. As an example, the logic to define the trigger point that defines the transition between the back swing segment and the pause and reversal segment is:

If $a_z$-radial(tn) < 1.5g
AND $a_{sx}$-linear(tn) = 0
AND
AVG($a_{sx}$-linear(tn-5) thru $a_{sx}$-linear(tn)) < -1.2g
AND
AVG($a_{sx}$-linear(tn) thru $a_{sx}$-linear(tn+5)) > +1.2g By defining the exact time duration for each swing segment and understanding that each swing segment is related and continuous with an adjacent segment, the golfer can focus improvement strategies more precisely by examining swing segments separately.

For the free swing the ability to correlate the acceleration measurements and resulting dynamics golf metrics time line to a spatial reference allows key dynamics swing metrics to be further evaluated in the contexts of space. This offers golfers great analytical benefit when evaluating a free golf swing that does not impact an object. The swing metrics can be analyzed in relation to key spatial reference locations, such as anticipated ball location, peak elevation of backswing, peak elevation of power-stroke, peak elevation of follow through and others such as club head travel path 90 degrees out from right or left shoulder. These spatial reference points all offer their own set of benefits when analyzing the varied dynamic swing metrics in reference to spatial locations near the club head travel path. True swing efficiency and effectiveness can now be evaluate without the motional perturbations that occur when the golf club strikes and object such as a golf ball. The benefit of analyzing a free swing as opposed to an impact swing can be demonstrated with a fundamental example of evaluating swing efficiency with respect to the dynamic swing metric of club head velocity which is directly related to achievable ball trajectory distance. In this example a golfer may want to improve and optimize their swing style for maximum distance. Using free swing measurements and analysis that provides dynamic club head velocity in relation to an anticipated ball location allows the golfer to evaluate if they are reaching maximum club head velocity before, at, or after the anticipated ball location. This is not possible with club/ball impact because of the abrupt velocity reduction resulting from impact eliminating the ability to determine where maximum velocity would have occurred after impact. Further, the swing style can be modified for maximum power and efficiency by aligning club head maximum velocity with anticipated ball location for maximum energy transfer at anticipated ball location. The same benefit themes demonstrated with the club head velocity example also can be applied to all dynamics swing metrics such as but not limited to, club head spatial acceleration and maximum club head spatial acceleration, club face angle and where the club face angle reached a square position, shaft flex lag/lead angle and many others.

These measurement and evaluation capabilities are not available with swing analyzers that only rely on impact with a golf ball, because the impact itself abruptly changes all swing metrics including club head orientation, club head motion and shaft actions and therefore eliminates the possibility of comprehensive analysis of true swing performance. Only swing analyzers that analyze both free swing and swing and impact completely characterize the need metric for true optimization.

The embodiment of correlation methods are demonstrated using the integration of conventional Receiver Signal Strength Indicator (also referred to as RSSI) functionality into the previously recited free swing measurement and analysis portion of this system. The system uses RSSI to determine relative spatial relationships between the Club Head acceleration measurement assembly 5101 (acceleration measurement assembly) and the wireless USB Module during the entire swing. The spatial relationships, such as nearest together or farthest apart or equivalents or ratios are used to identify club head location(s) at a point or points in time that correspond to time location(s) on the acceleration measurement time line thereby correlating space and time.

Figure 19:
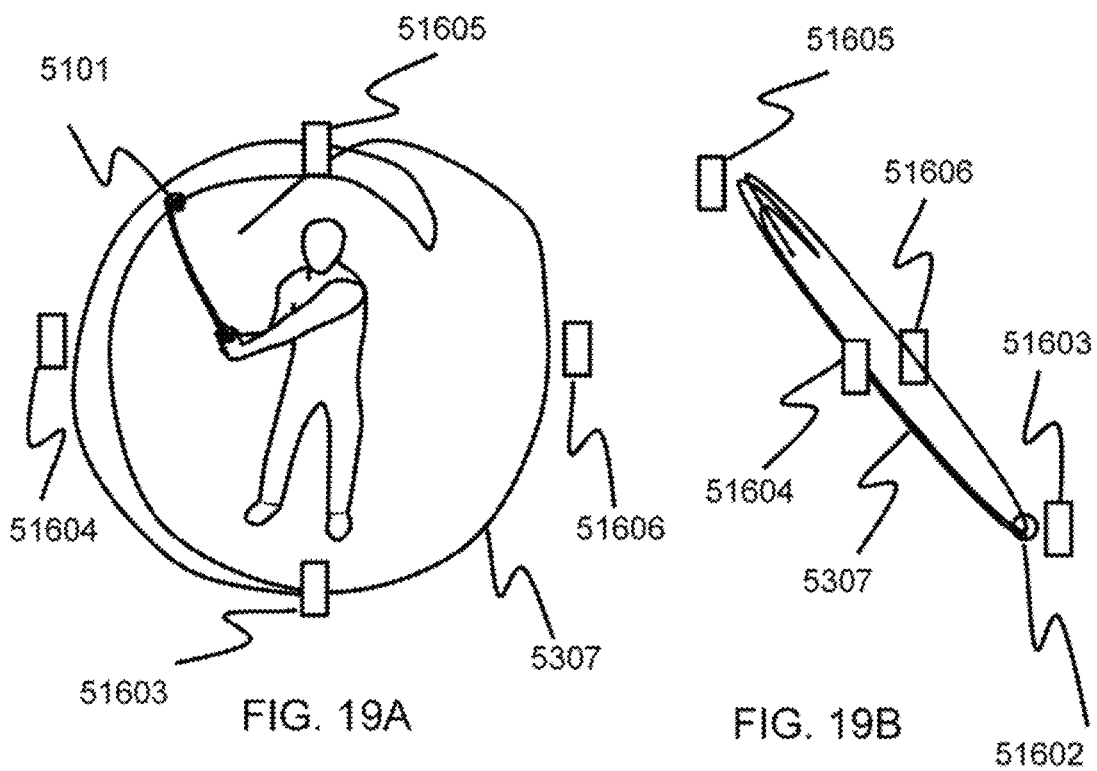
FIG. 19 shows the user interface device, a laptop computer, electrically connected to a cable connected to the wireless USB module that may be placed at predetermined locations near the swing path.
Figure 19:
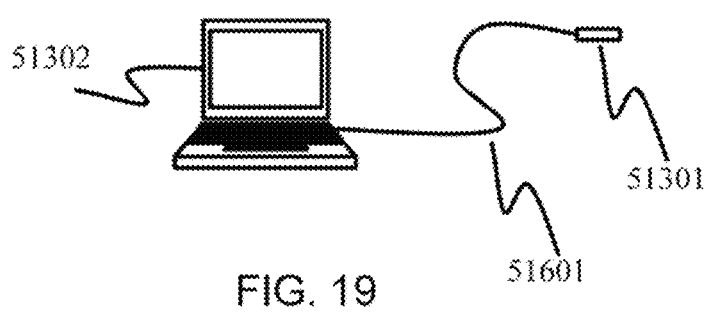

FIGS. 19, 19A and 19B of the embodiment of the time-space correlation shows the system configuration and operation. As shown in FIG. 19 the system comprising a user interface 51302 (a laptop in this example) with computation engine, display and standard input output port connections, in this example a USB port and is connect to a USB Cable 51601 (wired connection) that is further connected to USB Module 51301 (second module). The USB module 51301 (second module) is placed remotely from user interface 51302 at a predetermine location. FIGS. 19A and 19B show a front view perspective and a side view perspective respectively of the club head travel path 5307 of a golf swing and FIG. 19B further shows an anticipated location of a golf ball 51602. A predetermined single location can be anywhere near the anticipated golf head travel path 5307. Examples of predetermined location options can include, but not limited to, location 51603, 51604, 51605 and 51606. In this embodiment the USB module 51301 is located at predetermined location 51603 that is close to club head travel path 5307 and in front of anticipated ball location 51602. Operationally, the golfer takes a swing, the Club Head Acceleration measurement assembly 5101 (acceleration measurement assembly) attached to club head, travels along the club head travel path 5307 and simultaneously Club Head Acceleration measurement assembly 5101 measures three dimensional acceleration and synchronously and time aligned measures received strength for received wireless signal transmitted by USB module 51301. Further, Club Head Acceleration measurement assembly 5101 (acceleration measurement assembly) is capturing and transmitting measurement data comprising acceleration and received signal strength measurements to USB Module 51301 for further transport to User Interface 51302 with computational engine.

A software application of the first embodiment of the time-space correlation resides on User Interface 51302 computational engine and comprising all functions for user interface, display and data processing of measurements within software application. The data processing of measurements includes the previously recited algorithms for club head alignment calibration and acceleration data analysis. Further, software application implements a third algorithm that processes the receiver signal strength measurements in conjunction with synchronized acceleration measurements to determine time space correlation. The third algorithm processes steps of the first embodiment of the time-space correlation include the step of:
1. Digitally low pass filter RSSI measured time line data to reduce effects of RF multipath fading
2. Processes filtered RSSI data using peak detection and minimum detection methods to determine time points on time line of highest and lowest signal strength
3. Flag and label time point of peak RSSI measurement defining the relationship of Club Head Acceleration measurement assembly 5101 and USB Module 51301 at minimum spatial separation.
4. Flag and label time point of minimum RSSI measurement defining the spatial relationship of Club Head Acceleration measurement assembly 5101 and USB Module 51301 at maximum spatial separation.
5. Label the correlated time points on the acceleration measurements and dynamics golf metrics results time line defining space time relationship.

For swing and impact analysis the impact with the ball can serve as the detectable predetermined spatial location on the measurements time line to correlate the measurement time line to space. For impact analysis the determination of key metrics such as, location on club face, duration of impact time, dynamic force profile across club face and total energy of impact based on direct measurements of the sensor elements with known placement within the club face. The calibration of these sensor elements within the monolith with the club face has been describes in the club face assembly section of this application.

Positive and Negative Impact Pressure Detection

In another embodiment, a distributed sensor system in the club face may measure the pressure resulting from a ball impacting the club face by measuring both increasing and decreasing relative pressure from a static pressure state. The increasing pressure may be described as a positive pressure, whereas the decreasing pressure may be described as a negative pressure. The increase (positive) and/or decrease (negative) in pressure may be detected at a plurality of piezoelectric sensor elements. For example, the impact may cause deformation of the club face structure that includes both deforming the club face inward (increasing pressure) at one location while also deforming the clubface outward (decreasing pressure) at another location. As described below with regard to FIGS. 20A-C, one or more sensors may track both types of deformations, creating time-varying impact pressure profiles based on both the positive and negative pressures that are generated.

Figure 20A:
FIGS. 20A-C are exemplary illustrations of an impact measurement system, in accordance with an embodiment.

Turning to FIG. 20A, a cross section of a curved club face surface 270 is shown, in an idle position 271. For example, a driver may have a convex hitting surface such as the one shown in FIG. 20A. Although the curved surface 20A is used as an example for discussion purposes, similar measurements as described herein may also be accomplished with a flat surface, and can be used for all club types, such as drivers, hybrids, irons, wedges and putters.

Figure 20B:
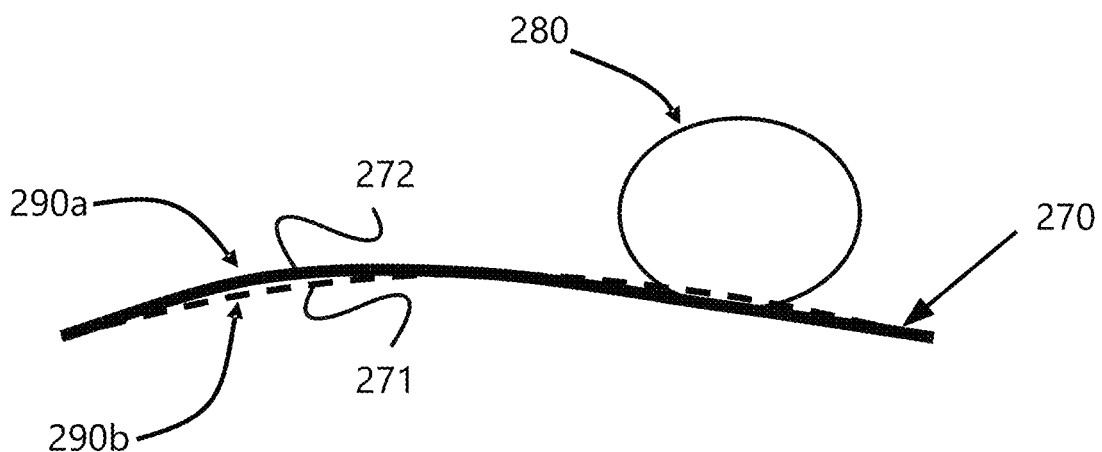

FIG. 20B illustrates an exemplary impact of a ball 280 with a club face surface 270. As shown in this example, the ball 280 may compress upon impact with the club face surface 270, and the club face surface 270 may deform inward at the impact location. As shown, the club face surface 270 may deform into position 272 (solid line), which is shown relative to the idle position 271 (dashed line) for illustrative purposes. In so doing, while a location at the impact point may be pressed inward, another location on the club face may be pushed outwards from the stress and strains of the impact that are translated in the club face and club head structure. The distance between reference points 290a and 290b shows an example of the club face being pushed outwards at a location on the other side of the club face relative to the impact point.

Figure 20C:
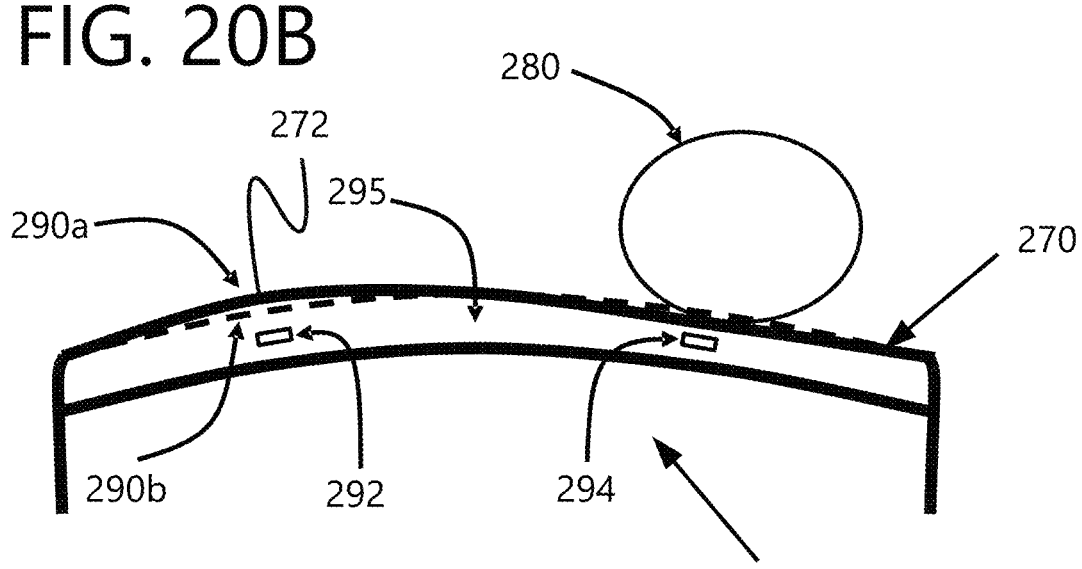

Turning now to FIG. 20C, an exemplary club face distributed sensor system 299 is shown. In one embodiment, the club face distributed sensor system 295 can measure both positive and negative time-varying impact pressure values on piezoelectric sensor elements caused by the deformation of the club face structure and, through measuring both, create a more accurate and reliable time-varying impact pressure profile. This may allow a golfer to more accurately assess the impact of a golf swing on a ball 280, and better determine what adjustments to make to his or her swing.

In the example of FIG. 20C, pressure sensors 292 and 294 are piezoelectric sensors that are embedded in a monolith 295. Although only two sensors 292 and 294 are illustrated, more or less than two impact sensors may be used in another embodiment.

The pressure sensitivity and deformation measurement capability of the piezoelectric sensor elements 292 and 294 within the monolith 295 may be altered and enhanced in one embodiment by applying a static compression force on the monolith 295 and, in this example, embedded piezoelectric elements 292 and 294. In other words, a static compression pressure may be exerted on the monolith 295 and embedded sensor elements 292 and 294 even when there are no external impacts occurring on the club face.

Applying static pressure to compress the monolith 295 may increase the sensitivity and dynamic range of negative impact pressure caused by the club face surface bowing outward. However, such adjustment may simultaneously reduce the dynamic range of the positive impact pressure measureable due to the inherent linear range limit of signal amplitude or charge quantity versus material deformation of piezoelectric materials.

The piezoelectric material element may have a physical deformation limit for both compression strain (reduction in thickness) or stretching strain (increase in thickness) and beyond these limits produce minimal changes in surface charge creation. Thus, the flow of the charge between poles of the piezoelectric element, which defines the amplitude of signal being generated by the piezoelectric element, may be limited based on the physical deformation limits, which may be taken into consideration when applying a static compression as an offset. Many of the higher electromechanically coupling piezoelectric material classes, such as piezo-ceramics have much higher usable linear operation ranges from compression forces causing a compressive deformation as opposed to tensile forces causing stretching or elongations deformation. The limited dynamic ranges of tensile forces causing stretching for piezo electric sensor elements may create catastrophic failures that include the piezo material cracking and/or the conducting electrodes be pull off for the piezo material if limits are surpassed. This may be taken into account when applying static compression to create an offset.

In another embodiment, the static pressure may be applied non-uniformly to the monolith, such that different pressure sensors of the same type within the monolith receive different static pressures. This may be used, for example, to calibrate the different sensors based on their relative locations to the edge of the monolith.

Figure 21:
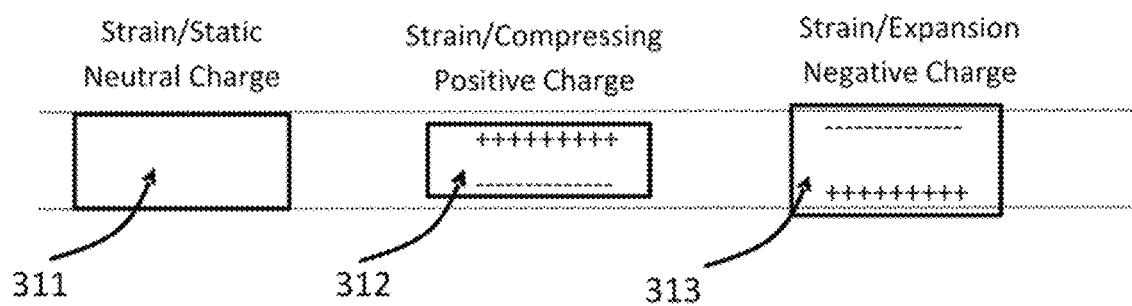
FIGS. 21-21B are exemplary illustrations of an impact measurement system, in accordance with an embodiment.

Turning to FIG. 21, an example piezoelectric material element is shown in three different strain states 311, 312, and 313, with a polarity of associated surface charge resulting from each strain state 311, 312, and 313. The piezo element in a static strain state 311 can be defined as having a neutral charge balance between the upper and lower surfaces (i.e., poles) of the piezoelectric element. The static state may include an amount of compression in one embodiment. However, upon impact, dynamic states may occur that cause a charge differential between the front and back surfaces of the piezo element. For example, the piezo element may enter a dynamic compressed strain state 312, causing a positive surface charge relative to the piezo element in the static strain state 311. Further, the piezo element may enter a dynamic expansion stain state 313 and have a negative surface charge as relative to the piezo element in a static strain state 311.

The flow of this charge across a load, from one pole to the other, essentially may define a pressure signal being output from the piezo electric material. Thus, a dynamic compression strain placed upon impact may produce a positive signal, whereas an expansion strain upon impact may produce a negative signal.

Figure 21A:
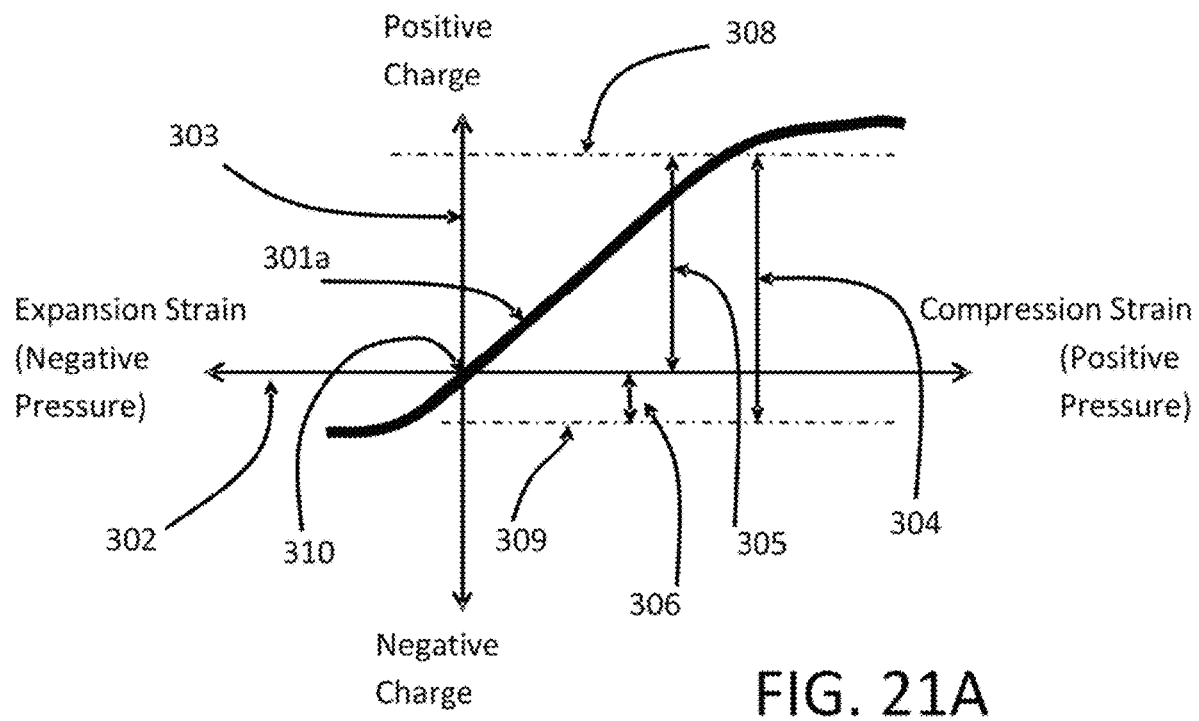

FIG. 21A shows an example piezo element dynamic strain deformation to surface charge relationship curve 301a for a piezo element with no static pre-compression. The neutral point 310 represents where no dynamic (e.g., impact) strain is taking place and there is neutral surface charge relationship on the piezo element surfaces. The piezo element dynamic strain deformation to surface charge relationship curve 301 has a linear range wherein the quantity of charge generated caused by a magnitude of strain deformation is a fixed ratio. The linear range upper limit 308 and lower limit 309 define the piezo element linear operating dynamic range 304. In one embodiment, the linear operating range 304 can further be segmented into a positive charge linear operating range 305 and a negative charge linear operating range 306. As can be seen, the positive charge linear operating range 305 caused by compression may be much larger than the negative charge linear operating range 306 caused by expansion.

Figure 21B:
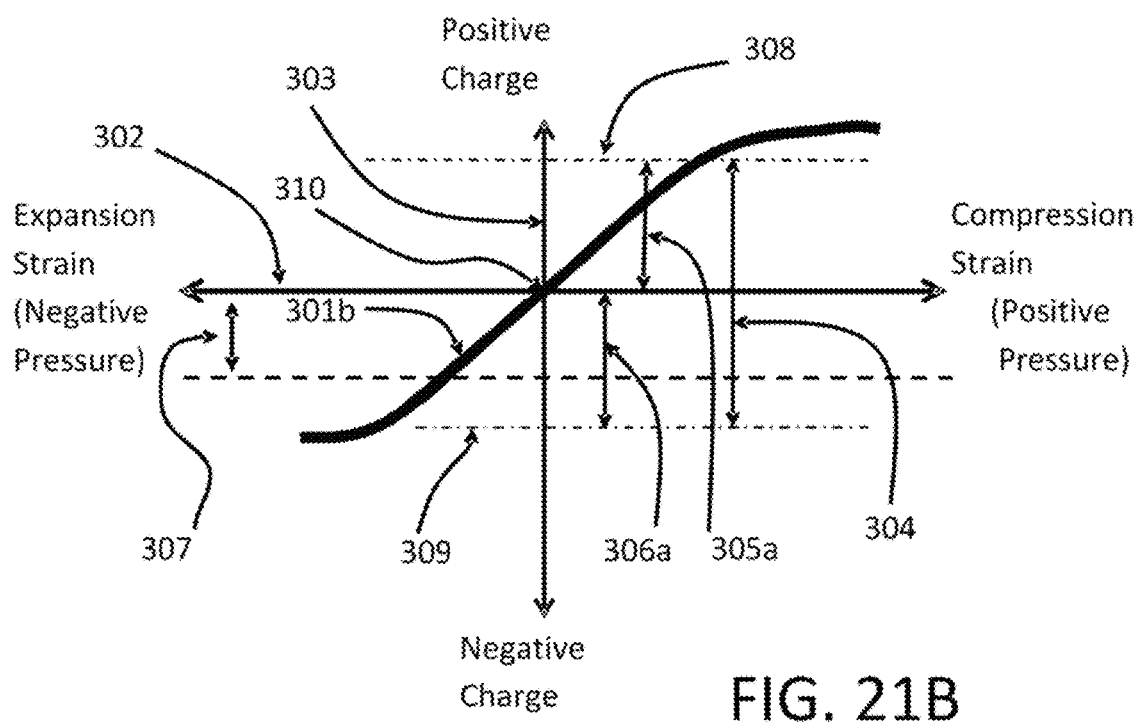

FIG. 21B shows an example dynamic strain deformation to surface charge relationship curve 301b for a piezo element with static pre-compression added. The addition of an amount of static pre compression 307 to the piezo element may cause the piezo element linear operating dynamic range 304 to be more evenly divided between the positive charge linear operating range 305a (caused by compression) and a negative charge linear operating range 306a (caused by expansion). This may enable the relative negative pressure resulting from a portion of the club face bowing outward to be fully measureable in one embodiment. In other words, by applying static pressure to compress the monolith 295, the dynamic range and measurement capability may be increased with regard to club face 270 surface deformations 272 that bow outward (e.g., between 290b and 290a) based on an impact on the club face surface at another location.

Returning to FIG. 20C in view of the above, by pre-compressing the sensor elements 292 and 294 with a static pressure (in a non-impact state), the dynamic range of the sensor elements 292 and 294 may be simultaneously reduced for positive pressure and increased for negative pressure. Both measurements may be utilized in determining an impact pressure in one embodiment. For example, upon impact with a golf ball, a portion of the surface bowing outward may be measured as a negative pressure. This may provide information regarding location of impact (away from the negative pressure point), and also may be utilized to more accurately measure the positive pressure at the impact point. For example, because this outward bowing (e.g., between 290b and 290a) reduces the pressure experienced by the sensor element 294, measuring this negative pressure at sensor 292 may allow the system 299 to provide data for creation of a more accurate time-varying impact pressure profile.

In another example, only one impact sensor may be used to detect impact location based on positive or negative pressure. For example, the impact pressure sensor may be offset from the center of the monolith such that a negative pressure indicates that impact occurred on the other side of the center of the monolith relative to the impact sensor.

Continuing with the example of FIG. 20C, the system 299 may include pressure measurement circuitry coupled to the plurality of piezoelectric elements 292 and 294. The pressure measurement circuitry may measure positive and negative pressures on the first and second piezoelectric elements 292 and 294, wherein the positive and negative pressures are measured over a plurality of sample points during impact of a golf ball with the club face and used to build a time-varying impact pressure profile. The pressure measurement circuitry may be implemented as part of the controller (i.e., processor) in one embodiment, and may utilized analog to digital converters, such as is shown in FIG. 8.

Additionally, the positive and negative impact pressure values may be sampled simultaneously (at the same point in time) in one embodiment. For example, the outputs of each of the first sensor 292 and second sensor 294 may be captured in parallel. If the ball impacts the club closer to the second sensor 294, as shown in the example of FIG. 20C, then the circuitry may simultaneously capture a negative value from the first sensor 292 (based on outward flexing) and a positive value from the second sensor 294 (based on inward compression).

The system 299 may transmit these values to a receiver, such as a computer, that builds an impact pressure profile based on multiple samples that occur during impact, including multiple sets of simultaneous samples. The receiver may utilize the negative pressure values to better calculate the actual pressure on the club face by compensating the positive pressure values. The receiver may also better detect the location of impact on the club face based on a pressure comparison that includes negative pressure values in the analysis.

As described previously with regard to FIGS. 21-21B, in one embodiment, the sensor element sensitivity, dynamic range and ability to measure both inward and outward deformation can be adjusted by adjusting the static pressure on the monolith in a non-impact state. A fixed static compression from the manufacture or a mechanical mechanism can be built into the club head in one embodiment, and in addition or alternatively, the golfer may adjust the monolith compression with a screw. For example, static compression may be adjusted by turning a screw that applies pressure by tightening a vice on the front and back (internal at the cavity) sides of the monolith. In another embodiment, the static pressure is applied primarily to the internal side of the monolith 295. Also, more elaborate mechanical mechanisms can be used to allow the golfer to adjust different portions of the club face separately.

Adjusting the static pressure, and thereby adjusting sensitivity, may beneficially allow for accurate measurement impact at different club speeds. For example, the same club may be adjusted differently to increase pressure to analyze a golfer who has a 70 mile per hour swing (e.g., more sensitivity needed) versus a 140 mile per hour swing (e.g., less sensitivity needed). This type of measurement can also be used in club fitting, where the club face structural design is based on typical swing speed of the golfer, similar to how staff stiffness is adjusted during a club fitting.

In another embodiment, the club head system 299 may automatically adjust the static pressure placed on the monolith and embedded sensors. For example, the processor (e.g., controller) in the club head system 299 may detect a club speed or may be in communication with a receiver (e.g., computer) that calculates club speed based on swing data received from the club head. In response to determining that club speed is relatively high, such as 140 miles per hour, the controller (e.g., processor) may decrease the static pressure (e.g., by 15%) because less sensitivity is needed. Whereas a relatively slow club swing, such as 70 miles per hour, could cause the controller in system 299 to increase the static pressure to create more sensitivity.

In still another embodiment, the system 299 may automatically adjust the pressure based on the speed of the club swing. The receiver may determine that adjustment is necessary based on its calculations of both swing and impact data (e.g., perceiving a fast swing versus a high static pressure). In this case, the receiver may send a message to the club head and the controller (i.e., processor) in system 299 may actuate a small motorized screw, clamp, or other mechanism for generating pressure on the monolith 295. In another embodiment, the processor in the club head may detect a threshold difference in swing speed versus static pressure and trigger the adjustment.

Alternatively, the receiver may track the static pressure and the club swing, and alert the user to manually adjust the static pressure based on a threshold difference between the present static pressure and optimal static pressure based on an average club swing over the last several (e.g., 5) swings.

In addition, in one embodiment a custom club face structure may be fabricated quickly at golf fitting locations using 3D printing. Design parameters for the custom club face may be based on motional swing and club face impact analysis on a per golfer basis. Thus, using an embodiment herein, custom club faces may also be possible during a club fitting.

The first step of creating the custom club face may include characterizing the golfer impact profile with respect to power, consistency, and broadness of skill sets. The golfer's power can be characterized by the typical club head velocity when the club head hits the ball. The golfer's impact consistency may be determined via a statistical analysis over many hits of the impact location on the clubface. The consistency impact location analysis where the average and median impact location are with respect to the ideal sweet spot and also statistical standard deviations the average and median location.

Finally, the broadness of the golfers skill sets may be analyzed. The broadness of skills analysis may include determining the different impact methods a golfer uses, such as impacts that are intended to create a varying degrease of ball spin and direction of spin, such as a draw. The custom club face design may have a customizable thickness profile that varies for different locations of the club face to counter or accentuate the impact methods common with the particular golfer. These different areas of offer tradeoff in localized stiffness and can be used for trading off a large size of the sweet spot for a smaller rigid sweet spot that offers more power. Further, using close proximity thicker and thinner areas can create small wave type deformation during impacts that can help grip the ball enhancing the ability to intentionally apply spin to the ball.

Although specific embodiments of the invention have been disclosed, those having ordinary skill in the art will understand that changes can be made to the specific embodiments without departing form the spirit and scope of the invention. The scope of the invention is not to be restricted, therefore, to the specific embodiments. Furthermore, it is intended that the appended claims cover any and all such applications, modifications, and embodiments within the scope of the present invention.

Although particular materials are mentioned as examples herein, these examples are not exhaustive. Other materials may be used to build a roll-up shelf in accordance with an embodiment herein.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An impact analysis system, including:
a first piezoelectric element embedded in a moveable object;
a first signal divider that receives a first power signal that is output from the first piezoelectric element based on both impact to the moveable object and vibrations of the moveable object, the first signal divider having a first output and a second output, wherein the first output is coupled to signal processing circuitry and the second output is coupled to an energy storage assembly that includes a battery; and
a processor that is configured to dynamically adjust a ratio of a first amount of the first power signal the first signal divider sends through the first output to the signal processing circuitry versus a second amount of the first power signal the first signal divider sends through the second output to the energy storage assembly, wherein the processor is further configured to perform impact analysis of the impact to the moveable object.

2. The impact analysis system of claim 1, wherein the processor is further configured to:
detect a threshold level of acceleration has been met; and
in response to the threshold being met, adjust the ratio so that more of the first power signal is sent through the first output to the signal processing circuitry.

3. The impact analysis system of claim 2, wherein in response to the threshold being met, the processor is further configured to dynamically increase a sampling rate of the signal processing circuitry.

4. The impact analysis system of claim 1, wherein the processor is further configured to detect the impact and waits a predetermined time from impact before dynamically changing the ratio to send more of the first power signal through the second output to the energy storage assembly.

5. The impact analysis system of claim 4, wherein the dynamic change to the ratio causes the processor to send all of the power signal through the second output to the energy storage assembly.

6. The impact analysis system of claim 1, wherein the first piezoelectric element measures a combination of parameters that include pressure, linear acceleration, angular acceleration, and torque; and
wherein the first power signal is an analog signal based on surface charge changes of the first piezoelectric element.

7. The impact analysis system of claim 1, further including a second piezoelectric element that outputs a second power signal to a second signal divider, wherein the second signal divider splits the second power signal according to the same dynamically adjustable ratio as the first signal divider, including a first amount and second amount of the second power signal.

8. The impact analysis system of claim 7, wherein the processor is further configured to set first and second multipliers for normalizing samples of the first and second power signals respectively, wherein the second multiplier is set differently than the first multiplier to compensate for the second piezoelectric element being closer to an edge of a monolith than the first piezoelectric element.

9. The impact analysis system of claim 8, wherein the signal processing circuitry simultaneously samples the respective first amounts of the first and second power signals.

10. The impact analysis system of claim 1, wherein the processor is further configured to set a multiplier for normalizing samples taken by the signal processing circuitry, wherein the multiplier is dynamically changed to compensate for dynamic changes to the first amount.

11. The impact analysis system of claim 1, wherein the moveable object is a golf club, and wherein the first piezoelectric element is embedded in a club face of the golf club.

12. The impact analysis system of claim 1, wherein the processor is further configured to track the first and second amounts as they change over time.

13. The impact analysis system of claim 1, wherein the processor is further configured to dynamically change the ratio of the first and second amounts based on a preprogrammed time line that is based on at least one trigger event.

14. A moveable object comprising:
a first pressure sensor embedded in a face of the moveable object;
a first signal divider that receives a first power signal that is output from the first pressure sensor based on both impact to the moveable object and vibrations of the moveable object, the first signal divider having a first output and a second output, wherein the first output is coupled to signal processing circuitry and the second output is coupled to an energy storage assembly that includes a battery; and
a processor that is configured to dynamically adjust a ratio of how much of the first power signal the signal divider sends through the first output to the signal processing circuitry versus how much of the first power signal the signal divider sends through the second output to the energy storage assembly, wherein the processor is further configured to perform impact analysis of the impact to the moveable object.

15. The moveable object of claim 14, wherein the moveable object is a golf club head and wherein the first pressure sensor is embedded in a side wall of the golf club head.

16. The moveable object of claim 14, further including a second pressure sensor that outputs a second power signal, wherein a portion of the second power signal is sent to the energy storage assembly in accordance with the ratio set by the processor.

17. The moveable object of claim 16, wherein the processor is further configured to set first and second multipliers for normalizing samples of the first and second power signals respectively, wherein the second multiplier is set differently than the first multiplier to compensate for the second pressure sensor being closer to an edge of a golf club head than the first pressure sensor.

18. The moveable object of claim 14, wherein the processor is further configured to cause substantially all of the first power signal to be sent to the energy storage assembly until the processor enters an impact analysis state.

19. The moveable object of claim 18, wherein in the impact analysis state, the processor is further configured to cause substantially all of the first power signal to be sent to the signal processing circuitry.

20. A device that attaches to a moveable object, the device comprising:
a first pressure sensor embedded in a wall that makes contact with the moveable object;

a first signal divider that receives a first power signal that is output from the first pressure sensor based on both impact to the moveable object and vibrations of the moveable object, the first signal divider having a first output and a second output, wherein the first output is coupled to signal processing circuitry and the second output is coupled to an energy storage assembly that includes a battery; and a processor that is configured to dynamically adjust how much of the first power signal the first signal divider sends through the first output to the signal processing circuitry versus how much of the first power signal the first signal divider sends through the second output to the energy storage assembly, wherein the dynamic adjustment is made automatically by the processor, and wherein the processor is further configured to perform impact analysis of the impact to the moveable object.

* * * * *